US012063902B2

(12) United States Patent
Flaishman et al.

(10) Patent No.: US 12,063,902 B2
(45) Date of Patent: Aug. 20, 2024

(54) METHOD OF REGENERATING CANNABIS

(71) Applicant: The State of Israel, Ministry of Agriculture & Rural Development, Agricultural Research Organization (ARO) (Volcani Center), Rishon-LeZion (IL)

(72) Inventors: Moshe Arie Flaishman, Herzliya (IL); Reut Cohen Peer, Kiryat-Ono (IL); Oded Cohen, Nir Zvi (IL); Samuel Bocobza, Tel Aviv (IL)

(73) Assignee: The State of Israel, Ministry of Agriculture & Rural Development, Agricultural Research Organization (ARO) (Volcani Center), Rishon-LeZion (IL)

( * ) Notice: Subject to any disclaimer, the term of this patent is extended or adjusted under 35 U.S.C. 154(b) by 0 days.

(21) Appl. No.: 17/861,459

(22) Filed: Jul. 11, 2022

(65) Prior Publication Data
US 2022/0386547 A1 Dec. 8, 2022

Related U.S. Application Data

(63) Continuation of application No. 16/972,647, filed as application No. PCT/IL2019/050653 on Jun. 6, 2019, now abandoned.

(60) Provisional application No. 62/681,697, filed on Jun. 7, 2018.

(51) Int. Cl.
| | |
|---|---|
| *A01H 4/00* | (2006.01) |
| *A01G 22/00* | (2018.01) |
| *A01H 6/28* | (2018.01) |
| *A01G 31/00* | (2018.01) |

(52) U.S. Cl.
CPC .............. *A01H 4/005* (2013.01); *A01G 22/00* (2018.02); *A01H 4/008* (2013.01); *A01H 6/28* (2018.05); *A01G 31/00* (2013.01)

(58) Field of Classification Search
CPC .......... A01H 4/005; A01H 4/008; A01H 6/28; A01G 22/00; A01G 31/00
See application file for complete search history.

(56) References Cited

U.S. PATENT DOCUMENTS

| | | | |
|---|---|---|---|
| 8,012,752 B2 * | 9/2011 | Jayakumar | C12N 5/04 435/410 |
| 9,528,097 B2 * | 12/2016 | Dias | C12N 9/2422 |
| 2012/0311744 A1 | 12/2012 | Sirkowski | |
| 2021/0337753 A1 | 11/2021 | Flaishman et al. | |

FOREIGN PATENT DOCUMENTS

| | | |
|---|---|---|
| CN | 1887043 | 1/2007 |
| CN | 107360958 | 11/2017 |
| CN | 107630034 | 1/2018 |
| WO | WO 2017/025967 | 2/2017 |
| WO | WO 2019/234750 | 12/2019 |

OTHER PUBLICATIONS

Bhojwani et al. Chapter 12 Protoplast isolation and culture, Studies in Plant Science, vol. 5, 1996, 337-372. (Year: 1996).*
Dhed'a et al. Plant regeneration in cell suspension cultures of the cooking banana cv. Bluggoe' (*Musa spp.* ABB group) Fruits vol. 46, No. 2, 1991 125-135. (Year: 1991).*
Jones. Master of Science Thesis 1979, pp. 1-46 and 82-85. (Year: 1979).*
Panis et al. Plant regeneration through direct somatic embryogenesis from protoplasts of banana (*Musa spp.*) Plant Cell Reports ( 1993) 12:403-407. (Year: 1993).*
Richez-Dumanois et al. Agronomie, EDP Sciences 1986, 6(5), 487-495. (Year: 1986).*
Weber et al. Plant Cell Rep (2003) 21:475-482. (Year: 2003).*
English translation of Richez-Dumanois et al. 2021, 32 pp. (Year: 2021).*
English Summary Dated Jun. 2, 2022 of Notification of Office Action and Search Report Dated May 11, 2022 From the State Intellectual Property Office of the People's Republic of China Re. Application No. 201980045932.9. (2 Pages).
International Preliminary Report on Patentability Dated Dec. 17, 2020 From the International Bureau of WIPO Re. Application No. PCT/IL2019/050653. (14 Pages).
International Search Report and the Written Opinion Dated Oct. 2, 2019 From the International Searching Authority Re. Application No. PCT/IL2019/050653. (24 Pages).
Invitation to Pay Additional Fees, Communication Relating to the Results of the Partial International Search and the Provisional Opinion Dated Aug. 5, 2019 From the International Searching Authority Re. Application No. PCT/IL2019/050653. (15 Pages).
Notification of Office Action and Search Report Dated May 11, 2022 From the State Intellectual Property Office of the People's Republic of China Re. Application No. 201980045932.9. (11 Pages).
Official Action Dated Jan. 11, 2022 from US Patent and Trademark Office Re. U.S. Appl. No. 16/972,647. (16 pages).
Bhojwani "Chapter 12 Protoplast Isolation and Culture", Studies in Plant Science, 5:337-372, 1996 abstract 3 pp.
Bhojwani et al. "Protoplast Isolation and Culture", Studies in Plant Science, 5:337-372, 1996.
Chandra et al. "Assessment of Cannbinoids Content in Micropropagated Plants of Cannabis Sativa and Their Comparison With Conventionally Propagated Developmental Stages of Growth", Planta Medica, XP002792251, 76(7): 743-750, Published Online Nov. 30, 2009.
Cheng et al. "A Rapid Shoot Regeneration Protocol From the Cotyledons of Hemp (*Cannabis sativa* L.)", Industrial Crops and Products, XP055564196, 83: 61-65, Available Online Dec. 29, 2015.

(Continued)

*Primary Examiner* — June Hwu

(57) ABSTRACT

Methods of in vitro clonal propagation and regeneration in *Cannabis* are provided. Also provided is the use of such methods in improvements of *cannabis* cultivars such as via breeding.

11 Claims, 14 Drawing Sheets
(14 of 14 Drawing Sheet(s) Filed in Color)
Specification includes a Sequence Listing.

(56) References Cited

OTHER PUBLICATIONS

Cosgrove "Catalysts of Plant Cell Wall Loosening [Version 1; Referees: 2 Approved]", F1000Resarch, 5: 119-1—119-13, Jan. 29, 2016.

Frankova et al. "Biochemistry and Physiological Roles of Enzymes That 'Cut and Paste' Plant Cell-Wall Polysaccharides", Journal of Experimental Botany, 64(12): 3519-3550, Published Online Aug. 14, 2013.

Jones "Cell Culture, Protoplast Isolation, and Cell Fusion of Cannabis Sativa L.; Evaluation of Chilling Preventative Chemicals and Quality Control of Bananas in the Tropics", Thesis, 50, 1970.

Lata et al. "High Frequency Plant Regeneration From Leaf Derived Callus of High Delta 9-Tetrahydrocannabinol Yielding Cannabis Sativa L.", Planta Medica, XP055332886, 76(14): 1629-1633, Published Online Mar. 30, 2010.

Lata et al. "In Vitro Mass Propagation of Cannabis Sativa L.: A Protocol Refinement Using Novel Aromatic Cytokinin Meta-Topolin and the Assessment of Eco-Physiological, Biochemical and Genetic Fidelity of Micropropagated Plants", Journal of Applied Research on Medicinal and Aromatic Plants, XP002792252, 3(1): Mar. 1, 2016. pp. 1-9.

MacKinnon et al. "Progress Towards Transformation of Fibre Hemp", Annual Report of the Scottish Crop Research Institute, XP055332880, 2001: 84-86, Jan. 2001.

Richez-Dumanois et al. "In Vitro Vegetative Propagation of Hemp (*Cannabis sativa* L.) Application for Preserving the Selected Clones", EDP Science, 6(5): 487-495, 1986. together with English Translation.

Richez-Dumanois et al. "Multiplication végétative in vitro du chanvre (*Cannabis sativa* L.). Application à la conserva-tion des clones sélectionnés", Agronomie, 6(5): 487-495, 1986.

Weber et al. "Improved Agrobacterium-Mediated Transformation of Sunflower (*Helianthus annuus* L.): Assessement of Macerating Enzymes and Sonication", Plant Cell Reports, 21:475-482, 2003.

Zhao et al. "Pollen Magnetofection for Genetic Modification With Magnetic Nanoparticles as Gene Carriers", Nature Plants, 3(12): 956-964, Published Online Nov. 27, 2017.

Communication Pursuant to Article 94(3) EPC Dated Nov. 23, 2022 From the European Patent Office Re. Application No. 19733152.3. (4 Pages).

Lata et al. "In Vitro Propagation of Cannabis Sativa L. and Evaluation of Regenerated Plants for Genetic Fidelity and Cannabinoids Content for Quality Assurance", Protocols for In Vitro Cultures and Secondary Metabolite Analysis of Aromatic and Medicinal Plants, 2nd Ed., Methods in Molecular Biology, XP055597325, 1391(Chap. 19): 275-288, Published Online Apr. 24, 2016.

Requisition by the Examiner Dated May 29, 2023 From the Innovation, Science and Economic Development Canada, Canadian Intellectual Property Office Re. Application No. 3,102,975. (5 pages).

\* cited by examiner

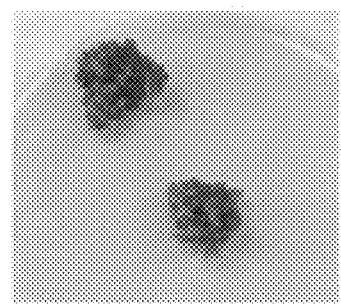
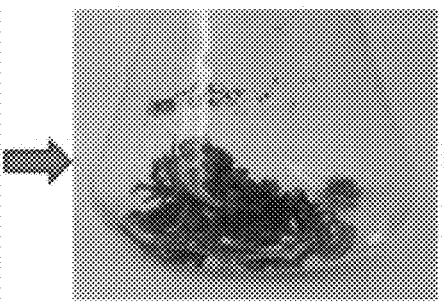
28 days in solid medium
21 days in liquid medium
28 days in solid medium
FIG. 3A
FIG. 3B
FIG. 3C
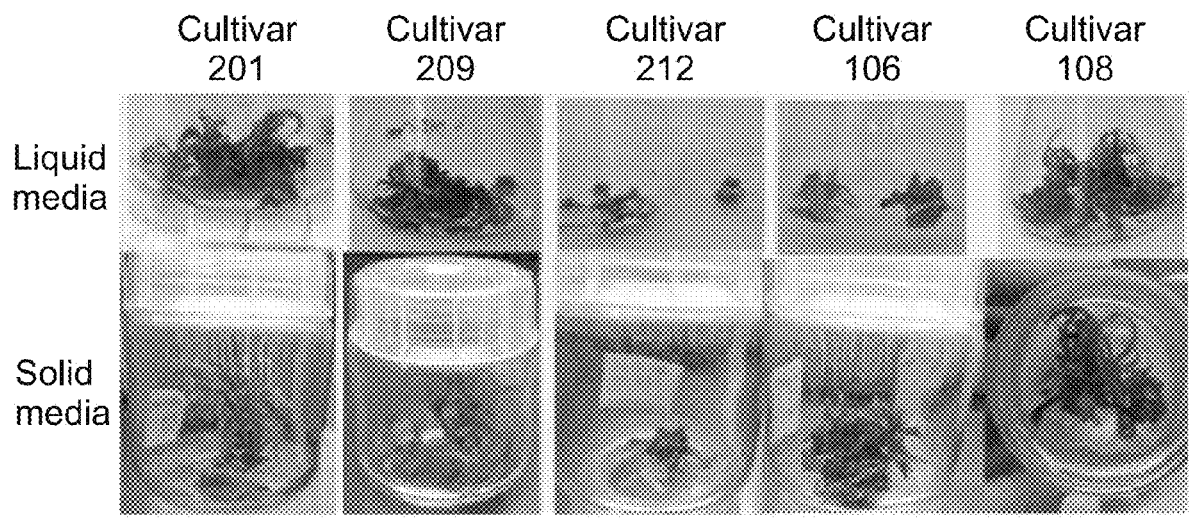
FIG. 4

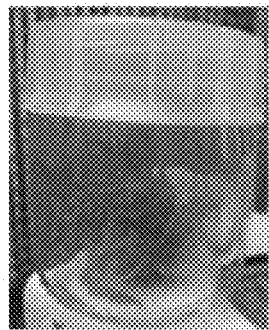 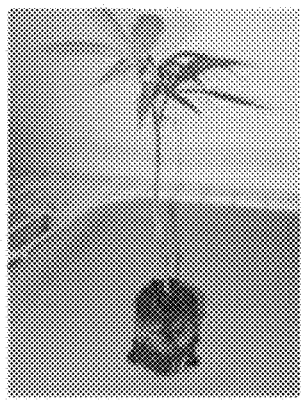 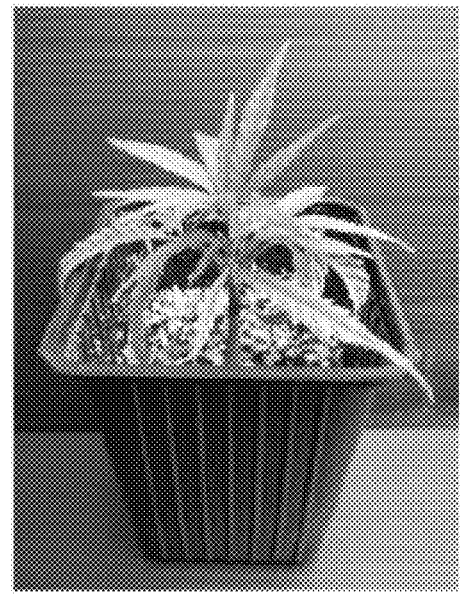
FIG. 5A  FIG. 5B  FIG. 5C
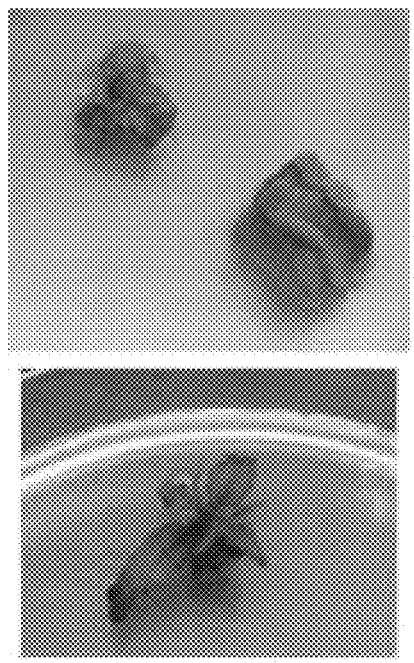 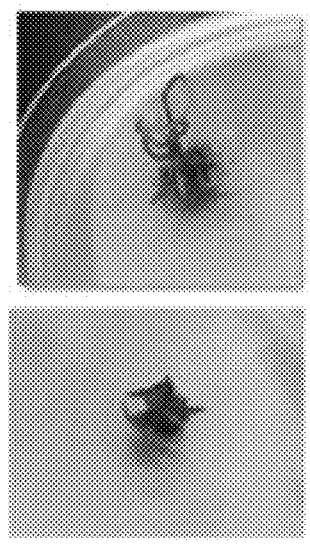 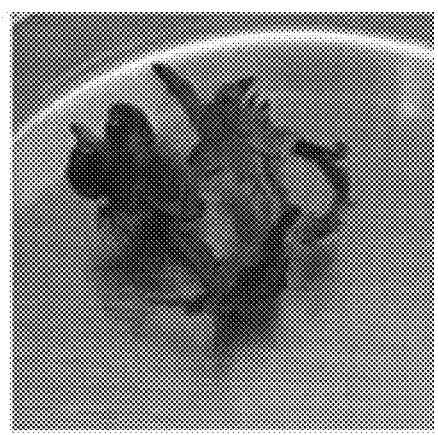
Regeneration from cotyledon  Regeneration from callus  Regeneration from leaves
FIG. 6

FIG. 12A  FIG. 12B
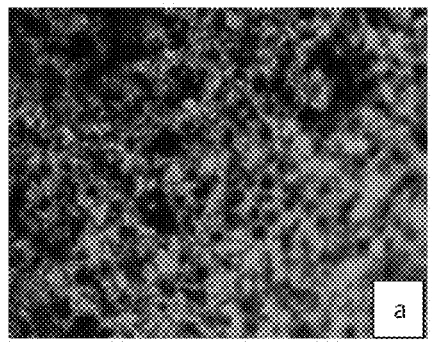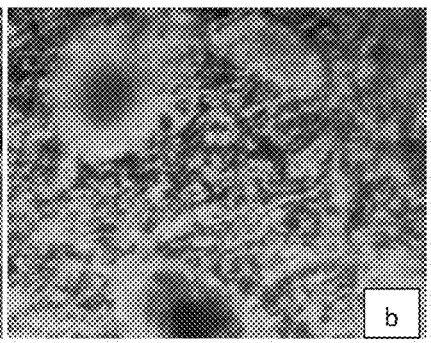
FIG. 13A  FIG. 13B  FIG. 13C
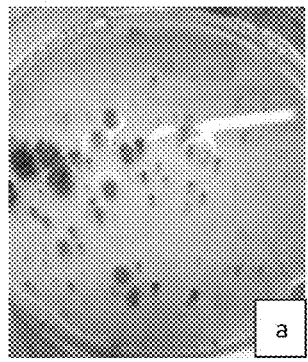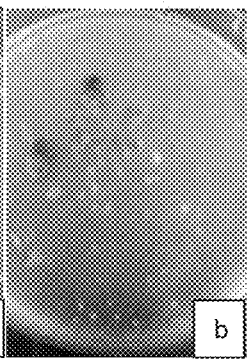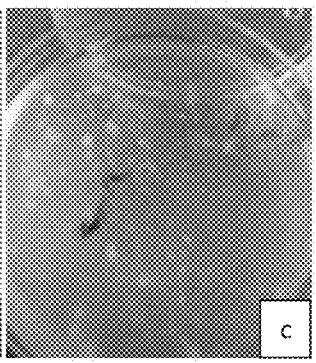

FIG. 16
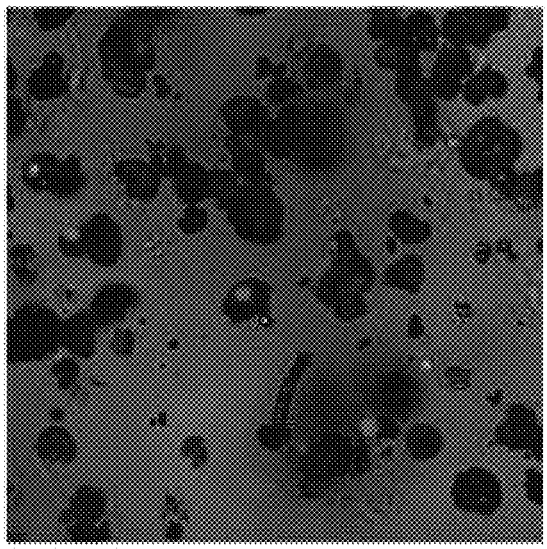
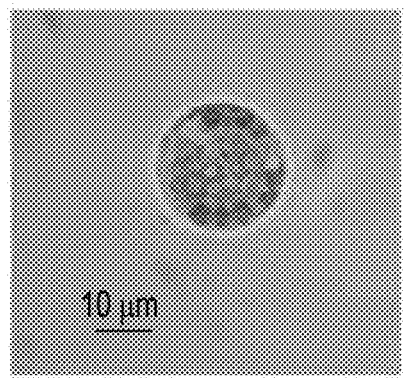 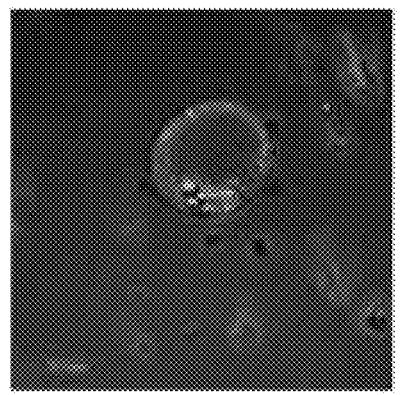
RFP expression in protoplast

FIG. 17A
FIG. 17B
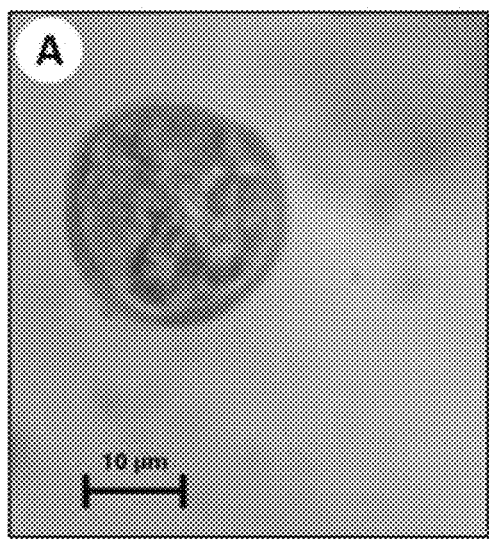
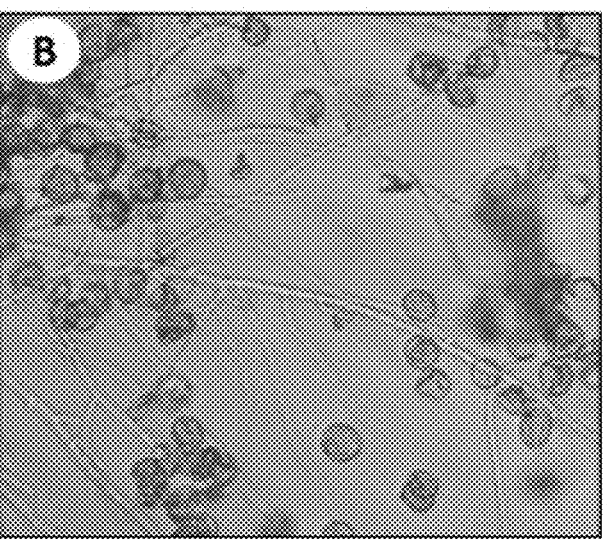
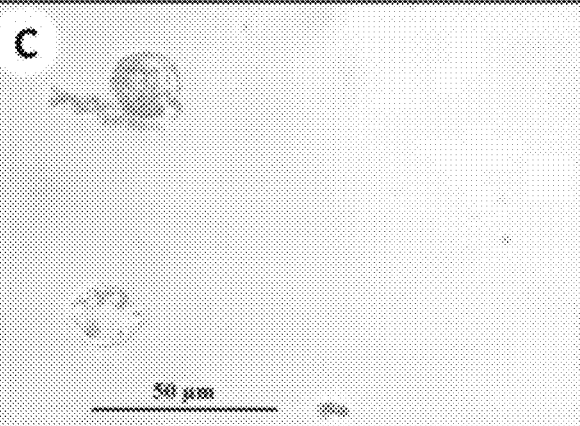
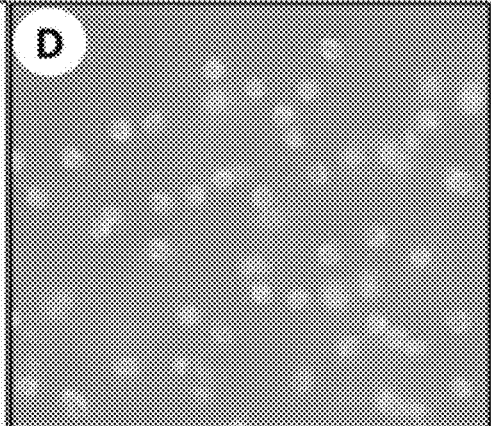
FIG. 17C
FIG. 17D

FIG. 18

*CsSERK1*

>csa_locus_12407_iso_1_len_2292_ver_2

```
GTTTGGGTTTGGGGTTGGGGTAGGAATTTTTTGTGATGTTGTGTTTGGGTGTGGCATACCATTTGGATCTAAGGTTTTTGGTTAC
TTAGACTAAATAGCAAGGGAGGAAATATGGAAAGGAAGAAGCTTTGGTGGTCTTCATTTTGCCTTTGGTTGATTTTGGTAGTTC
ATCCTTTATGGGTGATTATGGTATCTGCTAAT░░░GAAGGTGATGCCTTGCATAGTCTGAGGTCCAATTTACAGGATCCCAACAA
TGTTCTGCAGAGTTGGGATCCCACCCTTGTAAACCCGTGTACATGGTTTCATGTCACTTGCAACAATGATAATAGTGTGATAAGG
GTTGATCTTGGAAATGCAGCTTTGTCTGGTCAACTTGTTCCACAGCTTGGCCTTCTCAAGAATTTACAATATTTGGAACTTTACA
GTAATAACATTAGTGGAACAATTCCTAGTGATTTGGGGAATTTGACCAGCTTGGTTAGCTTGGATCTGTATTTGAATAGTTTTAC
TGGTCCTATCCCGGACACCTTGGGCAAGTTGTCAAAATTAAGATTTCTTCGGCTTAACAACAATAGTCTGACGGGTCCAATTCCT
ATGTCGTTGACCAACATCACCTCACTGCAAGTGCTGGATCTGTCAAATAACAAATTAACCGGAGAGGTTCCAGACAATGGCTCGT
TTTCTTTATTCACTCCCATCAGTTTTGCTAATAACTTAAATCTATGTGGCCCGGTTACTGGACGACCCTGCCCAGGATCCCCGCC
ATTTTCACCTCCTCCTCCTTTTGTCCCACCACCCCAATTTCAGTCCCAGGTGGAAATAGTGCGACTGGGGCTATTGCTGGTGGA
GTTGCTGCTGGTGCTGCTTTATTATTGCTGCTCCTGCTATTGCATTTGCTTGGTGGCGTCGAAGGAAGCCACAAGAATTTTTCT
TTGATGTACCCGCTGAGGAGGATCCTGAAGTTCATCTTGGGCAGCTTAAAAGGTTTTCGTTGCGAGAATTACAAGTGGCAACTGA
TAGTTTTAGCAACAAAAACATTCTGGGACGGGGTGGATTTGGTAAGGTCTACAAAGGTCGCCTTGCAGATGGTTCTTTGGTTGCT
GTAAAGAGACTGAAAGAAGAGCGTACACCTGGTGGCGAGTTGCAGTTTCAAACAGAAGTAGAGATGATCAGTATGGCTGTGCATC
GGAATCTTCTTCGATTACGTGGGTTCTGTATGACACCAACCAACTGAACGATTACTTGTTTATCCTTATATGGCTAATGGGAGTGTTGC
CTCATGCTTAAGAGAACGGCCGCCACACCAACTGCCTCTTGATTGGCCTACTAGGAAACGAATAGCATTGGGTTCTGCAAGGGGT
CTTTCGTATTTGCATGATCATTGCGATCCAAAAATTATTCATCGTGATGTGAAAGCTGCTAATATTTTGTTGGATGAGGAGTTTG
AAGCAGTTGTTGGAGATTTCGGTTTGGCTAAACTTATGGACTACAAGGACACTCATGTTACTACAGCTGTACGAGGCACAATCGG
GCATATTGCTCCAGAGTACCTCTCTACCGGGAAGTCTTCTGAGAAAACCGATGTGTTTGGCTATGGAATCATGCTTTTGGAATTA
ATTACTGGACAGAGAGCTTTTGATCTTGCTCGGCTTGCAAATGATGATGATGTCATGTTGCTCGACTGGGTGAAAGGACTACTGA
AAGAGAAGAAGTTGGAAATGCTGGTGGACCCCGATCTTCAAAAGAACTACATAGAATCCGAAGTAGAGCAGCTTATTCAGGTTGC
ACTGCTCTGCACACAAGGTTCTCCCATGGACCGACCAAAGATGTCAGAGGTGGTGAGAATGCTGCAAGGCGATGGCTTGGCCGAG
AGATGGGATGAATGGCAAAAAGTGGAAGTACTACGACAAGAAGTCGAACTAGCCCCTCATCCAAACTCAGACTGGATAGTAGACT
CAACCGAAAACTTGCATGCGGTCGAGTTATCTGGTCCGAGG░░░CCCTGGCACAATAGAAAGTGGAAGAAAAAGGGAATTTACTT
ACAACTTAATTTTTTTTAATTAATTATAATAGCTTTTTTTTCTTCTTCTTAATGACCATAATCTGATTAATGTCTCTTTGTAAGT
CCATTCTGCATTGTATTCGTTACATTTGTGCATATGAGAGTCGCATTGGTAAGGTGCAAATTTGTATTGTCTGCTGCAGTGTGAC
AAAAGCCATAGATGTTTTTATAATATATGAAGCTGTGGCAGTTTTTATCTTTTGTTCACTGCAGCAGACAATACAAATTTGC
```

*CsBBM*

>csa_locus_8084_iso_7_len_1661_ver_2

```
AATAATAATAATAATAATATT░░░AGTATTATTACTAATGATAGTAATCTCAGTTGCCAGCTGGAAGCGCCGCCGTCTGCGGTGG
CTCCGGTGTCGTCTAAGAAGACCGTTGACACTTTTGGTCAACGTACCTCTATATACCGTGGTGTTACTCGACATAGATGGACTGG
TAGATATGAAGCTCATTTGTGGGACAACAGTTGCCGAAGAGAAGGCCAGAGTAGAAAAGGGCGACAAGTTTTATTTGGGTGGATAT
GATAAAGAAGAAAAGGCAGCAAGAGCTTATGATTTGGCTGCCCTTAAGTACTGGGGTCCTACCACCACTACAAATTTTGCAGTGT
CTAATTACGAAAAGAATTAGAAGATATGACGAACATGACTAGGCAAGAATTCGTTGCTTCACTTCGAAGGAAAGTAGTGGATT
TTCTAGAGGAGCTTCAATATACAGAGGCGTCACAAGGCACCACCAACATGGTCGATGGCAGGCAAGAATTGGAAGAGTAGCAGGA
AACAAAGATCTCTACCTTGGCACCTTTAGCACACAAGAAGAAGCAGCCGAGGCATACGACATCGCGGCGATAAAATTCCGAGGCC
TAAACGCCGTAACAAACTTCGACATGAGCCGTTACGACGTTAAAAGCATAGCCAACTCTAATCTCCCCGTTGGAGGAATGTCAAA
CAACACCAAACTTTCCAAAACCTCACCCGAACGGGCGATTGACAACCTATCATGCCCGCTTCATCATCCCTCGTCGCCTTCTCC
TCCTCGGCCACCACCAACAACAACAACAACACCCCAACAACAACAACAACAAATGTCCTCCAATCTAAGCTTTACTCTTC
CCATCAAACAAGACCTAACAACAACGACAACATCGTCAACGGATTATTGGTCAAACATTTTCGGTTTCCAAAACCCTAACCCTAG
TAGTACTACTAGTACTACTCCTTCCTTATTGTTGGGCATAATAGTCACAACCTCTCGGCCACATCAACTAATGCAACAACAACT
ACAACAACAACAAGTAATGGAGGGTATTATGGTAATTTCATCGAGTCAATTCTAATAATAATAATAATAATACTAACTTGGGTT
ATGGATCAGGATTAAGTAGCTGGATTAGTAATAGTAATCATAATATTAACGGAGGGAGTAGTAATAGTAGTAATGTTCATAATCA
TCTTCATCATCATCATCTTCATGCGGAACAACCTAGTCTTTTCAAACACCAATATTCGGCATGGAA░░░TAA
TGATGATGATTTTTCTCGCACACTTGTTGGAAAACTACTGGCACGTGGGAATCTGTGGTGTTTGAATTTGCATGGAAAAGGGAGC
TAGGGTTGTTGTTGTTGTTATTGTAATAATAATAATAATATGGTGGAAACTGACAATATTCATCATAATATTATTTTTCATGAGA
GATGAGAATGTAGTAGTGAAATAGCTAGTACTAACTGAAGTTGGGTTCTTTTAGGGACCATGTTTTACTTTTTTATTATATTTT
TTGCTTTTTCTTTTTCCTTTAGTTTCATTACTAGATCTACTGACATTATTATTATTCTAGGTGTTAAGGAAAGGAATCCTTTTG
TAATCCTTAGTTTTTTTCATATATATTATATAAATGCACCTTCTTC
```

METHOD OF REGENERATING CANNABIS

RELATED APPLICATIONS

This application is a continuation of U.S. patent application Ser. No. 16/972,647 filed on Dec. 7, 2020, which is a National Phase of PCT Patent Application No. PCT/IL2019/050653 having International Filing Date of Jun. 6, 2019, which claims the benefit of priority under 35 USC § 119(e) of U.S. Provisional Patent Application No. 62/681,697 filed on Jun. 7, 2018. The contents of the above applications are all incorporated by reference as if fully set forth herein in their entirety.

SEQUENCE LISTING STATEMENT

The XML file, entitled 93275SequenceListing, created on Jul. 11, 2022, comprising 29,956 bytes, submitted concurrently with the filing of this application is incorporated herein by reference.

FIELD AND BACKGROUND OF THE INVENTION

The present invention, in some embodiments thereof, relates to methods of regenerating and transforming *cannabis*.

*Cannabis sativa* L. is an annual herb. It is among the earliest cultivated plants which originated in Central Asia. It is valued as a food, oil, fiber, medicinal and recreational drug source and, consequently, has been dispersed throughout the world. *Cannabis sativa* L. (marijuana) contains cannabinoids, a unique class of terpenophenolic compounds which accumulates mainly in glandular trichomes of the plant. Over 100 cannabinoids have been isolated from marijuana, the major biologically active compound being Δ9-tetrahydrocannabinol, commonly referred as THC.

The development of genetic transformation technology for plants has resulted in a great progress toward the genetic design of plants with enhanced production traits, such as herbicide, insect and disease resistance. Commercial cultivars of several transgenic plants have been released. The development of new *Cannabis* cultivars with improved traits could be further facilitated using biotechnological strategies. The dioecious life cycle of many *Cannabis* varieties complicates breeding efforts towards improvement of specific traits, such as resistance to pests and diseases. Development of a tissue culture system to regenerate *cannabis* plantlets and an *Agrobacterium* mediated transformation protocol would permit exploitation of a greater amount of genetic diversity for plant improvement and would facilitate clonal multiplication of plants with desirable traits.

There are only a small number of reports concerning tissue culture of *Cannabis*. Most of these studies were aimed at developing a cell culture system to obtain secondary metabolites, particularly the class of cannabinoids that are distinctive to the genus *Cannabis* (Turner et al., 1980). Callus cultures (Hemphill et al., 1978; Heitrich and Binder, 1982) and suspension cultures (Veliky and Genest, 1972; Itokawa et al., 1977; Hartsel et al., 1983; Loh et al., 1983; Braemer and Paris, 1987) have been established for extraction of secondary metabolites and biotransformation studies.

Methods to multiply *C. sativa* plants in-vitro via stimulation of axillary buds on nodal segments, or induction of adventitious buds in the shoot tips have been described (Lata et al., 2009 vitro Cell. *Dev. Biol. Plant* 45, 12-19. doi: 10.1007/s11627-008-9167-5; Wang et al., 2009 *Pak. J. Bot.* 41, 603-608). It was shown that micro-propagated plants are genetically stable; therefore the method is appropriate and useful for the clonal multiplication of this important crop (Lata et al., 2010 *Planta Med.* 76, 1629-1633. doi: 10.1055/s-0030-1249773; Lata et al. Journal of Applied Research on Medicinal and Aromatic Plants 3 (2016) 18-26).

A protocol has also been developed for the propagation of hemp via the synthetic seed technology. According to this procedure, axillary buds or nodal segments are encapsulated in calcium alginate beads (Lata et al., 2009 *Physiol. Mol. Biol. Plants* 15, 79-86. doi: 10.1007/s12298-009-0008-8, Lata 2011 *Biotechnol. Lett.* 33, 2503-2508. doi: 10.1007/s10529-011-0712-7), which can then be stored and subsequently used for clonal propagation of the plant. This system was shown to allow the growth of homogeneous and genetically stable *Cannabis* plants even after 6 months of storage (Lata et al., 2011, *Biotechnol. Lett.* 33, 2503-2508. doi: 10.1007/s10529-011-0712-7).

Organ regeneration, in particular shoots, can be quite cumbersome and therefore the screening of different plant growth regulator concentrations and combinations has to be carried out to find the right culture medium composition.

*Cannabis sativa* is a notorious recalcitrant plant to transformation, because the regeneration efficiencies are quite low (Slusarkiewicz-Jarzina et al., 2005 *Acta Biol. Cracov. Ser. Bot.* 47, 145-151).

Genome editing is a promising new technique for plant breeding. With designer nucleases called CRISPR-Cas9 mutations can be precisely directed to any gene of interest. Successful genome editing requires simple genetics (diploid) and the availability of a high-quality genomic DNA sequence. Following editing, the CRISPR-Cas genes should be removed, for example by crossing and selecting null-segregates that inherit the induced mutation. Crossing is not suitable for heterozygous crops like *Cannabis*, in which varieties are vegetatively propagated. Methods for transient expression in leaf protoplasts need to be developed.

Additional background art includes:

Zhao et al., 2017-*Nature plants,* 3(12): 956;

MacKinnon, L., McDougall, G., Azis, N., and Millam, S. (2001). "Progress towards transformation of fibre hemp," in *Annual Report of the Scottish Crop Research Institute* 2000/2001, eds W. H. Macfarlane Smith and T. D. Heilbronn (Dundee: SCRI Invergowrie), 84-86;

U.S. Patent Application Publication number: 20120311744;

SUMMARY OF THE INVENTION

According to an aspect of some embodiments of the present invention there is provided a method of in-vitro propagating *cannabis*, the method comprising:
 (a) culturing a *cannabis* plant part comprising a meristem on a solid culture medium so as to obtain an explant; and subsequently
 (b) subjecting the explant to a cell wall disrupting agent;
 (c) culturing the explant in a liquid medium; and optionally subsequently wherein steps (a)-(c) are effected for 1 to n times until emergence of leaves suitable for regeneration.

According to some embodiments of the invention, the method further comprises sterilizing the explant prior to (a).

According to some embodiments of the invention, the liquid medium comprises the cell wall disrupting agent.

According to some embodiments of the invention, the step (c) is performed while shaking.

According to some embodiments of the invention, step (a) is performed for 7-30 days.

According to some embodiments of the invention, step (c) is performed for 5-30 days.

According to some embodiments of the invention, the meristem is an apical meristem or an axillary meristem.

According to some embodiments of the invention, the explant comprising the meristem is of a stem.

According to some embodiments of the invention, the explant is from a seedling.

According to some embodiments of the invention, the explant is from a mature plant.

According to some embodiments of the invention, the method further comprises removing leaves and necrotic regions from the explant between steps (a) to (c).

According to some embodiments of the invention, the cell wall disrupting agent is selected from the group consisting of a chemical, an enzyme and a physical treatment.

According to some embodiments of the invention, the enzyme comprises a plurality of enzymes.

According to some embodiments of the invention, the enzyme is provided at a sub-lethal concentration.

According to some embodiments of the invention, the enzyme is selected from the group consisting of pectinase, cutinase and a combination thereof.

According to some embodiments of the invention, in the step (a), the solid medium is devoid of the cell wall disrupting agent.

According to some embodiments of the invention, the emergence of leaves suitable for regeneration is manifested by rooting and acclimatization According to an aspect of some embodiments of the present invention there is provided a regenerable *cannabis* explant obtainable according to the method as described herein.

According to an aspect of some embodiments of the present invention there is provided a method of *cannabis* regeneration in a tissue culture, the method comprising culturing regenerable *cannabis* explant in-vitro in a solid medium comprising at least one regeneration agent and a cell wall disrupting agent so as to regenerate *cannabis*.

According to an aspect of some embodiments of the present invention there is provided a method of in-vitro *cannabis* transformation, the method comprising, contacting a regenerable *cannabis* explants in-vitro with a polynucleotide encoding an expression product of interest and a cell wall disrupting agent.

According to some embodiments of the invention, the method further comprises wounding the leaves prior to contacting.

According to some embodiments of the invention, the transformation comprises a transient transformation.

According to some embodiments of the invention, the transformation comprises a stable transformation.

According to some embodiments of the invention, the contacting is effected by bombardment or *Agrobacterium*.

According to an aspect of some embodiments of the present invention there is provided a method of in planta *cannabis* regeneration, the method comprising:
 (a) removing, exposing and/or wounding a meristem of a *cannabis* tissue so as to obtain a meristem-depleted *cannabis* tissue; and
 (b) treating the meristem-depleted *cannabis* tissue with a composition comprising at least one plant hormone which allow for meristem regeneration;

According to an aspect of some embodiments of the present invention there is provided a method of in planta *cannabis* transformation, the method comprising:
 (a) removing, exposing and/or wounding a meristem of a *cannabis* tissue so as to obtain a meristem-depleted *cannabis* tissue; and
 (b) treating the meristem-depleted *cannabis* tissue with a composition comprising at least one plant hormone that allows plant regeneration and with a composition comprising a nucleic acid sequence encoding an expression product of interest.

According to some embodiments of the invention, the composition comprising the at least one plant hormone that allow plant regeneration and the composition comprising the nucleic acid sequence of interest are the same compositions.

According to some embodiments of the invention, the composition comprising at least one plant hormone that allow plant regeneration and the composition comprising the nucleic acid sequence of interest are different compositions.

According to some embodiments of the invention, treating with the composition comprising at least one plant hormone that allow plant regeneration and the composition comprising the nucleic acid sequence of interest is performed concomitantly.

According to some embodiments of the invention, treating with the composition comprising at least one plant hormone that allow plant regeneration and the composition comprising the nucleic acid sequence of interest is performed sequentially.

According to some embodiments of the invention, the sequentially is within an interval of 24-96 h.

According to some embodiments of the invention, the *cannabis* plant is a seedling.

According to some embodiments of the invention, the *cannabis* plant is a mature plant.

According to some embodiments of the invention, the mature plant comprises at least two nodes.

According to some embodiments of the invention, the exposing is effected while leaving a single leaf or cotyledon to allow photosynthesis.

According to some embodiments of the invention, the composition is formulated such that allows attachment of the composition to a surface of the meristem-depleted *cannabis* tissue.

According to some embodiments of the invention, at least one of the composition comprising at least one plant hormone and a composition comprising a nucleic acid sequence of interest comprises an emulsifier.

According to an aspect of some embodiments of the present invention there is provided a method of *cannabis* regeneration via somatic embryogenesis, the method comprising:
 (a) culturing a callus or a regenerable *cannabis* explant in a liquid culture while shaking till appearance of globular structures;
 (b) culturing the globular structures in a liquid culture while shaking till appearance of leaves.

According to some embodiments of the invention, step (a) is effected in the presence of CPPU; and wherein step (b) is effected in the presence of CPPU+TBD.

According to some embodiments of the invention, the step (a) is effected in the absence of TBD.

According to an aspect of some embodiments of the present invention there is provided a method of in-vitro *cannabis* transformation, the method comprising, contacting a leaf producible according to the method as described herein with a polynucleotide encoding an expression product of interest.

According to some embodiments of the invention, the polynucleotide is comprised in a formulation comprising *Agrobacterium* or PEG.

According to an aspect of some embodiments of the present invention there is provided a method of producing *cannabis* protoplasts, the method comprising, treating a *cannabis* tissue with macerozyme R-10 and mannitol, so as to obtain protoplasts.

According to some embodiments of the invention, the method further comprises treating with cellulose onzuka R-10 and/or hemicelluloses.

According to some embodiments of the invention, the macerozyme R-10 is provided at a concentration of 0.4-1.5%.

According to some embodiments of the invention, the hemicelluloses is provided at a concentration of 0.5-2%.

According to some embodiments of the invention, the onzuka R-10 provided at a concentration of 0.5-3%.

According to an aspect of some embodiments of the present invention there is provided protoplasts obtainable according to the method as described herein.

According to an aspect of some embodiments of the present invention there is provided a method of *cannabis* transformation, the method comprising contacting the protoplasts as described herein with a composition comprising a nucleic acid sequence encoding an expression product of interest.

According to an aspect of some embodiments of the present invention there is provided a method of *cannabis* transformation, the method comprising contacting pollen of a *cannabis* plant with particles comprising a nucleic acid sequence encoding an expression product of interest under a magnetic field that concentrates the particles and allows penetration of the nucleic acid sequence of interest into the pollen.

According to some embodiments of the invention, the pollen is used up to 12 hours post harvesting.

According to some embodiments of the invention, the *cannabis* is *Cannabis sativa*.

According to an aspect of some embodiments of the present invention there is provided a method of *cannabis* regeneration, the method comprising transforming an explants of the *cannabis* with a regenerating gene and allowing the tissue to regenerate.

According to some embodiments of the invention, the transforming is according to the method as described herein.

According to some embodiments of the invention, the regenerating gene comprises a nucleic acid sequence of CsBBM and CsSERK1 or a homolog of same.

According to an aspect of some embodiments of the present invention there is provided a transformed *cannabis* plant obtainable as described herein.

According to some embodiments of the invention, the nucleic acid sequence encoding an expression product of interest is selected from the group consisting of a genome editing agent, an RNA silencing agent, a regeneration agent, a gene conferring an agriculturally valuable agent and a modulator of *cannabis* metabolome.

According to an aspect of some embodiments of the present invention there is provided a method of breeding, the method comprising crossing the plant as described herein with another *cannabis* plant.

According to some embodiments of the invention, the method further comprises selecting for a phenotype of interest.

According to some embodiments of the invention, the phenotype comprises presence or absence of a transgene.

According to some embodiments of the invention, the phenotype of interest comprises an agriculturally valuable trait and/or a *cannabis* valuable trait.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 shows the establishment of *Cannabis* tissue culture. Ten different *cannabis* cultivars seedlings and shoot cuttings were sterilized and grown on ½ MS medium supplemented with 10 g/L sucrose, 5.5 g/L agar at a pH of 6.8 with different plant hormone combinations under light for 16 h per day. Most cultivars exhibited limited growth on solid media supplemented with different hormonal combinations.

FIG. 2 is a bar graph showing tissue culture response to various growth media. Growth rate was scored from 1 (growth arrest) to 5 (rapid growth).

FIGS. 3A-3C are images showing *Cannabis* plant propagation in tissue culture using "liquid treatment" according to the embodiment described in the Examples section. FIG. 3A—28 days old tissue culture in solid medium presents low growth and development. FIG. 3B—49 days old which is 21 days in the "liquid treatment" according to the embodiment described in the Examples section. FIG. 3C—The same plant after the "liquid treatment" (FIG. 3B), cultured in a solid medium;

FIG. 4 shows the results of a combined treatment with liquid media with sub-lethal doses of cuticle nicking enzymes and plant and surfactants;

FIGS. 5A-5C show rooting and acclimatization of *Cannabis* plants generated according to FIG. 4. FIG. 5A—In-vitro plant after solid-liquid-solid culturing with the nicking enzymes in liquid phase. FIG. 5B—Plants in rooting cylinders. FIG. 5C—Potted plants in the greenhouse one month after acclimatization (planting).

FIG. 6 is an image showing *Cannabis* regeneration from different plant tissues (leaves and calli from tissue culture, cotyledons from seeds).

FIG. 7 shows *cannabis* transformation of different plant tissues. Successful transformation of several *cannabis* cultivars using the uidA-intron and nptII genes. Efficient transient transformation of leaves, hypocotyls, callus and cotyledons of several *Cannabis* cultivars (upper panel). Positive PCR was shown in all tested clones (lower panel). 22 samples were tested.

FIGS. 8A-8F are images showing *Cannabis* seedlings in planta regeneration using the "regeneration paste" according to the embodiment described in the Examples section with appropriate plant hormone combinations. FIG. 8A. Seedling meristem—the striped line indicates the cutting, wounding place. FIG. 8B. Peeling and exposing the tissue between the cotyledon and stem. Note that there is no meristem hidden. Cutting start is indicated by arrowheads, FIG. 8C. Scanning electron micrograph of the cut seedling, FIG. 8D. Stereoscope micrograph of the cut seedling, FIGS. 8E-8F. Regenerating shoots, arrowhead indicates the remains of the removed stem.

FIGS. 12A-12B show a liquid culture (FIG. 12A) and globular stage embryos (FIG. 12B) that was initiated on B5 media, supplemented with 10 mg/l CPPU.

FIGS. 13A-13C show plant regeneration on liquid media. Suspension culture with globular stage embryos (FIG. 13A) callus formation (FIG. 13B) and plant regeneration (FIG. 13C) was initiated on B5 media, supplemented with 10 mg/l CBD-CPPU.

FIG. 16 shows protoplast transformation using the RFP gene.

FIGS. 17A-17D are images of optical microscopy of *Cannabis* pollen. FIG. 17A—Pollen grain stained with Safranine O. FIG. 17B—Germination of pollen grain after 18 h. (FIG. 17C—Transformed pollen grain expressing the exogenous reporter GUS gene. FIG. 17D—No transformation staining control.

FIG. 18 shows the Sequences of the CsBBM and CsSERK1 genes (SEQ ID NOs: 2 and 1, respectively). Transcript sequences were obtained from the database available at www(dot)medicinalplantgenomics(dot)msu(dot)edu/index(dot)shtml. Start and stop codons are highlighted in yellow.

Figure 19:
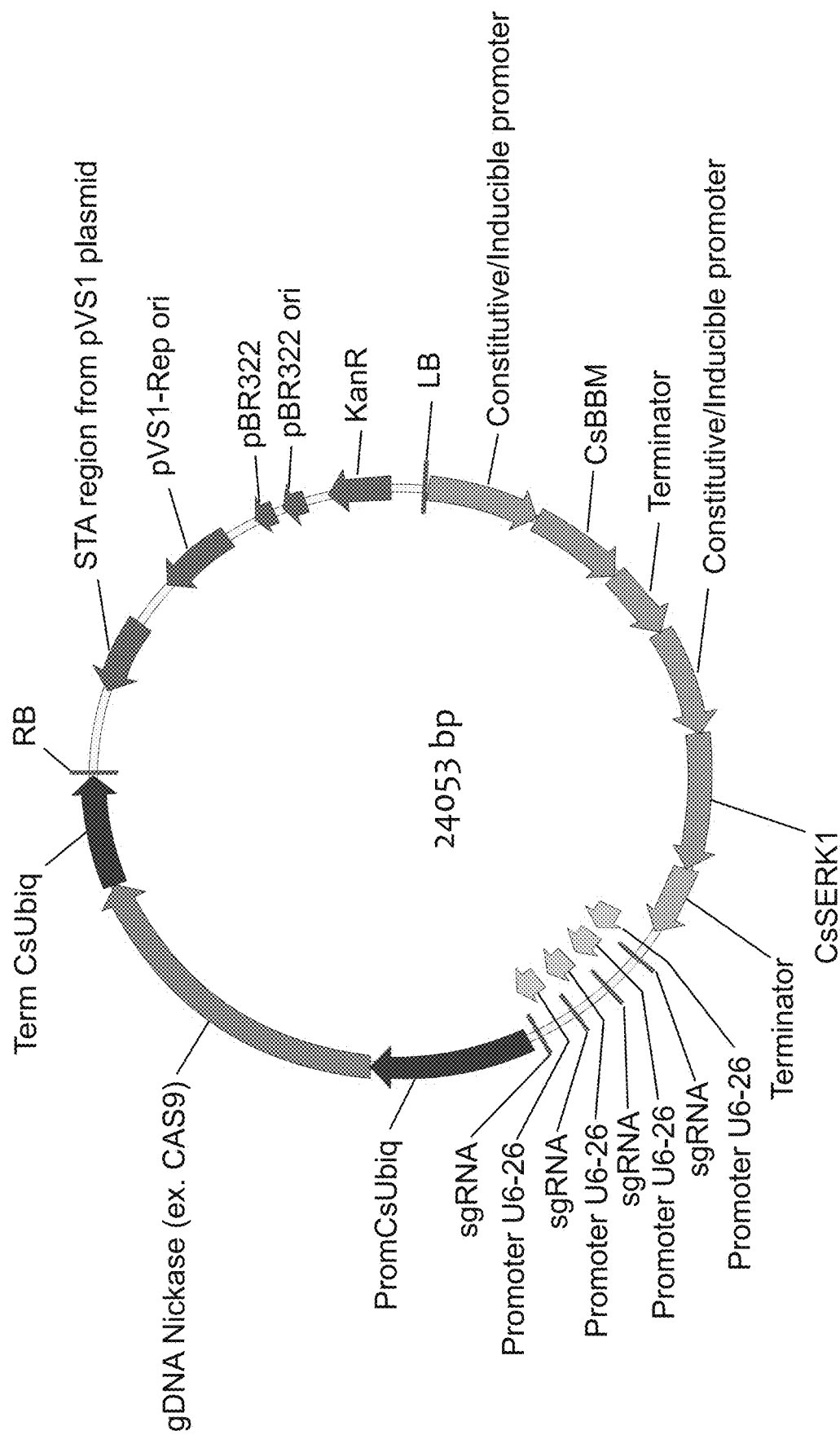

FIG. 19 is a map of the plasmid used to induce somatic embryogenesis and genome editing in *Cannabis* plants. The CAS9 is under the control of the CsUBIQUITIN10 promoter (SEQ ID NO: 11); the CsBBM, and CsSERK1 genes are under the same CsUBIQUITIN10 promoter (SEQ ID NO: 11).

DESCRIPTION OF SPECIFIC EMBODIMENTS OF THE INVENTION

The present invention, in some embodiments thereof, relates to methods of regenerating and transforming *cannabis*.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

*Cannabis* is currently witnessing a revival because of its rich repertoire of phytochemicals, its fibers and its agricultural features, namely resistance to drought and pests, well-developed root system preventing soil erosion and lower water requirement with respect to other crops, e.g., cotton. *Cannabis* varieties producing oil, biomass and phytochemicals are currently cultivated. The availability of genome sequences greatly helps molecular studies on this important crop (van Bakel et al., 2011, The draft genome and transcriptome of *Cannabis sativa. Genome Biol.* 12:R-102. doi: 10.1 186/gb-2011-12-10-R-102). In addition, the scientific community is very much interested in harnessing *Cannabis* pharmacological power.

However, to date, there are only a small number of reports concerning tissue culture of *Cannabis*. Most of these studies were aimed at developing a cell culture system to obtain secondary metabolites, particularly the class of cannabinoids that are distinctive to the genus *Cannabis* (Turner et al., 1980). Callus cultures (Hemphill et al., 1978; Heitrich and Binder, 1982) and suspension cultures (Veliky and Genest, 1972; Itokawa et al., 1977; Hartsel et al., 1983; Loh et al., 1983; Braemer and Paris, 1987) have been established for extraction of secondary metabolites and biotransformation studies. However transgenic cultivars of *Cannabis* plants have not yet been released and research has not demonstrated that this technology can be applied.

Whilst reducing embodiments of the invention to practice, the present inventors were able to regenerate *cannabis* in culture and to develop protocols for plant transformation either on tissue explants, pollen or even in planta.

These protocols can be exploited towards genetic manipulation of this crop plant by way of over-expression, genome editing or silencing which can benefit the entire *cannabis* industry.

The term "'plant" as used herein encompasses whole plants, a grafted plant, ancestors and progeny of the plants and plant parts, including seeds, shoots, stems, roots (including tubers), rootstock, scion, and plant cells, tissues and organs. The plant may be in any form including suspension cultures, embryos, meristematic regions, callus tissue, leaves, gametophytes, sporophytes, pollen, and microspores.

The terms "*cannabis*" refers to the genus which includes all different species including *Cannabis sativa, Cannabis indica* and *Cannabis ruderalis* as well as wild *Cannabis*.

*Cannabis* is diploid, having a chromosome complement of 2n=20, although polyploid individuals have been artificially produced and are also contemplated herein. The first genome sequence of *Cannabis*, which is estimated to be 820 Mb in size, was published in 2011 by a team of Canadian scientists (van Bakel et al, supra).

All known strains of *Cannabis* are wind-pollinated and the fruit is an achene. Most strains of *Cannabis* are short day plants, with the possible exception of *C. sativa* subsp. *sativa* var. *spontanea* (=*C. ruderalis*), which is commonly described as "auto-flowering" and may be day-neutral.

According to a specific embodiment, the plant is of *C. sativa*.

*Cannabis* has long been used for drug and industrial purposes: fiber (hemp), for seed and seed oils, extracts for medicinal purposes, and as a recreational drug. The selected genetic background (e.g., cultivar) depends on the future use. Industrial hemp products are made from *Cannabis* plants selected to produce an abundance of fiber. Some *Cannabis* strains have been bred to produce minimal levels of THC, the principal psychoactive constituent responsible for the psychoactivity associated with marijuana. Marijuana has historically consisted of the dried flowers of *Cannabis* plants selectively bred to produce high levels of THC and other psychoactive cannabinoids. Various extracts including hashish and hash oil are also produced from the plant.

Thus, for example, a CBD rich strain can be selected from a group consisting of Golan, Avidekel, Fedora 17, ACDC, and any combination thereof; or wherein said *cannabis* plant is a THC rich strain; said THC rich strain is selected from a group consisting of Everest, Black Destroyer, Critical Neville Haze, Mataro Blue, LSD OG Kush, Pineapple Chunk, Blue Monster Holk, Y Griega, Satori, Tutankhamon, and any combination thereof.

Some additional varieties are provided infra in Example 1 of the Examples section which follows (e.g., WON21, Pinola, Goodrich, Glory, Lemon Haze, Jack herer, Lemon Haze Bnn., Cheese and SLH.).

The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

The term "variety" is interchangeable with "cultivar".

As mentioned, embodiments of the invention relate to *cannabis* transformation and plant regeneration. It will be appreciated that the process of tissue transformation is dependent on the ability of the plant to regenerate. The protocol of regeneration can be selected from in-vitro regeneration and in planta regeneration.

As used herein "regeneration" or "regenerating" refers to the development of a whole plant from somatic cells e.g., in tissue culture (in-vitro) or in planta.

As used herein "regenerable" refers to the ability to develop into a whole plant in-vitro.

According to a specific embodiment, the regeneration efficiency using embodiments of the invention is at least 50% (regenerants from the source tissue or organ).

According to a specific embodiment, the regeneration efficiency using embodiments of the invention is at least 60%.

According to a specific embodiment, the regeneration efficiency using embodiments of the invention is at least 70%.

According to a specific embodiment, the regeneration efficiency using embodiments of the invention is at least 80%.

According to a specific embodiment, the regeneration efficiency using embodiments of the invention is at least 90%.

According to a specific embodiment, the transformation efficiency using embodiments of the invention is at least 60% (e.g., in transient transformation).

According to a specific embodiment, the transformation efficiency using embodiments of the invention is at least 70% (e.g., in transient transformation).

According to a specific embodiment, the transformation efficiency using embodiments of the invention is at least 80% (e.g., in transient transformation).

According to a specific embodiment, the transformation efficiency using embodiments of the invention is at least 90% (e.g., in transient transformation).

According to a specific embodiment, the transformation efficiency using embodiments of the invention is at least 1% (e.g., in stable transformation).

According to a specific embodiment, the transformation efficiency using embodiments of the invention is at least 2% (e.g., in stable transformation).

According to a specific embodiment, the transformation efficiency using embodiments of the invention is at least 3% (e.g., in stable transformation).

According to a specific embodiment, the transformation efficiency using embodiments of the invention is at least 5% (e.g., in stable transformation).

A common mode of plant regeneration both in planta and in-vitro is de novo organogenesis, in which plant cuttings or explants first form ectopic apical meristems and subsequently develop shoots and roots. Meristems are specialized plant tissues where new cells, tissues and organs are generated through cell division and differentiation. Plants can also regenerate through somatic embryogenesis in-vitro, whereby isolated protoplasts or cells first develop cellular structures similar to zygotic embryos and subsequently generate whole plant bodies, as contemplated herein and further described hereinbelow. Both of these regeneration processes occur either directly from parental tissues (e.g., leaves, stems, roots) or indirectly via the formation of a callus.

An in-vitro regeneration protocol may first be preceded by a step of clonal propagation for large scale, reproducible, uniform (±10%) production of plant material/explant.

As used herein a "regenerable explant" refers to regenerable cells (*cannabis* cells) for use in tissue culture for transforming and regenerating *Cannabis*. A tissue culture which includes regenerable cells is capable of regenerating plants having the physiological and morphological characteristics of *Cannabis* (transformed or no-transformed).

According to a specific embodiment "transformed" refers to transgenic.

According to another embodiment, "transformed" refers to non-transgenic, such as by means of genome-editing.

The regenerable cells in such tissue cultures can be from embryos, protoplasts, meristematic cells, callus, pollen, leaves, anthers, pistils, roots, root tips, flowers, seeds, pods, bolls, buds, stems, or the like.

According to a specific embodiment, the regenerable cells are suitable for applying a regeneration protocol.

The present inventors have realized through a series of laborious experiments, that the key factor for successful in-vitro propagation (as determined by time dependent biomass accumulation) is an initial growth on a solid medium, transfer to a liquid medium and transfer back to a solid medium, so as to allow the explants to exploit the substances in the media. This, combined with a treatment with a cell wall disrupting agent is pertinent to the success of clonal propagation.

Thus, according to an aspect of the invention there is provided a method of in-vitro propagating *cannabis*, the method comprising:
(a) culturing a *cannabis* plant part comprising a meristem on a solid culture medium so as to obtain an explant; and subsequently
(b) subjecting the explant to a cell wall disrupting agent;
(c) culturing the explant in a liquid medium; and optionally wherein steps (a)-(c) are effected for 1 to n times until emergence of leaves suitable for regeneration.

As used herein "in-vitro propagation" or "plant micropropagation" refers to an integrated process in which cells, tissues or organs of a selected plant are isolated, surface sterilized, and incubated in a growth-promoting aseptic environment to produce many clone plantlets (Altman, 2000, Spier, R. E. Encyclopedia of Cell Technology. New York: John Wiley & Sons, 916-929).

Thus, somatic cells, under appropriate conditions, can differentiate to a whole plant.

According to a specific embodiment, the process of clonal propagation is done under aseptic conditions.

According to a specific embodiment, the plant part taken to the tissue culture is sterilized prior to initiation of culturing.

For instance, the plant part is washed under abundant water flow (e.g., for 2 hours) followed by alcohol treatment (e.g., 70% ethanol) and optionally NaClO (e.g., 1.5%) that may be repeated as needed.

Thus, a *cannabis* plant part comprising a meristem is cultured on a solid culture medium so as to obtain an explant.

As used herein "meristem" refers to a plant tissue containing undifferentiated cells (meristematic cells), found in zones of the plant where growth can take place. Meristematic cells give rise to various organs of the plant and keep the plant growing. There are three types of meristematic tissues: apical (at the tips), intercalary (in the middle) and lateral (axial, at the sides).

According to a specific embodiment, the meristem is an apical or an axillary meristem.

According to a specific embodiment, the plant part is of a stem, e.g., shoot tips or axillary buds.

According to a specific embodiment, the plant part comprises both apical and axillary meristems.

According to a specific embodiment, the plant part comprises a root meristem.

According to a specific embodiment, the plant part comprises a root tip.

A plant part and a tissue may be interchangeable herein.

Such a tissue can be taken from a mature plant or a seedling e.g., having two true leaves that are then cut from the roots (a seedling may be more responsive than a mature plant) due to different levels of plant hormones present in the plants. The present inventors were able to show clonal propagation for both options (see Example 1).

According to a specific embodiment, the plant part comprises a nodal segment.

Typically, the medium used for clonal propagation (or regeneration or transformation) is a basal medium like white medium, Nitsch and Nitsch medium, B5 medium and Gamborf medium.

According to a specific embodiment, the medium is Murashige and Skoog (1962) (MS medium).

The strength of the medium or combination of media can be optimized for the protocol (e.g., propagation, regeneration or transformation).

According to a specific embodiment, the medium is ½ MS medium supplemented with sucrose at a pH of 6.8.

According to a specific embodiment, the carbon source is at a concentration of 1-4%.

According to a specific embodiment, the pH is 5.4-7.2.

Measures should be taken to supplement the medium with an appropriate mineral nutrition and carbon source (e.g., sucrose, glucose, maltose and galactose as well as the sugar-alcohols glycerol and sorbitol). The carbohydrates added to the culture medium supply energy for the metabolism. The addition of a carbon source in any nutrition medium is essential for in-vitro growth and development because photosynthesis in culture is typically insufficient.

Culture media can be classified as liquid or solid. The liquid media have the advantage of faster and cheaper propagation than the solid ones. However, a serious disadvantage of using liquid in for clonal propagation is that shoot (stems), which are perpetually submerged in liquid cultures may become hyperhydric and hence cannot undergo clonal propagation.

According to a specific embodiment, the medium is % MS medium supplemented with sucrose and hormone combinations.

The present inventors have found that for successful clonal propagation the explants require a first culturing period on a solid phase followed by liquid culturing and return to the solid phase.

Thus, a first stage of solid medium culturing is effected for 7-30 days (e.g., 21 days) or as long as the explant benefits from the solid culture and can absorb the nutrients/carbon source from the medium. The gelling agent that may be used to solidify the culture may change. Typically used are Agar and Gelrite. As the concentration of the gelling agent e.g., Agar may affect the development (e.g., root) the concentration is up to 1% e.g., Agar is 0.7%-1.0% w/w (e.g., 0.8%).

In order to improve the absorption of carbon source, minerals or other factors (e.g., regeneration agents, transformation agents etc. as further described hereinbelow), the explants may be treated with a cell wall disrupting agent. This can be performed at any step of the culturing e.g., during culturing on the solid phase and/or at the liquid phase.

According to a specific embodiment, the cell wall disrupting agent is present only at the liquid culture phase (i.e., absent from the solid medium).

As used herein "a cell wall disrupting agent" refers to a chemical, biological or physical treatment of the explant that results in damage to the cell wall but not affecting cell viability either due to degradation, hydrolysis of the polymers e.g., polyesters of the cuticle and/or suberin layers or mechanical breakdown of the cell wall.

Examples of such enzymes can be found in The Journal of Experimental Botany, Vol. 64, No. 12, pp. 3519-3550, 2013 doi:10.1093/jxb/ert201; Darwin Review Biochemistry and physiological roles of enzymes that 'cut and paste' plant cell-wall polysaccharides; and Catalysts of plant cell wall loosening, [Daniel J. Cosgrove 2016, which describe enzymes and other proteins e.g., expansions, that can be used in cell wall disruption.

These include, but are not limited expansions, endoglucanases, endotransglucosylases as well as, cutinase, pectin methyesterases and pectin modifying enzymes. From the whole range of CAZy groups, approximately 22 families are associated with enzymes that postsynthetically modify the plant cell wall. Plant glycosidases are mostly grouped in GH families 1, 2, 3, 27, 29, 31, 35, 36, 38, 51, and 95, while plant glycanases fall into GH families 2, 5, 9, 10, 16, 17, 28, and 81.

The cell wall disrupting agent may therefore be present in the liquid culture medium, the solid culture medium [towards the end of culturing on a solid medium i.e., not from the initiation of step (a)] or the explants may be taken out of the culture and treated with the cell wall disrupting agent before transfer to the liquid medium.

According to a specific embodiment, the treatment with the cell wall disrupting agent is (e.g., only) at the liquid phase.

According to a specific embodiment, the biological treatment comprises enzymes (e.g., "cuticle nicking enzymes").

Measures are taken to use the cell wall disrupting agent at sub-lethal dose/concentration i.e., less than lethal, but sufficiently high to disrupt the cell wall. Damage to the cell wall can be determined using various means including visual detection using a light microscope. Cell viability should be determined as well (e.g., staining, FACS etc.).

According to a specific embodiment, the enzymes are a fungal mix of pectin and cutinase enzymes.

As used herein, a cutinase (EC 3.1.1.74) is an enzyme that catalyzes the chemical reaction cutin+$H_2O$ cutin monomers.

According to a specific embodiment, the enzyme is a pectic enzyme e.g., pectin lyase (EC 4.2.2.10) which catalyzes the eliminative cleavage of (1-4)-α-D-galacturonan methyl ester to give oligosaccharides with 4-deoxy-6-O-methyl-α-D-galact-4-enuronosyl groups at their non-reducing ends.

Enzymes are available from commercial vendors e.g., BSG HandCraft Liquid Pectic Enzyme; Cutinase (Sigma, Ferdinand Maria Quincy). It will be appreciated that a single cell wall disrupting agent can be used, however combinations of 2, 3, 4, or more agents can be used (of the same or different types i.e., biological, chemical and physical).

According to a specific embodiment, the enzymes used include a pectic enzyme and a cutinase. As shown in Examples 2, the combination of the two enzymes increases explants growth rate in culture.

Accordingly, cutinase is available as a fungal mix of pectin and cutinase enzymes that is commercially available such as from BSG HandCraft Liquid Pectic Enzyme; Cutinase—Sigma, Ferdinand Maria Quincy.

At the liquid stage (which is a discrete stage from the solid medium culturing stage) the same base medium, carbohydrates and/or minerals can be used except that the polymerizing agent (e.g., agar) is absent. However, different media and/or supplements can be used as well.

Culturing in the liquid medium may be effected for 5-30 days (e.g., 21 days).

According to a specific embodiment, culturing is effected while shaking the container in which the explant is placed (in the liquid medium). There are numerous agitation methods including orbital, horizontal orbital shaking with limited amount of liquid.

Shaking prevents covering the whole explant with the medium during culturing at the liquid phase.

At any stage from the initiation of culturing (a-c), leaves (i.e., differentiated structures) and necrotic regions that can't regenerate are removed.

Additional agents that can be included in the culture (be it the solid phase, liquid phase, or all phases) include, but are not limited to, plant hormones, enzymes, vitamins, carbohydrates and minerals.

As mentioned, optionally, after culturing in the liquid medium the explant is transferred to culturing under solid conditions, for 20-45 days, and the whole process i.e., liquid, solid may be repeated for n number of times (e.g., 2, 3, 4, 5 or more times).

According to a specific embodiment, transfer from a solid to a liquid medium is taking place every 3-4 weeks, which significantly improves the growth and development.

Different strains may require different time periods for the propagation, generally requiring between 50 to 100 days. Culturing may be terminated once leaves suitable for regeneration emerge. According to a specific embodiment, such leaves are up to 48 days old (e.g., 21-48 days counting from transfer of the culture from liquid to solid), having up to about 0.5 cm width of surface area and optionally can be easily wounded such as with a scalpel or as further described hereinbelow.

The ability to regenerate can be determined using methods which are well known in the art e.g., rooting and acclimatization.

Elongation and root induction or development (rooting phase): This phase is designed to induce the establishment of fully developed plantlets. It is the last period in-vitro before transferring the plantlets to ex vitro conditions. Root induction is typically effected on a root induction solid medium in the presence of IBA and optionally other ingredients such as thiamine and possibly myo-inositol and/or charcoal. Rooting is much affected by the salt concentration in the medium. Also, the presence of auxins (e.g., IBA, IAA, NAA) at this stage is important as opposed to cytokinins. At rooting, it is important to balance the humidity required for rooting and the plant sensitivity to humidity. Under such considerations it is possible to lower the amount of the gelling agent (e.g., agar), add desiccating agents (e.g., silicone balls) and aerating the culture dishes. The use of gibberellins in the rooting medium may reduce or prevent the formation of adventitious roots and shoots, although it can stimulate root formation when present in low concentrations.

Transfer to ex vitro condition is also termed as "acclimatization". Acclimatization is defined as the climatic or environmental adaptation of an organism, especially a plant that has been moved to a new environment (Kozai and Zobayed, 2003 www(dot)doi(dot)org/10(dot)1002/0471250570(dot)spi001). Measures are taken to protect the regenerated explants from dehydration, which is typically done by graded lowering of the humidity by stepwise transferring from a greenhouse or tunnel (e.g., covered with a polyethylene sheet) to partial covering to no covering at all.

An example of a rooting and acclimatization protocol is provided in Example 1 which follows.

The results may be evaluated several weeks after assay initiation (e.g., 3-5 weeks).

The skilled artisan would take into consideration other parameters during culturing. These include, but are not limited to, gas exchange and relative air humidity inside the culture vessel.

The culture vessel is typically a closed system but some gas exchange may occur dependent on the vessel. The use of closures with filters or vented vessels which allow gas exchange may increase the photosynthetic capacity, the multiplication rate and the survival of plants at the acclimatization stage.

According to a specific embodiment, the relative humidity in the culture (i.e., culture vessel) is 90%. The temperature and light regimen employed for regeneration are known to the skilled artisan and typically including long day (e.g., 16 h) at 24° C.

Also contemplated herein is a regenerable *cannabis* explant obtainable according to the method described herein. It will be appreciated that the process of clonal propagation does not form a callus.

Once any regenerable *cannabis* explant is available (e.g., such as by the clonal propagation method described herein), it can be subjected to regeneration.

Thus, according to an aspect of the invention there is provided a method of *cannabis* regeneration in a tissue culture, the method comprising culturing a regenerable *cannabis* explant in a solid medium comprising at least one regeneration agent and a cell wall disrupting agent so as to regenerate *cannabis*.

The regenerable *cannabis* explants can be a product of the clonal propagation as described above. Also contemplated are germinated seeds, including cotyledons, leaves hypocotyls; alternatively, calli.

Regeneration protocols are known in the art.

Basically, in addition to a basal salt mixture the medium comprises at least one auxin, at least one cytokinin and optionally at least one gibberellin. Typically, the basal salt mixture used is half strength MS (Murashige and Skoog) medium, the auxin is indol-3-butyric acid (IBA), the cytokinin is 6-benzylaminopurine (BA) the gibberellic acid is $GA_3$. The medium typically further comprises as a carbon source. The medium further comprises, vitamins, myoinositol and thiamine-HCl and the pH of the medium is kept in the range of from about 4.5 to about 6.5 (e.g., 5.5-5.9).

The cultures are exposed to a cool fluorescent light in a photoperiod of 16 h of light and 8 h dark, at 25° C. Typically, the light intensity is in the range of between 40-70 µmol/m²s. Under these conditions (the propagation medium and the light regime) elongation of the micropropagating shoots and the formation of leaves from the shoot buds occur within about 2-4 weeks.

The medium for each strain can be further adjusted according to the strain's needs such as with cytokinins (e.g., TDZ, ZEATIN, NAA), activated charcoal, phloroglucinol, concentrations of GA/auxion cytokinin etc.

According to a specific embodiment, the regeneration is effected in line with the protocols listed in Example 2 of the Examples section which follows.

Regeneration from leaves can be done from 3 to 4 weeks old plants by placing the leaves on regeneration medium with the cell wall disrupting agent, as described. The cultures are kept for a number of days (e.g., 7 days) in low light intensity (e.g., 2.5 mmol/m2 s) followed by exposure to high light intensity (e.g., 40 mmol/m2 s) at room temperature (e.g., 25° C.), in a 16/8 h photoperiod. Leaf explants can be examined after 14 and 21 days and the percentage of explant producing shoots is determined.

Regeneration from cotyledon can be done as follows: Seeds are disinfected and put in a culture medium. Seeds are germinated (e.g., in the dark for 2 d and thereafter transferred to light). Cotyledons from large seedlings that contain two true leaves are cut and placed on a regeneration medium with the cell wall disrupting agent. The cultures are kept in high light intensity (e.g., 40 mmol/m2 s) at room temperature (e.g., 25° C.), in a 16/8 h photoperiod.

Callus is induced such as by the following protocol. 21 days old tissue culture is placed on a PR12 solid medium (MS, 2% sucrose, 2 mg/l BA, 1 mg/l GA3, 0.8 sigma agar, pH 5.8) to encourage the creation of callus. Two weeks later, calli are placed on a regeneration medium with the cell wall disrupting agent [e.g., Murashige and Skoog (MS) medium salt mixture, containing 0.05-5.0 µM thidiazuron, supplemented with 100 mg/l myo-inositol, 1 mg/l thiamine-HCl, 2% sucrose (w/v) at pH 5.7, with 5 ml pectic enzymes reaction mixture (0.25 ml 10% enzyme, 0.25 ml 200 mM Tris-HCl)]. The cultures are kept in high light intensity (40 mmol/m2 s) at 25 8 C, in a 16/8 h photoperiod.

The regeneration can be prior to, concomitantly with, or following DNA transformation.

Thus, according to an aspect there is provided a method of in-vitro *cannabis* transformation, the method comprising, contacting a regenerable *cannabis* explant with a polynucleotide encoding an expression product of interest and a cell wall disrupting agent.

Thus, for regeneration and transformation the use of a cell wall disrupting agent as described above is contemplated.

It will be appreciated that additional wounding the explant (e.g., leaves) may improve the efficiency when done prior to the contacting with the polynucleotide.

Wounding induces numerous cellular responses including the production of plant hormones, loss of cell to cell communication and disruption of long distance signaling. It is suggested that the AP2/ERF-type transcriptional regulator WIND1 and its homolog WIND2, WIND3 or AIND4 are induced upon wounding and promote callus formation at cut sites.

Wounding can be effected physically e.g., by the use of a scalpel or a sandpaper, which scratches the plant surface.

As mentioned, the transformation introduces a polynucleotide encoding an expression product of interest.

As used herein "expression product" refers to an RNA or protein (also referred to herein as "polypeptide").

According to a specific embodiment, the expression product is a protein.

According to a specific embodiment, the expression product brings about overexpression of an endogenous gene or homolog thereof or of a foreign gene expression product altogether. In embodiments of such cases, the expression product is heterologous to the plant/tissue being transformed.

It will be appreciated that the heterologous expression product can bring about down regulation of an endogenous gene such as by way of genome editing or RNA silencing.

The term "heterologous" as used herein refers to exogenous, not-naturally occurring within a native cell of a *cannabis* plant of a specific developmental stage, or not expressed in a plant, not expressed in a particular plant species, or is expressed at a different expression level or localization in the plant, than the native protein.

However, using genome editing for instance can also effect overexpression of an endogenous gene (e.g., by way of a "gain of function").

Genome editing as contemplates herein also mediates loss of function.

As used herein, the term "polypeptide" is used interchangeably with the terms "peptides", "oligopeptides" and "proteins" and refers to a biomolecule composed of amino acids of any length, linked together by peptide bonds.

The polypeptide of interest can be, for example, a plant polypeptide, a bacterial polypeptide, a viral polypeptide a mammalian polypeptide or a synthetic polypeptide (e.g., chimeric nuclease, nuclease e.g. cas9). Thus, the heterologous polypeptide of interest may be a plant polypeptide or protein that is a variant or mutated form of a plant polypeptide or protein or a polypeptide or protein not naturally found in the plant species, line or variety.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

The term "isolated" refers to at least partially separated from the natural environment.

According to one embodiment, the heterologous polypeptide of interest may include, but is not limited to, a reporter polypeptide, an antiviral polypeptide, a viral moiety, an antiviral polypeptide, an antifungal polypeptide, an antibacterial polypeptide, an insect resistance polypeptide, a herbicide resistance polypeptide, a biotic or abiotic stress tolerance polypeptide, a pharmaceutical polypeptide, a growth inducing polypeptide, a growth inhibiting polypeptide, an enzyme, a transcription factor and a transposase.

Exemplary proteins which may be produced, include, but are not limited to: nucleases, kinases, proteases, enzymes, hormones, proteins that provide resistance to diseases, antimicrobial proteins, antiviral proteins, and proteinaceous DNA editing agents.

According to one embodiment, the heterologous polypeptide of interest comprises two or more (e.g., 2, 3, 4) heterologous polypeptides.

According to one embodiment, the heterologous polypeptide of interest enables modifying the plant genome, e.g., nuclease.

As used herein the term "nuclease" refers to any polypeptide, or complex comprising a polypeptide, that can generate a strand break in the genome, e.g. in genomic DNA. According to an embodiment, the cleavage is site specific usually conferred by an auxiliary subunit, alternatively the nuclease is inherently specific to a target sequence of interest.

As used herein, the term "cleavage" or "DNA cleavage" refers to the breakage of the covalent backbone of a DNA molecule. Both single-stranded cleavage and double-stranded cleavage are possible, and double-stranded cleavage can occur as a result of two distinct single-stranded cleavage events. DNA cleavage can result in the production of either blunt ends or staggered ends.

Exemplary nucleases which may be used in accordance with the present teachings include restriction enzymes (e.g. type II restriction endonuclease), topoisomerases [e.g. DNA gyrase, eukaryotic topoisomerase II (topo II), and bacterial topoisomerase IV (topo IV)], recombinases (e.g. Cre recombinase, Hin recombinase), integrases, DNAses, endo-exonucleases (e.g. micrococcal nuclease) and homing endonucleases.

According to one embodiment, the nuclease utilized may comprise a non-specific DNA cleavage domain, for example, a type II restriction endonuclease such as the cleavage domain of the FokI restriction enzyme (GenBank accession number J04623).

According to one embodiment, the nuclease is a meganuclease.

As used herein, the term "meganuclease" refers to a double-stranded endonuclease having a large polynucleotide recognition site, e.g. DNA sequences of at least 12 base pairs (bp) or from 12 bp to 40 bp. The meganuclease may also be referred to as rare-cutting or very rare-cutting endonuclease. The meganuclease of the invention may be monomeric or dimeric. The meganuclease may include any natural meganuclease such as a homing endonuclease, but may also include any artificial or man-made meganuclease endowed with high specificity, either derived from homing endonucleases of group I introns and inteins, or other proteins such as zinc finger proteins or group II intron proteins, or compounds such as nucleic acid fused with chemical compounds.

Artificial meganucleases of the invention include, but are not limited to, custom-made meganucleases which are meganucleases derived from any initial meganuclease, either natural or not, presenting a recognition and cleavage site different from the site of the initial meganuclease, i.e. the custom-made meganuclease cleaves a novel site with an efficacy at least 10 fold, at least 50 fold or at least 100 fold more than the natural meganuclease.

Custom-made meganucleases may be produced by any method known in the art, for example, by preparing a library of meganuclease variants and isolating, by selection and/or screening, the variants able to cleave the targeted DNA sequence. The diversity could be introduced in the meganuclease by any method known to one skilled in the art, for example, the diversity may be introduced by targeted mutagenesis (i.e. cassette mutagenesis, oligonucleotide directed codon mutagenesis, targeted random mutagenesis), by random mutagenesis (i.e. mutator strains, Neurospora crassa system (U.S. Pat. No. 6,232,112; WO 01/70946, error-prone PCR), by DNA shuffling, by directed mutation or a combination of these technologies (See Current Protocols in Molecular Biology, Chapter 8 "Mutagenesis in cloned DNA", Eds Ausubel et al., John Wiley and Sons). The diversity may be introduced at positions of the residues contacting the DNA target or interacting (directly or indirectly) with the DNA target, or may be introduced specifically at the positions of the interacting amino acids. In libraries generated by targeted mutagenesis, the 20 amino acids can be introduced at the chosen variable positions. According to an embodiment, the amino acids present at the variable positions are the amino acids well-known to be generally involved in protein-DNA interaction. More particularly, these amino acids are generally the hydrophilic amino acids, e.g. comprise D, E, H, K, N, Q, R, S, T, Y. Synthetic or modified amino acids may also be used.

The custom-made meganuclease may be derived from any initial meganuclease.

According to one embodiment, the initial meganuclease is selected so as its natural recognition and cleavage site is the closest to the targeted DNA site. According to an embodiment, the initial meganuclease is a homing endonuclease. Homing endonucleases fall into 4 separated families on the basis of well conserved amino acids motifs, namely the LAGLIDADG family, the GIY-YIG family, the His-Cys box family, and the HNH family (Chevalier et al., 2001, N.A.R, 29, 3757-3774). According to one embodiment, the homing endonuclease is a I-Dmo I, PI-Sce I, I-SceI, PI-Pfu I, I-Cre I, I-Ppo I, or a hybrid homing endonuclease I-Dmo I/I-Cre I called E-Dre I (as taught in Chevalier et al., 2001, Nat Struct Biol, 8,312-316).

Further details relating to meganucleases are found in U.S. Pat. No. 8,697,395 which is incorporated herein by reference.

According to another embodiment, of the present invention, the nuclease comprises an oligonucleotide-dependent nuclease such as Cas or a RISC.

RISC enzymes are taught in Martinez J, Tuschl T. RISC is a 5' phosphomonoester-producing RNA endonuclease. Genes Dev. 2004; 18:975-980. Also contemplated are sequence modifications to improve plant expression i.e., homologs that are at least 60%, 65%, 70%, 75%, 80%, 85%, 90%, 95%. Homology and identity are also contemplated herein (e.g., using Blast(N)/(P) with default parameters).

According to one embodiment, the Cas9 or RISC is attached to a single guide RNA (sgRNA) to cleave genomic DNA in a sequence specific manner, hence the polynucleotide may encode the RNA targeting moiety such as a gRNA.

As used herein "a single guide RNA" or "sgRNA" refers to a chimeric RNA molecule which is composed of a clustered regularly interspersed short p_alindromic repeats (CRISPR) RNA (crRNA) and trans-encoded CRISPR RNA (tracrRNA). The crRNA defines a site-specific targeting of the Cas9 protein. The sequence is 19-22 nucleotides long e.g., 20 consecutive nucleotides complementary to the target and is typically located at the 5' end of the sgRNA molecule. The crRNA may have 100% complementation with the target sequence although at least 80%, 85%, 90%, and 95% global homology to the target sequence are also contemplated according to the present teachings.

The tracrRNA is 100-300 nucleotides long and provides a binding site for the nuclease e.g., Cas9 protein forming the CRISPR/Cas9 complex.

According to a specific embodiment a plurality of sgRNAs are provided to the plant cell that are complementary to different target nucleic acid sequences and the nuclease e.g., Cas9 enzyme cleaves the different target nucleic acid sequences in a site specific manner.

It will be appreciated that the sgRNA may be encoded from the same expression vector as the nuclease, e.g. Cas9. Additionally or alternatively, the sgRNA may be encoded from another nucleic acid construct and thus the CRISPR-Cas9 complex is encoded from a nucleic acid construct system.

According to another embodiment, sgRNA is encoded from the plant expression vector of the invention. In such a case the nuclease, e.g. Cas9, may be encoded from another nucleic acid construct and thus the CRISPR-Cas9 complex is encoded from a nucleic acid construct system.

Likewise, the plurality of sgRNAs may be encoded from a single vector or from a plurality of vectors as described herein. The use of a plurality of sgRNAs allows multiplexing.

Thus, the RNA-guided endonuclease of the invention comprises at least one nuclease (e.g. Cas9 or RISC) and at least one RNA binding domain (e.g. CRISPR). CRISPR/Cas proteins of the invention may comprise a nuclease domain, DNA binding domain, helicase domain, RNAse domain, protein-protein interaction domain and/or a dimerization domain.

According to one embodiment, the CRISPR/Cas protein can be a wild type CRISPR/Cas protein, a modified CRISPR/Cas protein, or a fragment of a wild type or modified CRISPR/Cas protein. Furthermore, the CRISPR/Cas protein can be modified to increase nucleic acid binding affinity and/or specificity, or to alter an enzymatic activity of the protein. For example, nuclease (i.e., Cas9) domains of the CRISPR/Cas protein can be modified.

Non-limiting examples of suitable Cas proteins which may be used in accordance with the present teachings include Cas3, Cas4, Cas5, Cas5e (or CasD), Cas6, Cas6e, Cas6f, Cas7, Cas8a1, Cas8a2, Cas8b, Cas8c, Cas9, Cas10, Cas1 Od, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966.

According to a specific embodiment, the cas nuclease is Cas9. Cas9 is a monomeric DNA nuclease guided to a DNA target sequence adjacent to the protospacer adjacent motif (PAM). The Cas9 protein comprises two nuclease domains homologous to RuvC and HNH nucleases. The HNH nuclease domain cleaves the complementary DNA strand whereas the RuvC-like domain cleaves the non-complementary strand and, as a result, a blunt cut is introduced in the target DNA.

In some embodiments, the CRISPR/Cas system comprises a wild type Cas9 protein or fragment thereof.

In other embodiments, the CRISPR/Cas system comprises a modified Cas9 protein. For example, the amino acid sequence of the Cas9 protein may be modified to alter one or more properties (e.g., nuclease activity, affinity, stability, etc.) of the protein. Alternatively, domains of the Cas9 protein not involved in RNA-guided cleavage can be eliminated from the protein such that the modified Cas9 protein is smaller than the wild type Cas9 protein.

According to one embodiment, the Cas9 protein can be modified to lack at least one functional nuclease domain. According to one embodiment, the Cas9 protein can be modified to lack all nuclease activity. According to another embodiment, the CRISPR/Cas system is fused with various effector domains, such as DNA cleavage domains. The DNA cleavage domain can be obtained from any endonuclease or exonuclease. Non-limiting examples of endonucleases from which a DNA cleavage domain can be derived include, but are not limited to, restriction endonucleases and homing endonucleases (see, for example, New England Biolabs Catalog or Belfort et al. (1997) Nucleic Acids Res.). In exemplary embodiments, the cleavage domain of the CRISPR/Cas system is a FokI endonuclease domain or a modified FokI endonuclease domain.

Various methods for designing CRISPR/Cas are known in the art and may be implemented in accordance with the present teachings. Further details relating to CRISPR/Cas can be found in PCT publication no. WO 2014089290 which is incorporated herein by reference in its entirety. According to another embodiment of the present invention, the nuclease comprises a chimeric nuclease.

As used herein the phrase "chimeric nuclease" refers to a synthetic chimeric polypeptide which forms a single open reading frame (ORF) and mediates DNA cleavage in a sequence specific manner.

According to a specific embodiment, the chimeric nucleases of this aspect of the present invention comprise separate domains for nucleic acid binding (e.g. DNA binding) and for nucleic acid cleavage (e.g. DNA cleavage), such that cleavage is sequence specific.

As used herein the phrase "sequence specific" refers to a distinct chromosomal location at which nucleic acid cleavage (e.g. DNA cleavage) is introduced.

As used herein the phrase "nucleic acid binding domain" refers to a native or synthetic amino acid sequence such as of a protein motif that binds to double- or single-stranded DNA or RNA in a sequence-specific manner (i.e. target site).

In order to induce efficient gene targeting, the nucleic acid (e.g. DNA) binding domain of the present invention needs to be coupled to a DNA cleavage domain (e.g. nuclease) as to permit DNA cleavage within a workable proximity of the target sequence. A workable proximity is any distance that still facilitates the sequence targeting. Optionally, the DNA binding domain overlaps the target sequence or may bind within the target sequence.

According to one embodiment, the chimeric nuclease induces a single stranded or a double stranded cleavage in the target site.

In generating chimeric nucleases any DNA or RNA binding domain that recognizes the desired target sequence (e.g. DNA binding sequence) with sufficient specificity may be employed. A variety of such DNA and RNA binding domains are known in the art.

Examples of DNA binding domains include, but are not limited to, a meganuclease binding domain, a helix-turn-helix (pfam 01381) binding domain, a leucine zipper (ZIP) binding domain, a winged helix (WH) binding domain, a winged helix turn helix domain (wHTH) binding domain, a helix-loop-helix binding domain, a transcription activator-like (TAL) binding domain, a recombinase, and a zinc finger binding domain.

In an exemplary embodiment of the present invention, the DNA binding domain is a zinc finger binding domain.

Thus, according to an embodiment of this aspect, the chimeric nuclease is a chimeric protein comprising a specific zinc finger binding domain (e.g., pfam00096) and the DNA cleavage domain, such as that of the FokI restriction enzyme (also referred to herein as the FokI cleavage domain), termed herein zinc finger nuclease (ZFN).

The zinc finger domain is 30 amino acids long and consists of a recognition helix and a 2-strand beta-sheet. The domain also contains four regularly spaced ligands for Zinc (either histidines or cysteines). The Zn ion stabilizes the 3D structure of the domain. Each finger contains one Zn ion and recognizes a specific triplet of DNA basepairs.

Zinc finger domains can be engineered to bind to a predetermined nucleotide sequence. Each individual zinc finger (e.g. Cys2/His2) contacts primarily three consecutive base pairs of DNA in a modular fashion [Pavletich et al., Science (1991) 252:809-817; Berg et al., Science (1996) 271:1081-1085]. By manipulating the number of zinc fingers and the nature of critical amino acid residues that contact DNA directly, DNA binding domains with novel specificities can be evolved and selected [see, e.g., Desjarlais et al., Proc. Natl. Acad. Sci. USA (1992) 89:7345-7349; Rebar et al., Science (1994) 263:671-673; Greisman et al., Science (1997) 275:657-661; Segal et al., Proc. Natl. Acad. Sci. USA (1999) 96:2758-2763]. Hence, a very wide range of DNA sequences can serve as specific recognition targets for zinc finger proteins. Chimeric nucleases with several different specificities based on zinc finger recognition have been previously disclosed [see for example, Huang et al., J. Protein Chem. (1996) 15:481-489; Kim et al., Biol. Chem. (1998) 379:489-495].

Various methods for designing chimeric nucleases with zinc finger binding domains are known in the art.

In one embodiment the DNA binding domain comprises at least one, at least two, at least 3, at least 4, at least 5 at least 6 zinc finger domains, binding a 3, 6, 9, 12, 15, or 18 nucleotide sequence, respectively. It will be appreciated by the skilled artisan that the longer the recognition sequence is, the higher the specificity that will be obtained.

Specific DNA binding zinc fingers can be selected by using polypeptide display libraries. The target site is used with the polypeptide display library in an affinity selection step to select variant zinc fingers that bind to the target site. Typically, constant zinc fingers and zinc fingers to be randomized are made from any suitable C2H2 zinc fingers protein, such as SP-1, SP-1C, TFIIIA, GLI, Tramtrack, YY1, or ZIF268 [see, e.g., Jacobs, EMBO J. 11:4507 (1992); Desjarlais & Berg, Proc. Natl. Acad. Sci. U.S.A. 90:2256-2260 (1993)]. The polypeptide display library encoding variants of a zinc finger protein comprising the randomized zinc finger, one or more variants of which will be selected, and, depending on the selection step, one or two constant zinc fingers, is constructed according to the methods known to those in the art. Optionally, the library contains restriction sites designed for ease of removing constant zinc fingers, and for adding in randomized zinc fingers. Zinc fingers are randomized, e.g., by using degenerate oligonucleotides, mutagenic cassettes, or error prone PCR. See, for example, U.S. Pat. Nos. 6,326,166, 6,410,248, and 6,479,626.

Zinc fingers can also be selected by design. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

According to another embodiment, the chimeric nuclease is a TALENs or a compact-TALENs (cTALENs).

As used herein, the term "TALENs" or "Transcription Activator-Like Effector Nucleases" refers to the artificial restriction enzymes generated by fusing the TAL effector DNA binding domain to a DNA cleavage domain. TALENs of the invention enable efficient, programmable, and specific DNA cleavage.

It will be appreciated that Transcription activator-like effectors (TALEs) can be quickly engineered to bind practically any DNA sequence. The term TALEN, as used herein, is broad and includes a monomeric TALEN that can cleave double stranded DNA without assistance from another TALEN. The term TALEN is also used to refer to one or both members of a pair of TALENs that are engineered to work together to cleave DNA at the same site. TALENs that work together may be referred to as a left-TALEN and a right-TALEN. Further details relating to TALENS can be found in U.S. Pat. Nos. 8,450,471; 8,440,431; 8,440,432; and U.S. Pat. Applic. No. 20140256798 all of which are incorporated herein by reference in their entirety.

TALEs are proteins secreted by *Xanthomonas* bacteria. The DNA binding domain of TALEs contains a highly conserved 33-34 amino acid sequence with the exception of the 12th and 13th amino acids. These two locations are highly variable [Repeat Variable Diresidue (RVD)] and show a strong correlation with specific nucleotide recognition. This simple relationship between amino acid sequence and DNA recognition has allowed for the engineering of specific DNA binding domains by selecting a combination of repeat segments containing the appropriate RVDs.

TALENs of the invention are typically constructed using a non-specific DNA cleavage domain, such as the non-specific DNA cleavage domain of FokI endonuclease. Thus, wild-type FokI cleavage domain may be used as well as FokI cleavage domain variants with mutations designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the DNA cleavage domain (e.g. FokI cleavage domain) and the number of bases between the two individual TALEN binding sites are parameters for achieving high levels of activity. The number of amino acid residues between the TALEN DNA binding domain and the DNA cleavage domain (e.g. FokI cleavage domain) may be modified by introduction of a spacer between the plurality of TAL effector repeat sequences and the nuclease (e.g. FokI endonuclease domain). The spacer sequence may be 12 to 30 nucleotides.

Furthermore, compact TALENs (cTALENs) may be used according to the present teachings. These cTALENs are typically designed with the partially specific I-TevI catalytic domain and are monomeric DNA-cleaving enzymes, i.e. TALENs which are half-size, single-polypeptide compact transcription activator-like effector nucleases (see Beurdeley M. et al., Nature Communications (2013) 4: 1762, which is incorporated herein by reference in its entirety).

The relationship between amino acid sequence and DNA recognition of the TALEN binding domain allows for designable proteins. In this case software programs (e.g. DNA-Works) may be used which calculate oligonucleotides suitable for assembly in a two step PCR; oligonucleotide assembly followed by whole gene amplification. Modular assembly schemes for generating engineered TALE constructs may also be used. Both methods offer a systematic approach to engineering DNA binding domains that are conceptually similar to the modular assembly method for generating zinc finger DNA recognition domains (described hereinabove).

Qualifying the nucleases (e.g. ZFN, TALENs and CRISPR/Cas) and meganucleases thus generated for specific target recognition can be effected using methods which are well known in the art.

A method for designing the nucleases (e.g. chimeric nucleases, ZFN, TALENs, Cas9, RISC, meganucleases) for use in gene targeting may include a process for testing the toxicity of the nuclease on a cell. Such a process may comprise expressing in the cell, or otherwise introducing into a cell, the nuclease and assessing cell growth or death rates by comparison against a control. The tendency of a nuclease to cleave at more than one position in the genome may be evaluated by in-vitro cleavage assays, followed by electrophoresis (e.g. pulsed field electrophoresis may be used to resolve very large fragments) and, optionally, probing or Southern blotting. In view of the present disclosure, one of ordinary skill in the art may devise other tests for cleavage specificity.

The heterologous polypeptide of interest (e.g. nuclease) disclosed herein may further comprise at least one nuclear localization signal (NLS) which facilitates the transport of the nuclease to the DNA-containing organelle. In general, an NLS comprises a stretch of basic amino acids which is recognized by specific receptors at the nuclear pores. The NLS can be located at the N-terminus, the C-terminal, or in an internal location of the nuclease.

Essentially any NLS may be employed, whether synthetic or a naturally occurring NLS, as long as the NLS is one that is compatible with the target cell (i.e. plant cell).

Although nuclear localization signals are discussed herewith, the present teachings are not meant to be restricted to these localization signals, as any signal directed to a DNA-containing organelle is envisaged by the present teachings. Such signals are well known in the art and can be easily retrieved by the skilled artisan.

Nuclear localization signals which may be used according to the present teachings include, but are not limited to, SV40 large T antigen NLS, acidic M9 domain of hnRNP A1, the sequence KIPIK in yeast transcription repressor Matα2 and the complex signals of U snRNPs, tobacco NLS and rice NLS.

In other exemplary embodiments, the localization signal for a DNA containing organelle can be a mitochondrial localization signal (MLS) or a chloroplast localization signal (CLS).

Mitochondrion localization signals (MLS) which may be used according to the present teachings include, but are not limited to the transition signals of, Beta ATPase subunit [cDNAs encoding the mitochondrial pre-sequences from *Nicotiana plumbaginifolia* f-ATPase (nucleotides 387-666)], Mitochondrial chaperonin CPN-60 [cDNAs encoding the mitochondrial pre-sequences from *Arabidopsis thaliana* CPN-60 (nucleotides 74-186] and COX4 [the first 25 codons of *Saccharomyces cerevisiae* COX4 which encodes the mitochondrial targeting sequence].

Chloroplast localization signals which may be used according to the present teachings include, but are not limited to the transition signals of the ribulose-1,5-bisphosphate carboxylase (Rubisco) small subunit (ats1A) associated transit peptide, the transition signal of LHC II, as well as the N-terminal regions of *A. thaliana* SIG2 and SIG3 ORFs.

See also www(dot)springerlink(dot)com/content/p65013h263617795/.

Alternatively, the chloroplast localization sequence (CLS) may be derived from a viroid [Evans and Pradhan (2004) US 2004/0142476 A1]. The viroid may be an Avsunviroidae viroid, for example, an Avocado Sunblotch Viroid (ASBVd), a Peach Latent Mosaic Virus (PLMVd), a *Chrysanthemum* Chlorotic Mottle Viroid (CChMVd) or an Eggplant Latent Viroid (ELVd).

According to a specific embodiment of the present invention, the localization signal may comprise a chloroplast localization signal.

In some embodiments, the heterologous polypeptide of interest (e.g. nuclease) further comprises at least one cell-penetrating domain. In one embodiment, the cell-penetrating domain can be a cell-penetrating peptide (CPP) sequence derived from Tat, Tat2, arginine-rich intracellular delivery peptides (AID), pVEC, transportan and penetratin.

According to a specific embodiment of the present invention, the CPP sequence comprises a dimmer of the Tat molecule (Tat2) which has an increased ability to translocate across plant cell membranes because of the presence of high number of arginine residues.

Various cloning kits can be used according to the teachings of some embodiments of the invention [e.g., Golden-Gate assembly kit by New England Biolabs (NEB)].

According to a specific embodiment, the nucleic acid construct is a binary vector. Examples for binary vectors are pBIN19, pBI101, pBinAR, pGPTV, pCAMBIA, pBIB-HYG, pBecks, pGreen or pPZP (Hajukiewicz, P. et al., Plant Mol. Biol. 25, 989 (1994), and Hellens et al, Trends in Plant Science 5, 446 (2000)).

Examples of other vectors to be used in other methods of DNA delivery (e.g. transfection, electroporation, bombardment, viral inoculation) are: pGE-sgRNA (Zhang et al. Nat. Comms. 2016 7:12697), pJIT163-Ubi-Cas9 (Wang et al. Nat. Biotechnol 2004 32, 947-951), pICH47742::2x35S-5'UTR-hCas9(STOP)-NOST (Belhan et al. Plant Methods 2013 11; 9(1):39), pAHC25 (Christensen, A. H. & P. H. Quail, 1996. Ubiquitin promoter-based vectors for high-level expression of selectable and/or screenable marker genes in monocotyledonous plants. Transgenic Research 5: 213-218), pHBT-sGFP(S65T)-NOS (Sheen et al. Protein phosphatase activity is required for light-inducible gene expression in maize, EMBO J. 12 (9), 3497-3505 (1993).

According to a specific embodiment, the vector is the binary vector, pME 504.

According to a specific embodiment, the transformation comprises a transient transformation.

According to a specific embodiment, the transformation comprises a stable transformation.

Various methods are known for plant transformation. For example, transient transformation can be done in the absence of a selection marker for 3-14 days. Stable transformation will typically require 4-10 weeks in the presence of a selection marker (e.g., antibiotics). Further transformation protocols are described hereinbelow.

The delivery of nucleic acids into a plant cell (contacted) in embodiments of the invention can be done by any method known to those of skill in the art, including, for example and without limitation: by desiccation/inhibition-mediated DNA uptake (See, e.g., Potrykus et al. (1985) Mol. Gen. Genet. 199:183-8); by electroporation (See, e.g., U.S. Pat. No. 5,384,253); by agitation with silicon carbide fibers (See, e.g., U.S. Pat. Nos. 5,302,523 and 5,464,765); by *Agrobacterium*-mediated transformation (See, e.g., U.S. Pat. Nos. 5,563,055, 5,591,616, 5,693,512, 5,824,877, 5,981,840, and 6,384,301); by acceleration of DNA-coated particles (See, e.g., U.S. Pat. Nos. 5,015,580, 5,550,318, 5,538,880, 6,160,208, 6,399,861, and 6,403,865) and by Nanoparticles, nanocarriers and cell penetrating peptides (WO201126644A2; WO2009046384A1; WO2008148223A1) in the methods to deliver DNA, RNA, Peptides and/or proteins or combinations of nucleic acids and peptides into plant cells.

Other methods of transfection include the use of transfection reagents (e.g. Lipofectin, ThermoFisher), dendrimers (Kukowska-Latallo, J. F. et al., 1996, Proc. Natl. Acad. Sci. USA93, 4897-902), cell penetrating peptides (Mae et al., 2005, Internalisation of cell-penetrating peptides into tobacco protoplasts, Biochimica et Biophysica Acta 1669 (2):101-7) or polyamines (Zhang and Vinogradov, 2010, Short biodegradable polyamines for gene delivery and transfection of brain capillary endothelial cells, J Control Release, 143(3):359-366).

According to a specific embodiment, the introduction of DNA into plant cells is effected by electroporation.

According to a specific embodiment, the introduction of DNA into plant cells is effected by bombardment/biolistics.

According to a specific embodiment, the introduction of DNA into plant cells is effected by *Agrobacterium* mediated transformation.

Viruses that have been shown to be useful for the transformation of plant hosts include CaMV, TMV, TRV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of some embodiments of the invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

Genome transformation can be evaluated phenotypically, i.e., by the presence/absence of a certain trait e.g., antibiotic resistance, resistance to disease or herbicide, morphologically (e.g., plant height), reporter gene expression (e.g., GUS) etc.

Genome transformation can also be evaluated molecularly. This is of specific significance in the case of genome editing.

Thus, regenerated tissues/plants are validated for the presence of a transformation event. The following provides such validation methods for genome editing events, also referred to herein as "mutation" or "edit", dependent on the type of editing sought e.g., insertion, deletion, insertion-deletion (Indel), inversion, substitution and combinations thereof.

Methods for detecting sequence alteration are well known in the art and include, but not limited to, DNA sequencing (e.g., next generation sequencing), electrophoresis, an enzyme-based mismatch detection assay and a hybridization assay such as PCR, RT-PCR, RNase protection, in-situ hybridization, primer extension, Southern blot, Northern Blot and dot blot analysis. Various methods used for detection of single nucleotide polymorphisms (SNPs) can also be used, such as PCR based T7 endonuclease, Hetroduplex and Sanger sequencing.

Another method of validating the presence of a DNA editing event e.g., Indels comprises a mismatch cleavage assay that makes use of a structure selective enzyme (e.g. m endonuclease) that recognizes and cleaves mismatched DNA.

The mismatch cleavage assay is a simple and cost-effective method for the detection of indels and is therefore the typical procedure to detect mutations induced by genome editing. The assay uses enzymes that cleave heteroduplex DNA at mismatches and extrahelical loops formed by multiple nucleotides, yielding two or more smaller fragments. A PCR product of ~300-1000 bp is generated with the predicted nuclease cleavage site off-center so that the resulting fragments are dissimilar in size and can easily be resolved by conventional gel electrophoresis or high-performance liquid chromatography (HPLC). End-labeled digestion products can also be analyzed by automated gel or capillary electrophoresis. The frequency of indels at the locus can be estimated by measuring the integrated intensities of the PCR amplicon and cleaved DNA bands. The digestion step takes 15-60 min, and when the DNA preparation and PCR steps are added the entire assays can be completed in <3 h.

Two alternative enzymes are typically used in this assay. T7 endonuclease 1 (T7E1) is a resolvase that recognizes and cleaves imperfectly matched DNA at the first, second or third phosphodiester bond upstream of the mismatch. The sensitivity of a T7E1-based assay is 0.5-5%. In contrast, Surveyor™ nuclease (Transgenomic Inc., Omaha, NE, USA) is a member of the CEL family of mismatch-specific nucleases derived from celery. It recognizes and cleaves mismatches due to the presence of single nucleotide polymorphisms (SNPs) or small indels, cleaving both DNA strands downstream of the mismatch. It can detect indels of up to 12 nt and is sensitive to mutations present at frequencies as low as ~3%, i.e. 1 in 32 copies.

Yet another method of validating the presence of an editing even comprises the high-resolution melting analysis.

High-resolution melting analysis (HRMA) involves the amplification of a DNA sequence spanning the genomic target (90-200 bp) by real-time PCR with the incorporation of a fluorescent dye, followed by melt curve analysis of the amplicons. HRMA is based on the loss of fluorescence when intercalating dyes are released from double-stranded DNA during thermal denaturation. It records the temperature-dependent denaturation profile of amplicons and detects whether the melting process involves one or more molecular species.

Yet another method is the heteroduplex mobility assay. Mutations can also be detected by analyzing re-hybridized PCR fragments directly by native polyacrylamide gel electrophoresis (PAGE). This method takes advantage of the differential migration of heteroduplex and homoduplex DNA in polyacrylamide gels. The angle between matched and mismatched DNA strands caused by an indel means that heteroduplex DNA migrates at a significantly slower rate than homoduplex DNA under native conditions, and they can easily be distinguished based on their mobility. Fragments of 140-170 bp can be separated in a 15% polyacrylamide gel. The sensitivity of such assays can approach 0.5% under optimal conditions, which is similar to T7E1 (After reannealing the PCR products, the electrophoresis component of the assay takes ~2 h.

Other methods of validating the presence of editing events are described in length in Zischewski 2017 Biotechnol. Advances 1(1):95-104.

It will be appreciated that positive clones can be homozygous or heterozygous for the transformation event. The skilled artisan will select the clone for further culturing/regeneration according to the intended use.

It will be appreciated that crossing of the plant can be effected to improve agricultural traits, losing a transgene, also known as "crossing out" (e.g., nuclease after genome editing was successfully implemented), or generation of inbreds or hybrids.

Following the present teachings, the present inventors were able to exhibit at least 50% regeneration efficiency, as calculated by the number of regenerates on the leaves/the total number of treated leaves.

Whilst reducing embodiments of the invention to practice, the present inventors have devised a protocol for in planta regeneration and transformation. Meristems are responsible for repair after injury: when the clonal zone of the shoot apical meristem is locally ablated, surrounding cells in the peripheral zone reconstruct the functional meristem. In shoots, meristems in axillary buds are kept dormant by the presence of apical meristems. Upon loss of these apical meristems, apical dormancy is broken and axillary buds begin to grow.

As used herein "in planta" means not under the sterile conditions of a tissue culture.

Accordingly, there is provided a method of in planta *cannabis* regeneration, the method comprising:
(a) removing, exposing and/or wounding a meristem of a *cannabis* tissue so as to obtain a meristem-depleted *cannabis* tissue; and
(b) treating said meristem-depleted *cannabis* tissue with a composition comprising at least one plant hormone (e.g., cytokinin, auxin gibberellins, ethylene, ABA, Jasmonic acid);

According to a specific embodiment, the at least one plant hormone comprises a cytokinin and an auxin.

Also provided is a method of in planta *cannabis* transformation, the method comprising:
(a) removing, exposing and/or wounding a meristem of a *cannabis* tissue so as to obtain a meristem-depleted *cannabis* tissue; and
(b) treating said meristem-depleted *cannabis* tissue with a composition comprising at least one plant hormone (e.g., cytokinin, auxin gibberellins, ethylene, ABA Jasmonic acid) that allows plant regeneration and with a composition comprising a nucleic acid sequence encoding an expression product of interest;

According to a specific embodiment, the at least one plant hormone comprises a cytokinin and an auxin.

According to this aspect, the *cannabis* tissue is a tissue that comprises meristems (axial or apical) prior to their depletion as described.

According to an embodiment of the invention, *cannabis* seeds are allowed to germinate and grow until a size when at least two nodes are observed.

In order to expose the meristem, one cotyledon and the meristem with its leaves (i.e., of a seedling) are cut off from the seedling (e.g., at 145°), leaving the seedling with only one cotyledon so as to allow photosynthesis. Other embodiments of the invention relate to the same protocol when done on a mature plant (e.g., cutting having 2 nodes of an adult plant). In the latter case too, at least one leaf (e.g., not more than 1 leaf) is left to allow photosynthesis.

At this stage the tissue is treated with hormone(s). For example, cytokinin and auxin, at the relevant ratios. In addition gibberellin, ethylene, ABA and/or Jasmonic acid can be added.

The use of a paste formulation may enhance penetration, though other modes of applications (e.g., spraying, dropping) can be used too.

According to a specific embodiment, the composition is formulated such that allows attachment of the composition to a surface of the meristem-depleted *cannabis* tissue.

According to a specific embodiment, the formulation comprises (e.g., ALGANATE) a nanoemulsion paste prepared according to Pereira et al., 2017 (Colloids and surfaces B: Biointerfaces 150:141-152) e.g., cytokinins and auxin gibberellins, ethylene, aba, Jasmonic acid hormones combinations are mixed with nanoemulsion (e.g., 3:4 v/v) to create a "regeneration paste". The paste is spread on the wounded cuttings.

According to a specific embodiment the nanoemulsion comprises lanolin.

As used herein "nanoemulsion" refers to clear, thermodynamically stable, isotropic liquid mixtures of oil, water and surfactant, frequently in combination with a co-surfactant. The aqueous phase may contain salt(s) and/or other ingredients, and the "oil" may actually be a complex mixture of different hydrocarbons and olefins, in contrast to ordinary emulsions, The regeneration can be effected together with the transformation (in this case, when *Agrobacterium* is used, it is better to employ a microemulsion that can comprise the bacterial cells). Accordingly, the composition which comprises the regenerating hormones can include also the nucleic acid of interest. Conversely, the same composition (e.g., alginate based) can be used for both transformation and regeneration even if taken in 2 different steps.

In a sequential embodiment, whereby the transformation step follows regeneration, the transformation composition is applied 0-96 hours following application of the regeneration composition comprising the hormones.

It will be appreciated that the plant can be first transformed and then subjected to a regeneration protocol.

According to a specific embodiment, the transformation is *Agrobacterium*-based.

*Agrobacterium* can be applied to the *cannabis* tissue in different modes e.g., dipping, microencapsulation, injecting and dripping.

Transformation and methods of validation are described herein.

Also provided herein is a method of *cannabis* regeneration via somatic embryogenesis, the method comprising:
(a) culturing a callus or a regenerable *cannabis* explant in a liquid culture while shaking till appearance of globular structures (e.g., as in FIG. 13A);
(b) culturing said globular structures in a liquid culture while shaking till appearance of leaves.

According to a specific embodiment, the regenerable *cannabis* explant is obtained according to the protocol of clonal propagation as described above.

According to a specific embodiment, the culturing is effected under shaking (such as described hereinabove) to elicit the development of embryonic tissue i.e., dedifferentiation that is followed by differentiation in the presence of CPPU and CPPU+cBD.

According to a specific embodiment, step (a) is effected in the presence of CPPU; and wherein step (b) is effected in the presence of CPPU+cBD.

According to a specific embodiment, step (a) is effected in the absence of cBD.

According to a specific protocol regeneration via somatic embryogenesis is effected as follows: a tissue explants having leaf segments of 1.5 cm diameter and 4-5 cm length are selected. Innermost leaf whorls are cut obliquely (0.5-1.0 cm), injured with a sharp scalpel blade in order to achieve callus initiation (de-differentiation). Leaf segments are used as explants for inoculation on MS medium (Murashige and Skoog 1962) supplemented with 2,4-D (4.0 mg/L) and kinetin [Kin] (0.5 mg/L). After 2-3 weeks the cultures are incubated at 25±2° C. at 70-80% humidity in dark in liquid Gamborg B5 medium supplemented with 6% sucrose and different plant hormones including the CPPU and cBD. The media was refreshed every three weeks.

Also provided is a method of in-vitro *cannabis* transformation, the method comprising, contacting a leaf producible according to the method as described herein with a polynucleotide encoding an expression product of interest. According to a specific embodiment, the polynucleotide is comprised in a formulation comprising *Agrobacterium* or PEG (as described herein).

Plants can also regenerate from protoplast or pollen. Whilst reducing embodiments of the invention to practice, the present inventors have identified a protocol for the efficient production of protoplasts using enzymatic digestion.

Accordingly there is provided a method of producing *cannabis* protoplasts, the method comprising, treating a *cannabis* tissue with macerozyme R-10 and mannitol, so as to obtain protoplasts.

As used herein "protoplast" refers to a plant cell devoid of a cell wall.

Protoplasts can be isolated from a wide variety of *cannabis* tissues and organs that include leaves, roots, shoot apices, embryos, microspores and mesophyll tissue of seedlings (e.g., cotyledons) or mature plants (e.g., leaves). In addition, callus and suspension cultures also serve as sources for protoplast isolation.

A sterile tissue is used. Disinfection can be done any time before the production of protoplasts.

The present inventors have found that a combination of macerozyme R-10 and mannitol allows the survival of at least 4% of isolated protoplasts following 48 hours cultivation in a liquid (drop) culture. In addition less than 1% of the protoplasts developed a cell wall.

Macerozyme R-10 is a macerating enzyme from the *Rhizopus* sp. which is suited for the isolation of plant cells. The enzyme has pectinase and hemicellulase activity.

Macerozyme R-10 is commercially available from a number of vendors including but not limited to Sigma-Aldrich, GoldBio(dot)Com and Yakult Pharmaceutical Industries Co.

As used herein "Mannitol" is used herein as a carbon source. It will be appreciated that other carbon sources such as sorbitol, fructose, glucose, galactose and sucrose can be alternatively used. Mannitol, being metabolically inert, may be preferred.

In an exemplary protocol, sterile cotyledons are cut to fine pieces (e.g., 1-5 mm) and incubated in a cell wall degrading solution e.g., W5—1.5% cellulose, 0.5% macerozyme, 0.4% mannitol, 20 mM KCl, 20 mM MES, 10 mM $CaCl_2$) and 0.1% BSA, placed in vacuum for 10 min and then shaken for 5 h at 50 rpm pH 4.5-7. The protoplasts are then filtered, diluted and pelleted by centrifugation. Up to now the procedure is done at room temperature. The protoplasts are re-suspended in a cell wall degrading solution (e.g., W5) and incubated on ice, before being centrifuged again and re-suspended in a solution containing mannitol and $MgCl_2$.

According to a specific embodiment, treating the tissue is also done with onzuka R-10 and/or hemicelluloses.

Cellulose or hemicelluloses are used to release the protoplasts from the cell debris.

As used herein "Onzuka R-10" refers to a cellulase derived from *Trichoderma viride*, which decomposes plant cell walls.

Other Onzuka cellulases can also be used e.g., Onzuka FA and Onzuka.

According to a specific embodiment, macerozyme R-10 is provided at a concentration of 0.4-1.5%.

According to a specific embodiment, said hemicellulose is provided at a concentration of 0.5-2%.

According to a specific embodiment, said Onzuka is provided at a concentration of 0.5-3%.

According to a specific embodiment, said mannitol is provided at a concentration of 0.1-0.3%.

The various enzymes for protoplast isolation are commercially available. For instance, Macerozyme R-10 is commercially available from a number of vendors including, but not limited to, Sigma-Aldrich, GoldBio(dot)Com and Yakult Pharmaceutical Industries Co.

The enzymes are typically used at a pH 4.5 to 6.0 (e.g., 5.8), temperature 25-30° C. (e.g., room temperature) with a wide variation in incubation period that may range from half an hour to 20 hours (e.g., 5 hours).

The enzyme digested plant cells, besides protoplasts contain undigested cells, broken protoplasts and undigested tissues. The cell clumps and undigested tissues can be removed by filtration. This is followed by centrifugation and washings of the protoplasts. After centrifugation, the protoplasts are recovered in a solution which may contain percoll or a combination of mannitol and salt (e.g., $MgCl_2$).

According to a specific embodiment at least 50-70% of the preparation comprises protoplasts that are viable and intact.

Thus, according to an embodiment, the isolated protoplasts are tested for viability and ability to undergo sustained cell divisions and regeneration.

Examples of methods for assessing protoplast viability include but are not limited to, fluorescein diacetate (FDA) staining method—The dye accumulates inside viable protoplasts which can be detected by fluorescence microscopy; phenosafranine stain is selectively taken up by dead protoplasts (turn red) while the viable cells remain unstained; exclusion of Evans blue dye by intact membranes; measurement of cell wall formation—Calcofluor white (CFW) stain binds to the newly formed cell walls which emit fluorescence; Oxygen uptake by protoplasts which can be measured by oxygen electrode; Photosynthetic activity of protoplasts; and ability of protoplasts to undergo continuous mitotic divisions (this is a direct measure).

Such protoplasts can be subjected to a method of transformation.

Typically in the absence of cell wall the DNA can be transferred using simple reagents such as PEG.

Thus, according to an embodiment of the invention, introducing DNA into protoplasts comprises polyethylene glycol (PEG)-mediated DNA uptake. For further details see Karesch et al. (1991) Plant Cell Rep. 9:575-578; Mathur et al. (1995) Plant Cell Rep. 14:221-226; Negrutiu et al. (1987) Plant Cell Mol. Biol. 8:363-373.

Based on the present teachings the present inventors were able to successfully introduce the RFP gene to *cannabis* protoplasts.

Also provided are protoplasts (transformed or not) obtainable according to the present teachings.

Protoplasts are then cultured under conditions that allow them to grow cell walls, start dividing to form a callus, develop shoots and roots, and regenerate whole plants.

The very first step in protoplast culture is the development of a cell wall around the membrane of the protoplast. This is followed by the cell divisions that give rise to a small colony. The cell colonies may be grown continuously as cultures or regenerated to whole plants. Protoplasts are cultured either in semisolid agar or liquid medium. In an embodiment, protoplasts are first allowed to develop cell wall in liquid medium, and then transferred to agar medium.

Solid culture (e.g., Agarose): The concentration of the agar should be such that it forms a soft agar gel when mixed with the protoplast suspension e.g., 0.5-0.7%. According to a specific embodiment, the plating of protoplasts is carried out by Bergmann's cell plating technique. In agar cultures, the protoplasts remain in a fixed position, divide and form cell clones. The advantage with agar culture is that clumping of protoplasts is avoided.

According to another embodiment, a liquid culture is used. Liquid culture may be used for protoplast cultivation for the following reasons:
1. It is easy to dilute and transfer.
2. Density of the cells can be manipulated as desired.
3. Osmotic pressure of liquid medium can be altered as desired.

In general, the nutritional requirements of protoplasts are similar to those of cultured plant cells, as mentioned above (e.g., MS).

According to some embodiments, the following considerations are taken place:
1. The medium should be devoid of ammonium, and the quantities of iron and zinc should be less.
2. The concentration of calcium should be 2-4-times higher than used for cell cultures. This is needed for membrane stability.
3. High auxin/kinetin ratio is suitable to induce cell divisions while high kinetin/auxin ratio is required for regeneration.
4. Glucose is the preferred carbon source by protoplasts although a combination of sugars (glucose and sucrose) can be used.
5. The vitamins used for protoplast cultures are the same as used in standard tissue culture media.

Osmoticum and Osmotic Pressure:

As used herein "Osmoticum" refers to the reagents/chemicals that are added to increase the osmotic pressure of a liquid.

The isolation and culture of protoplasts require osmotic protection until they develop a strong cell wall. In fact, if the freshly isolated protoplasts are directly added to the normal culture medium, they will burst. Thus, addition of an osmoticum is essential for both isolation and culture media of protoplast to prevent their rupture.

According to a specific embodiment, the osmoticum is non-ionic. The non-ionic substances most commonly used are soluble carbohydrates such as mannitol, sorbitol, glucose, fructose, galactose and sucrose. According to a specific embodiment, mannitol is used.

According to a specific embodiment, the osmoticum is ionic. Potassium chloride, calcium chloride and magnesium phosphate are the ionic substances in use to maintain osmotic pressure. When the protoplasts are transferred to a culture medium, the use of metabolically active osmotic stabilizers (e.g., glucose, sucrose) along with metabolically inert osmotic stabilizers (mannitol) is advantageous. As the growth of protoplasts and cell wall regeneration occurs, the metabolically active compounds are utilized, and this results in the reduced osmotic pressure so that proper osmolarity is maintained.

The culture techniques of protoplasts may vary.

According to a specific embodiment, the feeder layer technique or micro drop culture is used.

The process of cell wall formation in cultured protoplasts starts within a few hours after isolation that may take two to several days under suitable conditions. As the cell wall development occurs, the protoplasts lose their characteristic spherical shape. The newly developed cell wall by protoplasts can be identified by using calcofluor white fluorescent stain. The freshly formed cell wall is composed of loosely bound micro fibrils which get organized to form a typical cell wall. This process of cell wall development requires continuous supply of nutrients, particularly a readily metabolised carbon source (e.g. sucrose).

Cell wall development is found to be improper in the presence of ionic osmotic stabilizers in the medium. The protoplasts with proper cell wall development undergo normal cell division. On the other hand, protoplasts with poorly regenerated cell wall show budding and fail to undergo normal mitosis.

As the cell wall formation around protoplasts is complete, the cells increase in size, and the first division generally occurs within 2-7 days. Subsequent divisions result in small colonies, and by the end of third week, visible colonies (macroscopic colonies) are formed. These colonies are then transferred to an osmotic-free (mannitol or sorbitol-free) medium for further development to form callus.

With induction and appropriate manipulations, the callus can undergo organogenic or embryogenic differentiation to finally form the whole plant.

Plant regeneration can be done from the callus obtained either from protoplasts or from the culture of plant organs. There are however, certain differences in these two calli. The callus derived from plant organs carries preformed buds or organized structures, while the callus from protoplast culture does not have such structures.

To augment any of the above regeneration protocols, the present inventors have identified regenerating genes termed CsBBM (SEQ ID NO: 2 and 6) and CsSERK1 (SEQ ID NO: 1 and 10) that can facilitate plant regeneration.

Also contemplated are naturally occurring or synthetic homologs (e.g., of at least 30%, 40%, 50% or 80% nucleic acid identity of same).

Thus, according to an aspect of the invention there is provided a method of *cannabis* regeneration, the method comprising transforming an explant or plant (i.e., in planta) of the *cannabis* with a regenerating gene [e.g., CsBBM (SEQ ID NO: 2 and 6) and CsSERK1 (SEQ ID NO: 1 and 10)] and allowing the tissue to regenerate.

Such homologues can be, for example, at least 91%, at least 92%, at least 93%, at least 94%, at least 95%, at least 96%, at least 97%, at least 98%, at least 99% or 100% identical to SEQ ID NO:10 (amino acid sequence of CsSerk1), as determined using the BestFit software of the Wisconsin sequence analysis package, utilizing the Smith and Waterman algorithm, where gap weight equals 50, length weight equals 3, average match equals 10 and average mismatch equals −9.

According to an additional or an alternative embodiment, the homologues can be, for example, at least 50%, at least 60%, at least 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID NO:6 (amino acid sequence of CsBBM), as determined using the BestFit software of the Wisconsin sequence analysis package, utilizing the Smith and Waterman algorithm, where gap weight equals 50, length weight equals 3, average match equals 10 and average mismatch equals −9.

Naturally occurring homologs are provided in BnBBM, AthBBM, ZmBBM, AtSERK1, BnSERK1, SlSERK1. (SEQ ID NOs: 3-9).

Protocols for transformation (viral or non-viral dependent) are described throughout the specification.

Promoters useful for expression can be constitutively active or inducible (see e.g., WO2017/115353, WO2016/030885).

Nucleic acid sequences of the polypeptides of some embodiments of the invention may be optimized for plant expression. Examples of such sequence modifications include, but are not limited to, an altered G/C content to more closely approach that typically found in the plant species of interest, and the removal of codons atypically found in the plant species commonly referred to as codon optimization.

Also provided is a method of *cannabis* transformation. The method comprises contacting pollen of a *cannabis* plant with particles comprising a nucleic acid sequence encoding an expression product of interest under a magnetic field that concentrates said particles and allows penetration of said nucleic acid sequence of interest into said pollen.

Transformation under a magnetic field is typically referred to as "magnetofection".

The ability to transform *cannabis* using magnetofection is surprising, since to date the pollen apertures of *cannabis* have never been described.

This method is advantageous since it does not require plant regeneration.

In this system, exogenous DNA loaded with magnetic nanoparticles is delivered into pollen in the presence of a magnetic field.

The present inventors have surprisingly uncovered that fresh pollen i.e., up to 12 hours post harvesting exhibits better transformability.

Accordingly, magnetic nanoparticles (MNPs) are used as DNA carriers that can pass through the apertures in the pollen with the directional potential of a magnetic field (externally applied). Hence, positively charged polyethyleneimine-coated $Fe_3O_4$ MNPs are used as the DNA carriers for binding and condensing with electric negative DNA to form MNP-DNA complexes. After mixing MNP-DNA complexes with pollen, a magnetic field is then applied to direct the MNP-DNA complexes into the pollen through the apertures before pollination. Plants expressing a transgene of interest are then obtained typically after selection e.g., with an antibiotic.

According to an exemplary protocol, plasmid DNA (e.g., 1 ug) is left to bind with MNP's (MAGBIO, USA) at room temperature, prior to adding the transformation media: 10 g-40 Sucrose, $H_3BO_3$—10.3 mg, $KNO_3$—2.3 mg, $Ca(NO_3)_2$—10.3 mg, $MnSO_4$—10.3 mg, $MgSO_4$ 7H2O—10.3 mg, $GA_3$—3 mg, $H_2O$ up to 100 ml.

Pollen (1-10 million grains) added to the medium containing the bound MNP—plasmid and left on a magnet (Chemicell) for 30 min at room temp and dried in 30° C. for 30 min.

Based on the present teachings the present inventors were able to successfully introduce the GUS gene to *cannabis* pollen.

Any of the plant material described herein can be used for the generation of *cannabis* plants with advanced agricultural, nutritional, pharmaceutical, recreational properties, as compared to no-transformed plants of the same genetic background, developmental stage and growth conditions but not being transformed, also referred to herein as "control".

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

In-Vitro Propagation, Hardening and Rooting of Cannabis Cultivars

Cannabis has acquired considerable importance as a food, oil, fiber, medicinal and recreational drug source crop all over the world. This extraordinary versatile important plant material naturally calls for development of suitable protocols for production of sufficient number of uniform planting materials from Cannabis varieties through biotechnological intervention. Among the biotechnological approaches, micropropagation is one of the most feasible techniques, allows efficient and rapid clonal propagation of many economically important crops.

This study describes an efficient in-vitro propagation, hardening and rooting procedures for obtaining plantlets from shoot tips and seedlings of Cannabis sativa L. Ten different cannabis cultivars seedlings and shoot cuttings were sterilized and grown on half-strength ½ MS medium supplemented with 10 g/L sucrose, 5.5 g/L Agar at a pH of 6.8 with different plant hormone combinations under light for 16 h per day. Limited growth was observed on the solid media supplemented with different hormonal combinations in most of the cultivars tested. In order to increase cannabis plant permeability, a protocol was developed that utilizes "liquid treatment" in which the tissue culture explants are transferred from solid to liquid media supplemented with several sublethal concentrations of cuticle nicking enzymes every 3-4 weeks, resulting in significantly improved growth and development. The proliferated buds were successfully rooted on solid MS medium supplemented with resulting in 85% rooting of the plantlets. In-vitro clonal propagation, rooting and acclimatized plantlet production was established for 10 different Cannabis cultivars. The procedure requires a 50-70 days cycle for the In-vitro clonal propagation (20 days for shoot multiplication and 30 days for root induction) which includes 15-30 days for acclimatized plantlet production. Different strains may have different procedure time generally requiring between 50 to 100 days.

Materials and Methods

Plant Material

Ten different Cannabis cultivars representing a wide range of genetic diversity (Table 1) were used in this study. A few of them are hemp with low/non THC mainly used for fiber while the others are Cannabis cultivars with high THC and other cannabinoids for medical and recreational usage (e.g., 0-22% THC and 0.2-13% CBD). The plants of C. sativa were grown from seeds and cuttings.

TABLE 1

| No. | Name | Type | Usage | Origin |
|---|---|---|---|---|
| 106 | WON21 | Sativa | Fiber type | China |
| 108 | Pinola | Sativa Dioecious | Fiber type, Oil | Canada |
| 201 | Goodrich | Sativa | Medical | China |
| 202 | Glory | Sativa | Medical | China |
| 206 | Lemon Haze | Sativa | Drug type | Europe |
| 207 | White widow | Hybrid | Drug type | Europe |
| 208 | Jack herer | Hybrid | Drug type | Europe |
| 209 | Lemon Haze Bnn. | Hybrid | Drug type, Medical | Europe |
| 212 | Cheese | Hybrid | Drug type, Medical | Europe |
| 213 | SLH | Hybrid | Drug type, Medical | Europe |

Establishment and Propagation of Cannabis Tissue Culture from Mature Plants

Tissue Sterilization:

Cutting tissues from mature plants that contained apical and axillary meristems were washed under abundant water flow for 3 h. Tissues were then washed in ethanol 70% for 10 secs prior to 20 min wash in 1.5% NaClO.

Tissues were further abundantly washed 4 times in distilled water and set on different sterile proliferation growth medium. In order to determine an ideal composition for each line (Table 2).

Tissue Propagation

Every 21 days plants were transferred to a fresh propagation medium after carefully removing the leaves and exposure of side meristem.

Establishment and Propagation from Seeds

Seeds Sterilization and Germination

Seeds washed under abundant water flow for 2 h, then washed in ethanol 70% for 10 secs prior to 20 min wash in 1.5% NaClO supplemented with 0.1% Tween 20. Seeds were further abundantly washed 4 times in distilled water and set onto a sterile growth medium (½MS, 2% Sucrose, 0.8% agar). Seeds were germinated in the dark for 2 d and were then transferred to light. Two weeks later, large seedlings that contained at least two true leaves were cut from their roots and transferred to different sterile proliferation growth media. In order to determine an ideal composition for each line (Table 2).

Liquid Treatment

Young shoots were depleted from their leaves and necrotic tissue. They were then transferred to liquid medium that contained all growth components excluding Agar as mention in Table 2, below. Plantlets were grown in 250 ml jars containing 5 ml medium for shaking for 21 days and then transferred back to solid media.

Premium Liquid Treatment

Adding several sublethal concentrations of cuticle nicking enzymes to the liquid stage of the "liquid treatment". 5 ml enzyme reaction mixture (0.25 ml 10% fungal mix of pectin and cutinase enzyme (BSG HandCraft Liquid Pectic Enzyme; Cutinase—Sigma, Ferdinand Maria Quincy 0.25 ml 200 mM Tris-HCl) was added to 5 ml liquid media. Plants were incubated for 30 min in 30° C., then transferred to fresh liquid media.

The same medium was used for liquid and solid culturing.

TABLE 2

The different Proliferation media (PR), used for *Cannabis* tissue culture in this study

| Ingredients | PR13 | PR12 | PR 11 | PR 11 + PG | PR14 | PR 18A | PR 18B | PR 18C |
|---|---|---|---|---|---|---|---|---|
| MS | 1MS 0222 | 1MS 0222 | 1MS 0222 | 1MS 0222 | 1 MS B5 | 1MS 0222 | 1MS 0222 | 1MS 0222 |
| MS vitamins | | | 1 ml/l | | | | | |
| Sugar | 2% | 2% | 3% | 3% | 3% | 3% | 3% | 3% |
| BA | 2 mg/l | 2 mg/l | 1 mg/l | 1 mg/l | 0.25 mg/l | | | |
| TDZ | | | | | | 0.11 mg/l | 0.11 mg/l | |
| Zeatin | 2 mg/l | | | | | | | |
| NAA | | | | | 1 mg/l | | | |
| IBA | | | 0.2 mg/l | 0.2 mg/l | 0.05 mg/l | | | 0.5 mg/l |
| GA3 | 1 mg/l | 1 mg/l | 0.05 mg/l | 0.05 mg/l | 0.1 mg/l | | 2.4 mg/l | 0.2 mg/l |
| thiamine-HCl | | | 0.5 mg/l | 0.5 mg/l | | | | |
| Myo-inositol | | | 100 mg/l | 100 mg/l | 100 mg/l | | | 0.5 mg/l |
| Phlorpglucinol | | | | 89 mg/l | | | | 100 mg/l |
| Activated Charcoal | | | | | | | | 500 mg/l |
| Agar | 0.8% SigmaAgar | 0.8% SigmaAgar | 0.8% SigmaAgar | 0.8% SigmaAgar | 0.8% SigmaAgar | 0.8% gelrite | 0.8% gelrite | 0.8% gelrite |
| PH | 5.8 | 5.8 | 5.7 | 5.7 | 5.8 | 5.8 | 5.8 | 5.8 |

Rooting and Acclimatization

Rooting and acclimatization experiments were carried out initially with *Cannabis* cultivars 213 and 108.

Shoot was cultivated individually in a tube with root induction (RI) medium composed of half strength MS medium (½MS) supplemented with 100 mg/l myo-inositol, 1 mg/l thiamine-HCl, 90 mg/l phloroglucinol, 2% sucrose (w/v), 0.25% activated charcoal (AC), with or without IBA (at different concentrations (0, 1, 2 mg/l) and 0.8% agar. Soil mixture was moistened by soaking the rooting cylinders in liquid RI medium supplemented with either 0, 1, or 2 mg/l IBA. Each treatment consisted of 10 shoots and results were scored after 4 weeks. Each experiment was repeated three times.

Results

Figure 1:
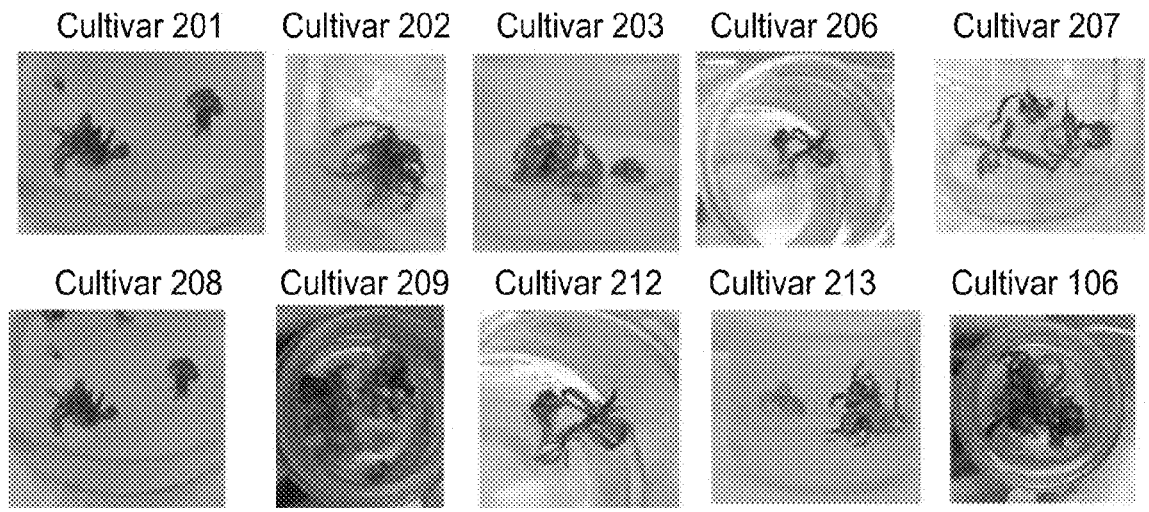
Figure 2:
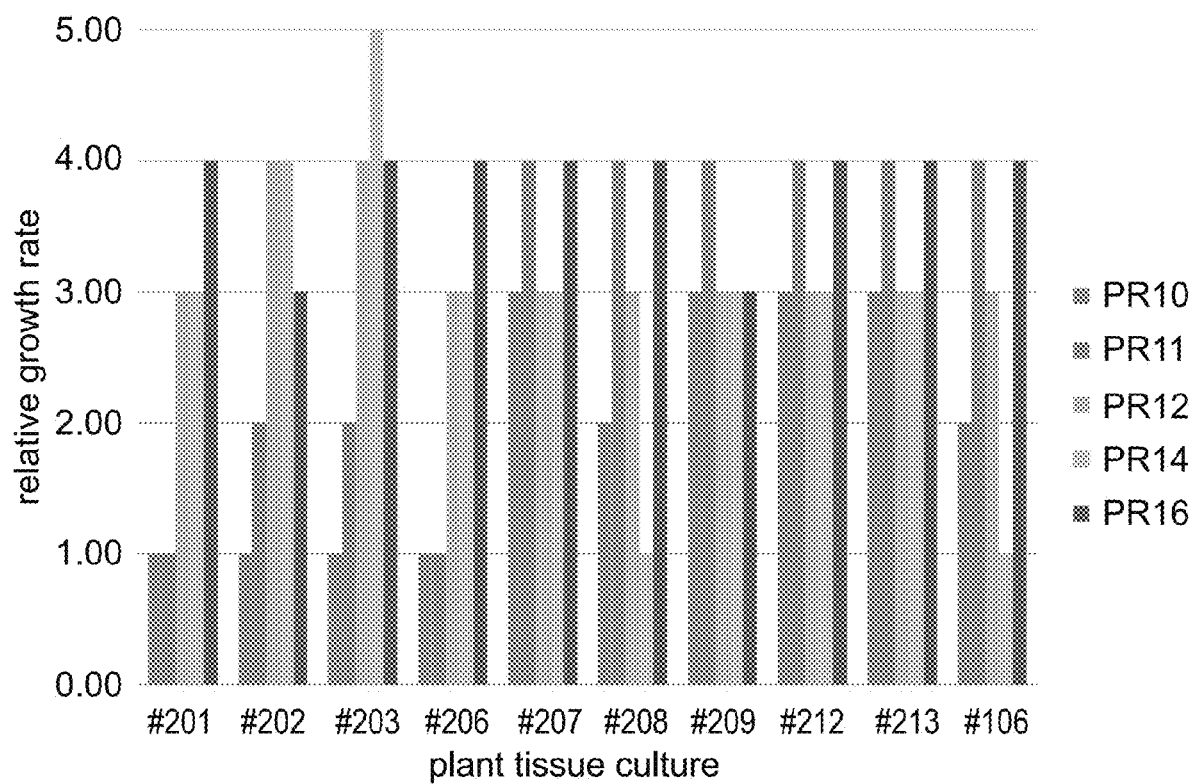

Effect of Cuticle Necking Enzymes and Transfer of Plants from Solid to the Liquid Medium on Proliferation of *Cannabis* Tissue Culture A tissue culture protocol was established for 10 different *Cannabis* cultivars representing a wide range of genetic diversity (FIG. 1). Several proliferation (PR) media were tested to determine the optimal medium for each cultivar based on their growth rate after 1-3 months (Table 2). Results are shown in FIG. 2.

Further analysis of the tissue culture showed a decline in the growth rate after 6 growth cycles probably because of limited ingredients uptake (FIG. 3A). In order to increase *cannabis* plant permeability a protocol for "liquid treatment" was developed in which the tissue culture was transferred from solid to liquid media every 3-4 weeks, and as a result significantly improved their growth and development (FIGS. 3B-3C).

To further increase plant permeability, the "liquid treatment" was supplemented by adding several sublethal cuticle nicking enzymes to the liquid stage with the aim of creating cracks in the plant cuticle. Pectin and cutinases are extracellular enzymes catalyzing the hydrolysis of the polyesters of the cuticle and the suberin layers, which protect plant surfaces. A protocol referred to as "premium liquid treatment" refers to the presence of cell wall degrading enzymes (Table 3, FIG. 4).

TABLE 3

Tissue culture response to "premium liquid treatment". Growth rate was measured from 1 (growth arrest) to 5 (rapid growth).

| | Cultivar 201 | Cultivar 202 | Cultivar 206 | Cultivar 207 | Cultivar 208 | Cultivar 209 | Cultivar 212 | Cultivar 213 | Cultivar 106 | Cultivar 108 |
|---|---|---|---|---|---|---|---|---|---|---|
| Liquid media | 3 | 4 | 3 | 2 | 3 | 3 | 2 | 1 | 3 | 2 |
| Liquid media with pectic Enzymes | 4 | 5 | 5 | 5 | 4 | 4 | 5 | 5 | 4 | 5 |
| Liquid media with cutinases enzymes | 4 | 5 | 5 | 5 | 5 | 4 | 4 | 5 | 3 | 5 |
| Solid medium after "premium liquid treatment" | 5 | 5 | 5 | 5 | 5 | 5 | 5 | 5 | 5 | 5 |

The combined liquid media with sublethal cuticle nicking enzymes and plant surfactants ("premium liquid treatment") increased plant growth and development in a significant manner. Moreover, the change in the *cannabis* cultivars surface permeability lasted even when the plants were sub-cultured again on solid medium (FIG. 4).

Rooting and Acclimatization

To obtain root induction, different concentrations of IBA were examined. The shoots were placed in a tube containing rooting medium containing 0, 1, or 2 mg/l IBA. Using this method with 2 mg/l IBA, about 85% of the shoots formed roots. However, only low percentage of these plants successfully acclimatized under greenhouse conditions. According to the second approach, shoots were cultured directly in rooting cylinders. After 4 weeks, 100% root formation was achieved, independently of the concentration of auxin used (FIGS. 5A-5C). These plants had better hardening and underwent easier acclimatization in greenhouse conditions. In-vitro clonal propagation, rooting and acclimatized plantlet production was established for 10 different *Cannabis* cultivars. According to an embodiment of the invention, the procedure requires a 50-70 days cycle for the In-vitro clonal propagation (20 days for shoot multiplication and 30 days for root induction) which includes 15-30 days for acclimatized plantlet production.

Example 2

*Cannabis* Regeneration and Transformation Using Tissue Culture

The development of new *Cannabis* cultivars with improved traits could be facilitated through the application of biotechnological strategies. The purpose of this study was to establish efficient regeneration of *Cannabis* in tissue culture and to establish a protocol for *Agrobacterium*-mediated transformation for foreign gene introduction.

Induction of high-frequency shoot regeneration using nodal segments containing axillary buds from tissue culture plants of *Cannabis sativa* was achieved on premium treatment media with cuticle nicking enzymes, added to Murashige and Skoog (MS) medium salt mixture, containing 0.05-5.0 µM thidiazuron, supplemented with 100 mg/l myo-inositol, 1 mg/l thiamine-HCl, 2% sucrose (w/v) at pH 5.7) with 5 ml cuticle nicking enzymes reaction mixture (0.25 ml 10% enzyme, fungal mix of pectin and cutinase (BSG HandCraft Liquid Pectic Enzyme; Cutinase—Sigma, Ferdinand Maria Quincy 0.25 ml 200 mM Tris-HCl). The quality and quantity of regenerates were better with media treatment with cuticle nicking enzymes and thidiazuron (0.5 µM thidiazuron). Adding 7.0 µM of gibberellic acid into a medium containing 0.5 µM thidiazuron slightly increased shoot growth. Stem and leaf segments from seedlings and tissue culture of four *Cannabis* varieties were placed on Murashige and Skoog medium with Gamborg B5 vitamins (MB) supplemented with different combination of plant growth regulators and 3% sucrose, and 8 g 121 agar. Large masses of callus were produced within 4 weeks for all cultivars. Transformation with *Agrobacterium tumefaciens* strain EHA105 harboring the vector pME 504 carrying the nptII and the uidA-intron genes for *Cannabis* callus, hypocotyls, leaves and cotyledons were established.

Material and Methods

Regeneration Using Premium Treatment

Regeneration from *Cannabis* plant material using tissue culture, germinated leaves, cotyledons and hypocotyls were used for regeneration. The plants were placed on a petri dish containing 20 ml regeneration media using premium treatment with cuticle nicking enzymes: MS salt mixture, supplemented with 100 mg/l myo-inositol, 1 mg/l thiamine-HCl, 2% sucrose (w/v) at pH 5.7) with and without 5 ml pectic enzymes reaction mixture (0.25 ml 10% enzyme fungal mix of pectin and cutinase 0.25 ml 200 mM Tris-HCl).

Regeneration from Leaves

Three youngest expanding leaves isolated from 3 to 4 weeks old plants were with and placed on regeneration medium with cuticle nicking enzymes (Murashige and Skoog (MS) medium salt mixture, containing 0.05-5.0 µM thidiazuron, supplemented with 100 mg/l myo-inositol, 1 mg/l thiamine-HCl, 2% sucrose (w/v) at pH 5.7, with 5 ml pectic enzymes reaction mixture (0.25 ml 10% cuticle nicking enzyme in 0.25 ml 200 mM Tris-HCl). The cultures were kept for 7 days in low light intensity (2.5 mmol/m2 s) followed by exposure to high light intensity (40 mmol/m2 s) at 25° C., in a 16/8 h photoperiod. Leaf explants were examined after 14 and 21 days and the percentage of explant producing shoots were calculated.

Regeneration from Cotyledon

Seeds were washed under abundant water flow for 2 h, and then washed in ethanol 70% for 10 secs prior to 20 min wash in 1.5% NaClO with 0.1% Tween 20. Seeds washed 4 times in distilled water and set onto a sterile growth medium (½MS, 2% Sucrose, 0.8% agar). Seeds were germinated in the dark for 2 days and were then transferred to light. Two weeks later, cotyledon from large seedlings that contained two true leaves were cut and placed on regeneration medium with cuticle nicking enzymes (Murashige and Skoog (MS) medium salt mixture, containing 0.05-5.0 µM thidiazuron, supplemented with 100 mg/l myo-inositol, 1 mg/l thiamine-HCl, 2% sucrose (w/v) at pH 5.7, with 5 ml pectic enzymes reaction mixture (0.25 ml 10% enzyme, 0.25 ml 200 mM Tris-HCl). The cultures were kept in high light intensity (40 mmol/m2 s) at 25° C., in a 16/8 h photoperiod.

Regeneration from Callus 21 days old tissue culture were placed on PR12 solid media (MS, 2% sucrose, 2 mg/l BA, 1 mg/l GA3, 0.8 sigma agar, pH 5.8) to encourage the creation of callus. Two weeks later, calli were replaced on regeneration medium with cuticle nicking enzymes (Murashige and Skoog (MS) medium salt mixture, containing 0.05-5.0 µM thidiazuron, supplemented with 100 mg/l myo-inositol, 1 mg/l thiamine-HCl, 2% sucrose (w/v) at pH 5.7, with 5 ml pectic enzymes reaction mixture (0.25 ml 10% enzyme, 0.25 ml 200 mM Tris-HCl). The cultures were kept in high light intensity (40 mmol/m2 s) at 25 8 C, in a 16/8 h photoperiod.

*Agrobacterium tumefaciens* Strain and Plasmid

The super-virulent *Agrobacterium tumefaciens* strain EHA 105 harboring the vector pME 504 carrying the nptII and the uidA-intron genes was used. An *Agrobacterium* culture was grown overnight in LB medium with appropriate antibiotics. Bacteria were spun down by centrifugation (4000 rpm for 15 min), resuspended in liquid SIM medium supplemented with 100 µM Acetosyringone (AS) to obtain a final OD600 of 0.7, and incubated in an orbital shaker at 28° C. and 250 rpm for 4 h.

*Cannabis* Transformation

Leaves of 3-4 weeks old micropropagated shoots were wounded and immersed in the bacterial suspension for 20 min, dry-blotted on a filter paper and cultured on regeneration medium using the premium treatment with sublethal cuticle nicking enzymes based on MS salt mixture, supplemented with 2.0 mg/l TDZ and 2 mg/l IBA, 100 mg/l myo-inositol, 1 mg/l thiamine-HCl, 2% sucrose (w/v) at pH 5.7) whit 5 ml pectic enzymes reaction mixture (0.25 ml 10% enzyme, 0.25 ml 200 mM Tris-HCl). Transformation was evaluated by GUS staining.

GUS Staining

Fresh plant material was transferred to a histochemical reagent (1.1 mM X-Gluc in 100 mM potassium phosphate buffer pH 7.0: 5 mM potassium ferrocyanide, 5 mM potassium ferricyanide and 0.1% Triton X-100) and incubated for one hour to overnight at 37° C. After staining, the disks were transferred to 70% ethanol for 1 h to overnight until bleached.

Molecular Confirmation of Transformation

To verify the presence and integration of the nptII and GUS genes, all selected clones were subjected to molecular analyses by PCR. Plant genomic DNA was isolated from leaves according to Murray, M. G., and W. Fm Thompson. "Rapid isolation of high molecular weight plant DNA." *Nucleic acids research* 8.19 (1980): 4321-4326.

The oligonucleotide primers used for the PCR amplification of a 645 bp fragment of the nptII gene were:

```
Direct primer
                              (SEQ ID NO: 12)
5'-GCC GCT TGG GTG GAG AGG CTA T- 3' (63.6° C.);

Reverse primer
                              (SEQ ID NO: 13)
5'-GAG GAA GCG GTC AGC CCA TTC- 3' (60° C.).
```

The primers for a 676 bp fragment of the GUS gene were:

```
GUSup
                              (SEQ ID NO: 14)
5' -CGA GCG ATT TGG TCA TGT GAA G- 3' (57.5° C.);

GUSlow primer
                              (SEQ ID NO: 15)
5'-CAT TGT TTG CCT CCC TGC TGC GGT T- 3'

(55.9° C.) (Sigma).
```

Amplification was performed in aliquots of 25 µl using a thermal cycler (Biometra). The PCR conditions for amplification of the nptII gene fragment were 95° C. for 5 min, followed by 35 cycles at 94° C. for 1 min, 62° C. for 1 min, 72° C. for 1 min, and a final extension at 72° C. for 10 min. Amplification of the uidA-intron fragment was performed according to the following program: 95° C. for 5 min followed by 35 cycles at 94° C. for 45 s, 55° C. for 45 s, 72° C. for 45 s, and a final extension at 72° C. for 10 min.

Results

The "Regeneration Premium treatment" with cuticle nicking enzymes increased *Cannabis* regeneration rate. In preliminary experiments, about 5 to 10% of the explants exhibited shoot regeneration when cultured on a regeneration medium supplemented with hormones.

In order to increase plant regeneration rate a "regeneration premium treatment" was added including the addition of cuticle nicking enzymes to the solid medium. "Regeneration Premium treatment" increased plant regeneration ten times more compared with non-treated plants in all the tested cultivars (Table 4).

TABLE 4

The effect of hormones concentration and "regeneration premium treatment" on shoot regeneration of several *cannabis* lines (% regeneration)

| | Cultivar 201 | Cultivar 202 | Cultivar 208 | Cultivar 209 | Cultivar 212 | Cultivar 213 | Cultivar 106 | Cultivar 108 |
|---|---|---|---|---|---|---|---|---|
| MS regeneration medium | 5 | 3 | 4 | 5 | 8 | 9 | 11 | 22 |
| MS regeneration medium + Pectic Enzymes | 46 | 61 | 55 | 49 | 50 | 57 | 61 | 52 |
| MS regeneration medium + Pectic Enzymes + Triton X-100 + s | 53 | 66 | 60 | 49 | 55 | 60 | 75 | 70 |

The "premium treatment" enhanced *cannabis* regeneration from different plant organs: plant cotyledons, callus and leaves (FIG. 4).

Transformation

Figure 7:
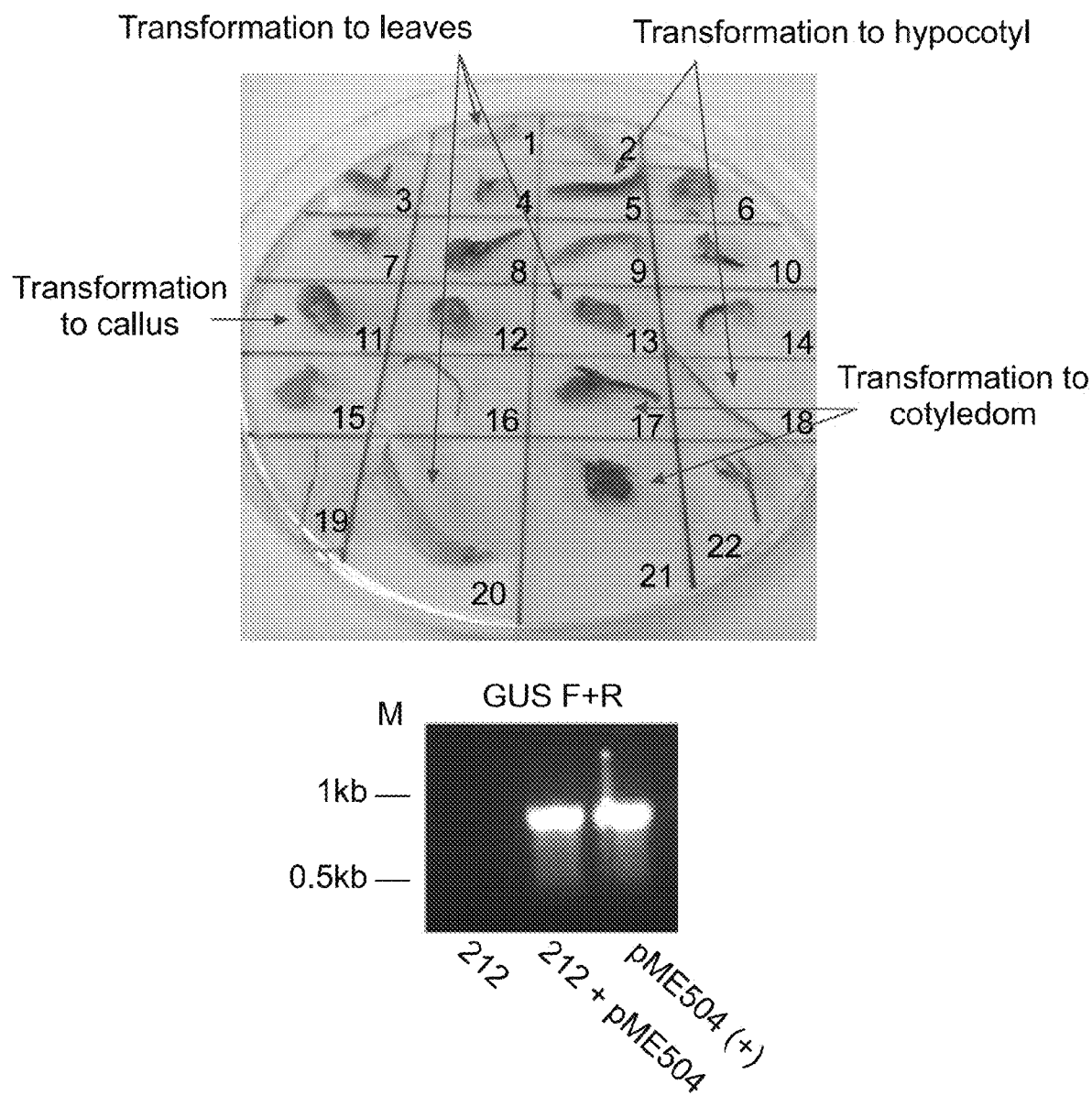

The present study describes the successful transformation of several *cannabis* cultivars using the uidA-intron and nptII genes. An efficient transient transformation of leaves, hypocotyls, callus and cotyledons of several *Cannabis* cultivars was observed (FIG. 7 upper panel). Transformation of the selected clones has been confirmed by GUS histochemical assay and molecular analysis. Positive PCR was shown in all tested clones (FIG. 7, lower panel). The transformation was confirmed by GUS staining and PCR. Stable transformation is tested by subcultures of the plants in selective conditions of 100 mg 1-1 kanamycin.

Example 3

In Planta Regeneration and Transformation of *Cannabis* Cultivars

Alternate methods that avoid/minimize tissue culture would be beneficial for the development of new transgenic *Cannabis* cultivars. Transgenic *Cannabis* plants have been produced by a tissue-culture independent *Agrobacterium tumefaciens*-mediated transformation procedure. One of the two cotyledons of germinated *Cannabis* seedlings was excised. Unique regeneration method using plant hormones in a nano-encapsulation paste were introduced to the excised apical meristem of the germinating seedling. Regeneration of more than 80% of the germinating seedlings was obtained. A similar regeneration ratio was achieved with adult *Cannabis* plants of three different cultivars, suggesting that the nano encapsulation paste induces efficient regeneration. *Agrobacterium* strain EHA 105 harboring the binary vector pME504 that carries the genes for β-glucuronidase (GUS) and neomycin phosphotransferase (npt II), or the plasmid carrying the nptII and betalain genes (Polturak, Guy, et al. "Engineered gray mold resistance, antioxidant capacity, and pigmentation in betalain-producing crops and ornamentals." *Proceedings of the National Academy of Sciences* (2017): 201707176).

For in planta transformation, *Agrobacterium* strain EHA 105 harboring the different binary plasmids was mixed with the emulsifier paste to enhance attachment to the cut plant surface. The proof of transformability in the T0 generation was indicated by the GUS histochemical analysis of the seedlings (wounded seedlings with the single cotyledon) ten days after co-cultivation and was further confirmed by PCR analysis and typical betalains red leaves expression. Molecular characterization and GUS and betalains expression analysis were done using PCR.

Materials and Methods

Plant Material

Seeds—*Cannabis Sativa* L. seeds (from various cultivars) were surface sterilized with 1.5% sodium hypo chloric acid followed by several washes with sterile water. Seeds were germinated on sterile, wet, filter paper disks until visible root emergence.

Seedlings—seeds were germinated in solid media (soil, vermiculite, MS, etc.) until first two true leaves were observed (between 2-4 true leaves).

Plants—seeds were allowed to germinate and grow to a size when at list two nodes were observed.

"Pre-Regeneration Tissue Preparation"

One cotyledon and the meristem with its leaves were cut off from the seedlings at 145°, leaving the seedling with only one cotyledon. Plants were allowed to grow until at least 2 nodes were apparent, then the shoot was cut off from lowest leaf at 145°, leaving the plant with only one leaf.

"Regeneration Paste"

Several hormonal combinations sets were made and applied to cut seedlings and cut plants by spraying or by ALGANATE™ nanoemulsion paste prepared according to Pereira et al., 2017 (Colloids and surfaces B: Biointerfaces 150:141-152); different cytokinins and auxin hormones combinations in various concentrations were mixed with nanoemulsion (usually 3:4 v/v) to create a "regeneration paste". The paste was spread on the wounded cuttings Imaging for the Detection of in Planta Regeneration Scanning Electron Microscopy Scanning Electron Microscopy was done with a Hitachi TM-3030Plus microscope. Imaging was done under low vacuum conditions without any sample preparation.

Histology

The tissue was fixed in 10% Formalin, 5% acetic acid and 50% alcohol (FAA) for 24 h, followed by gradual dehydration in a set of increasing concentrations of ethanol, which was replaced by Histo-Clear and embedded in paraffin. The embedded tissue was cut to 10 µm sections using a Lecica RM2245 microtome and stained with Safranin/Fast Green. Samples were viewed using light microscope (DMLB, Leica) or stereoscope (MZFLIII, Leica).

*Agrobacterium tumefaciens* Strain and Plasmid

Super-virulent *A. tumefaciens* strain EHA105 harboring the vector pME 504 carrying the uidA-intron reporter gene and the nptII resistant genes or the vector pX 11 carrying the nptII and betalain genes were used. See also Poluraka et al. PNAS Aug. 22, 2017. 114 (34) 9062-9067;

Bacteria were spun down by centrifugation (8000 g for 10 min). Bacteria were re-suspended in a transformation buffer (1 MS, 5.86 g/l MES, 1% sucrose, pH 7.0) with 100 mg/l acetosyringone, to obtain a final $OD_{600}$ of 0.6, and incubated in an orbital shaker at 28° C. while shaking at 250 rpm for 3 h until plant infection.

Plant material (micropropagated shoots from tissue culture, seedling or seeds) were vacuum infiltrated for 5 min in a vacuum desiccator. The infiltration followed by co-cultivation with the *agrobacterium* for 30 min at R.T, then transferred for further growth on infection medium.

Pre-Transformation Tissue Preparation

Prior to *agrobacterium* transformation, all tissues were mechanically treated; seeds were cut, pressed or punched with the root remaining intact. One cotyledon and the meristem with its leaves were cut off from the seedlings at 145°, leaving the seedling with only one cotyledon. Plants were allowed to grow until at least 2 nodes were apparent, then the shoot was cut off from the lowest leaf at 145°, leaving the plant with only one leaf.

Agro Mediated Transformation

Binary plasmids for various genetic modification purposes were introduced into *Agrobacterium tumefaciens*. *Agrobacterium* was applied to the tissue in different ways; a. dipping, b. microencapsulation, c. injecting and d. dripping. In any case, *agrobacterium* comprising the desired plasmid was grown in the presence of selective antibiotics which were later replaced by an activation medium. In case of dipping, treated seeds or seedlings were co-cultivated with the bacteria for 2 min to several hours. When microencapsulation was applied, several activating media were tested: MS0, half MS0, SIM and CT.

Microencapsulation Transformation

*Agrobacterium* was grown and activated as described in materials and methods, and then it was mixed with lanolin nano-emulsifier (according to Zhang et al 2014 (Nanotechnology, 25(12), 125101) usually at 3:4 (v/v) ratio. The resultant paste was spread on the cutting up to 24 h after performance of the cut.

GUS Staining

A fresh plant material was transferred to a histochemical reagent (1.1 mM X-Gluc in 100 mM potassium phosphate buffer pH 7.0: 5 mM potassium ferrocyanide, 5 mM potassium ferricyanide and 0.1% Triton X-100) and incubated for one hour to overnight at 37° C. After staining, the disks were transferred to 70% ethanol for 1 h to overnight until bleached.

Betalains Separation

For betalains observation, fresh tissue (0.5 g) was ground in the presence of CTAB buffer (3% CTAB, 28% NaCl, 4% EDTA, 10% Tris HCl, 3% PVP and 25% water), mixed with chloroform and centrifuged.

Results

In Planta Regeneration Using a Regeneration Paste

Genetic modifications (i.e. genome editing, gene transfer, etc.') require a platform for introducing those modifications into the plant cells and an efficient method for regenerating the modified cells only to get a new, modified plant. In many cases, this could be the bottleneck for establishing an efficient transformation protocol. Development of an in planta transformation protocol may eliminate the use of tissue culture.

Figure 8A:
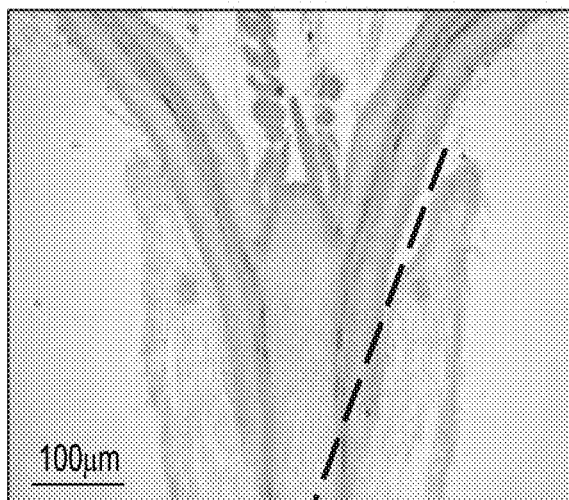
Figure 8B:
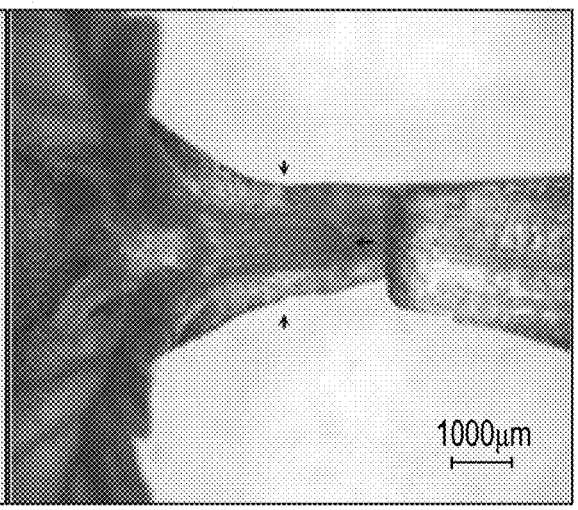
Figure 8C:
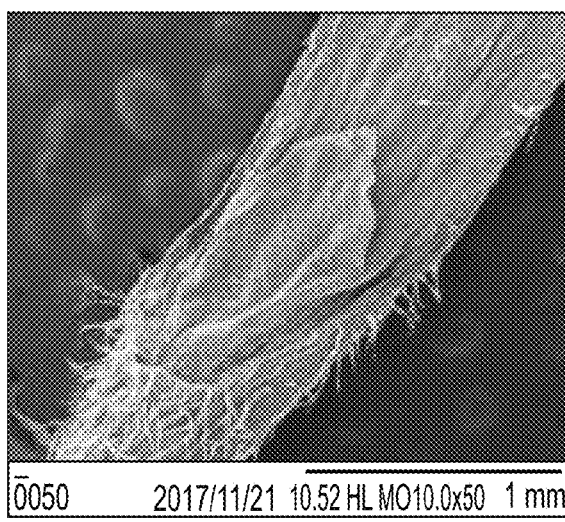
Figure 8D:
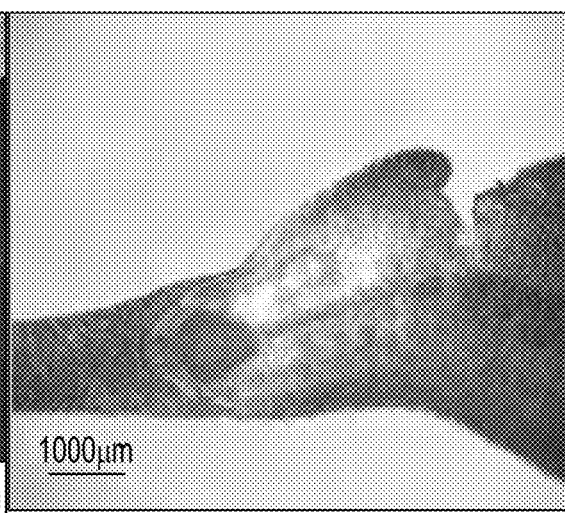

Seedlings were germinated in solid media, when first two leaves were observed (FIGS. 8A-8B) the meristem with its leaves and one of the cotyledons was removed (FIGS.

Figure 8E:
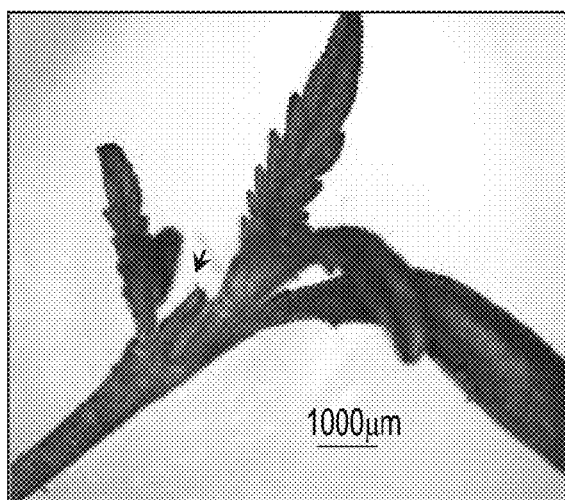
Figure 8F:
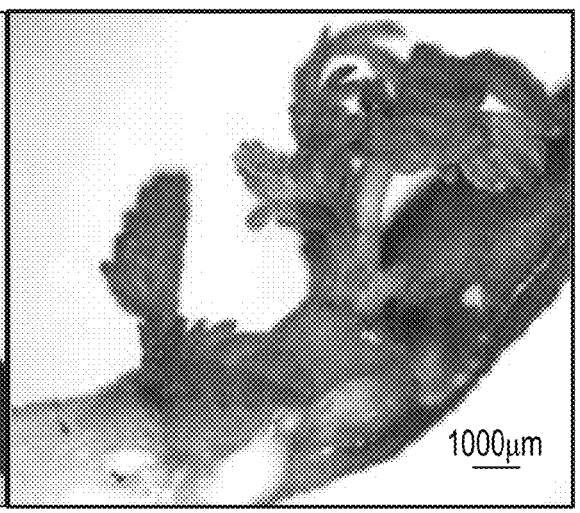

8A-8D). The wounded tissue was spread with the regeneration paste. The seedlings were left to grow at 16 h light and after 7 days regeneration from around the cut area was observed (FIGS. 8E-8F). After 7 days regeneration events were observed and after 12 days seedlings were evaluated for different events as shown in Table 5 below.

Figure 9:
FIG. 9 is an image showing in planta regeneration of *cannabis* cuttings, using the "regeneration paste" according to the embodiment described in the Examples section with appropriate plant hormone combinations. Plant regeneration was observed 14 days after application of the "regeneration past".
Figure 10A:
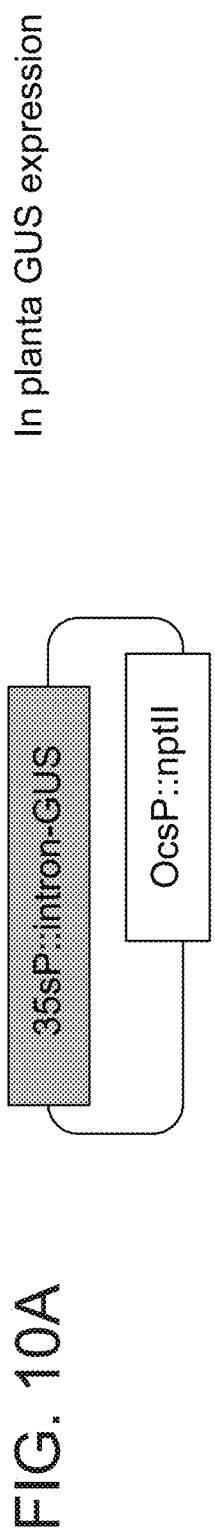
FIGS. 10A-10C show in planta transformation using the *Agrobacterium* strain EHA 105 harboring the binary vector pME504 that carries the genes for β-glucuronidase (GUS) and neomycin phosphotransferase (npt II). The proof of transformability in the TO generation was indicated by the GUS histochemical staining analysis of the seedlings and molecular characterization and GUS and nptII, using PCR.
Figure 10B:
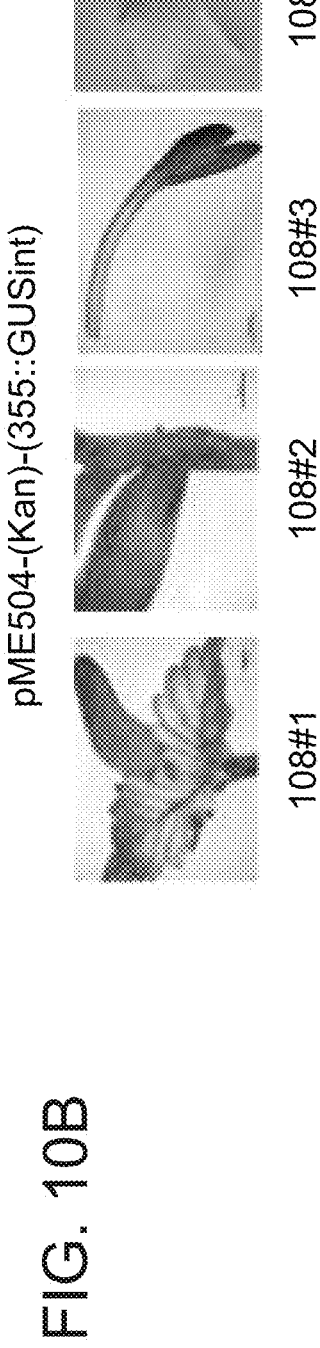
Figure 10C:
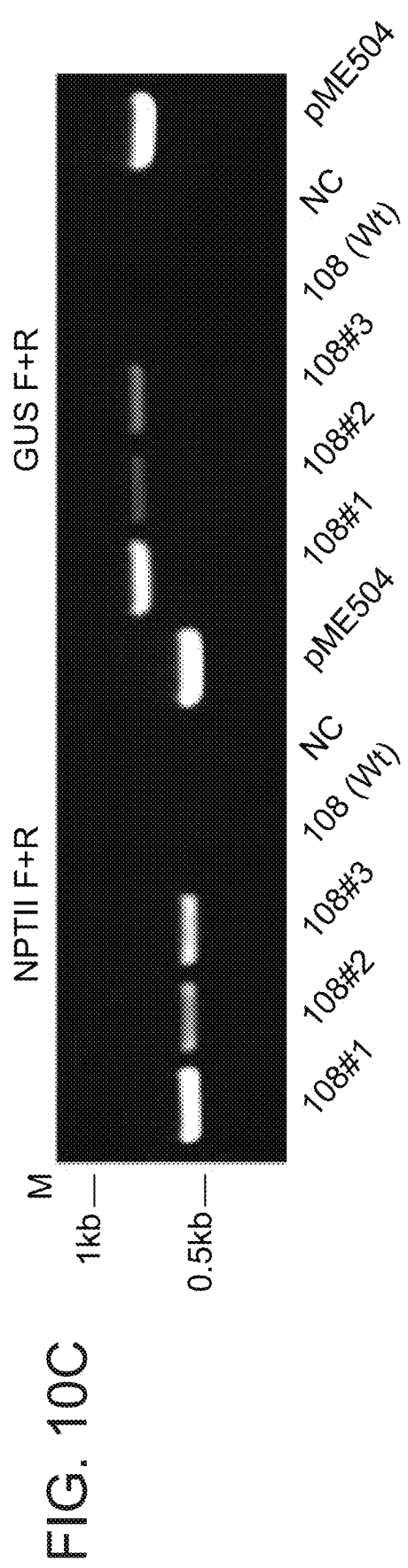
Figure 11A:
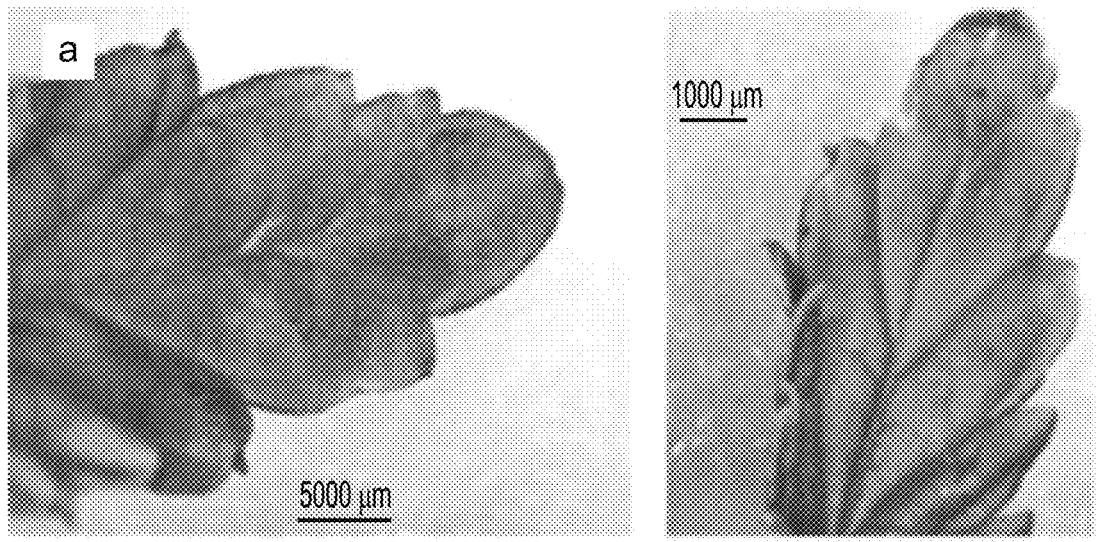
FIGS. 11A-11C show in planta transformation using the *Agrobacterium* strain EHA 105 harboring the binary vector pX11 that carries the genes for nptII and betalains. The proof of transformability in the $T_0$ generation was indicated by betalains staining (FIGS. 11A-B) and PCR.
Figure 11B:
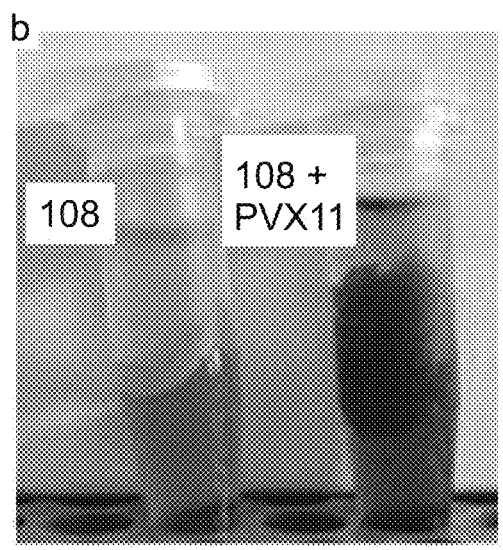
Figure 11C:
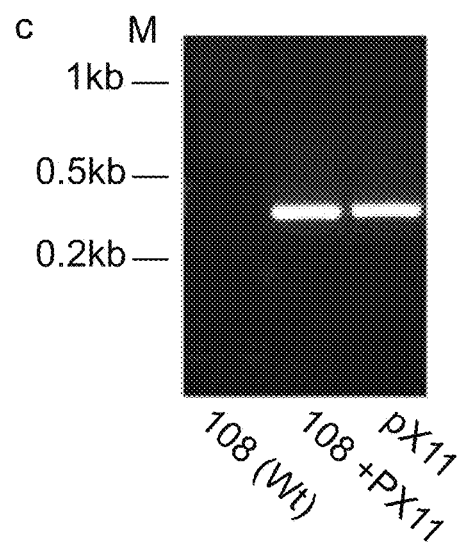

Young 3-5 weeks old *Cannabis* plants immerging from cuttings were left to grow until at list two nodes were observed, then the stem was cut at the same way the seedlings were, leaving only one leaf. The wound was spread with the regeneration paste and the plants were left at 16 h light, allowing the plant to regenerate (FIG. 9).

acterization and GUS and betalains expression analysis were done using PCR (FIGS. 10A-10C to 11A-11C).

Example 4

Regeneration of *Cannabis sativa* Via Somatic Embryogenesis

Materials and Methods

Leaf segments from tissue culture grown on the solid medium (1.5 cm diameter and 4-5 cm long) of two *Cannabis*

TABLE 5

The effects of different hormones by spreading the "regeneration paste" on various *cannabis* strains: recovery from injury is indicated as recovery percentage.

| cultivar | t001 Spreading 4000 mg/l BAP | t002 Spreading 2000 mg/l BAP | t003 Spreading 50 mg/l BAP | t004 Spreading 50 mg/l BAP | t005 Spreading 400 mg/l BAP 50 mg/l IBA | t006 Spreading 100 mg/l ZEATIN 50 mg/l IBA | t007 Spreading 1000 mg/l ZEATIN | t008 Spreading 2000 mg/l ZEATIN | t009 Spreading 500 mg/l ZEATIN + 1000 mg/l IAA | t010 Spreading MS 0222 2 mg/l TDZ 2 mg/l IBA |
|---|---|---|---|---|---|---|---|---|---|---|
| #102 | ≥70% Mortality | ≥70% Mortality | 10% recovery 3% M 97% N | ≥70% Mortality | ≥70% Mortality | ≥70% Mortality | Not tasted | Not tasted | Not tasted | ≥70% Mortality |
| #106 | Not tasted | Not tasted | Not tasted | Not tasted | 50% recovery 10% M 35% R 55% N | 75% recovery 45% R 15% M 30% C 10% N | Not tasted | Not tasted | Not tasted | 50% recovery 40% R 30% M 25% C 5% N |
| #107 | Not tasted | Not tasted | Not tasted | Not tasted | 50% recovery 55% R 37% C 8% N | 50% recovery 50% R 20% C 30% N | Not tasted | Not tasted | Not tasted | 25% recovery 100% N |
| #108 | Not tasted | Not tasted | Not tasted | 72% recovery 9% R 6% M 85% N | Not tasted | Not tasted | 80% recovery 71% R 7% M 22% N | 80% recovery 30% R 30% M 40% N | 80% recovery 8% R 28% M 60% C 4% N | Not tasted |

R(regenerate),
M(meristem),
C(callus),
N(no change).

In Planta Microencapsulation *Agrobacterium* Transformation

In planta *Agrobacterium* application is complicated due to poor attachment of the bacteria to the wounding area. For in planta transformation, *Agrobacterium* strain EHA 105 harboring the different binary plasmids were mixed with emulsifier paste to enhance attachment to the cut plant surface. *Agrobacterium* was grown and activated as described in materials and methods, and then it was mixed with lanolin nano-emulsifier usually at 3:4 (v/v) ratio. The resultant paste was spread on the cutting up to 24 h after the wounding. *Agrobacterium* strain EHA 105 harboring the binary vector pME504 that carries the genes for p-glucuronidase (GUS) and neomycin phosphotransferase (npt II), or the plasmid pX 11 carrying the nptII and betalain genes were used for transformation. The proof of transformability in the T0 generation was indicated by the GUS histochemical analysis of the seedlings, ten days after co-cultivation and was further confirmed by PCR analysis and typical betalains red leaf expression (FIGS. 10A-10C to 11A-11C). Molecular charcultivars (108 and 201) were used. Innermost leaf whorls were cut obliquely (0.5-1.0 cm), injured with sharp scalpel blade in order to achieve callus initiation. Leaf segment, were used as explant for inoculation on MS medium (Murashige and Skoog 1962) supplemented with 2,4-D (4.0 mg/L) and kinetin [Kin] (0.5 mg/L). After 2-3 weeks the cultures were incubated at 25±2 C at 70-80% humidity in dark in liquid Gamborg B5 medium supplemented with 6% sucrose and different plant hormones (Table 1). The media was refreshed every three weeks.

Leaf segments from tissue culture from two different genotypes (108 and 201) have been used as primary explants. The explants were chopped to small pieces (as less as 0.5 mm) and cultivated in liquid Gamborg B5 medium supplemented with 6% sucrose and different plant hormones (Table 1). The media were refreshed every three weeks.

Results

*Cannabis sativa* Micropropagation Via Somatic Embryogenesis—Effect of Cannabidiol (CBD) with CPPU Microemulsion The first globular shaped embryos were observed 4 weeks after initiation.

CPPU (at a concentration of 10 mg/l) alone or as a CBD-CPPU microemulsion was essential for the embryo initiation. Low amounts of embryos were generated in media with 2iP-3 mg/l CPPU but the addition of the CBD-CPPU microemulsion dramatically increased somatic embryogenesis. The embryos were cultivated on gyratory shaker at dark.

TABLE 6

Type of the hormones used in Somatic embryo initiation in *cannabis* explants:

| Hormone | Concentration [mg/l] |
| --- | --- |
| CBD-CPPU | 10 |
| CPPU | 10 |
| 2.4D | |
| 2iP | 3 |
| Kinetin | 2 |
| Zeatin | 1 |
| TDZ | 2 |
| Picloram | 12.5 |
| Dihydric zeatin | 2 |
| Kinetin ribosid | 2 |
| BAP | 1 |

The initiated suspension cultures along with embryos in globular stage (FIGS. 12A-12B) were sub-cultured in the same medium for three weeks. Part of the cultures was transferred to B5 Gamborg media, supplemented with different hormones/chemicals (Table 2) to provoke embryo elongation and further development. The cultures were transferred to fresh media every three weeks.

TABLE 7

Different supplements were used in hemp somatic embryo development:

| Supplements to B5 media for E development | Concentration [mg/l] |
| --- | --- |
| CPPU | 10 |
| CPPU | 20 |
| CPPU and 6% sucrose (instead of 3%) | 10 |
| CPPU and 6% sucrose (instead of 3%) | 20 |
| CBD-CPPU and 6% sucrose (instead of 3%) | 20 |
| 2iP | 3 |
| TDZ/Piclorame | 2/12.5 |
| PEG 4000 | 1% |

Some of the somatic embryos after the second sub-culture on B5 media, supplemented with CBD-CPPU and 6% sucrose (instead of 3%) underwent to torpedo shaped embryos.

With some of the torpedo shaped embryos, after the third subculture on B5 media supplemented with CBD-CPPU and 6% sucrose, plants regeneration occurred in the liquid media (FIGS. 13A-13C).

Example 5

Protoplasts Isolation and Transformation in Three Different *Cannabis* Cultivars Protoplasts were successfully isolated in all tested *Cannabis* cultivars. The combination and concentration of the enzymes, as well as the time for treatment were optimized. Presence and optionally concentration (0.5 M) of mannitol were important for protoplast culture. About 4% of the protoplasts survived after 48 hours cultivation in liquid culture. Some of the protoplasts developed cell wall—less than 1%. Protoplast transformation was also established.

Material and Methods

Protoplast Isolation

Seeds were sterilized with 1.5% sodium hypochlorite for 20 min, followed by a series of washes with sterile water. Seeds were left to germinate on sterile MS media and cotyledons were harvested when emerged. Cotyledons were cut to fine pieces and incubated in a cell wall degrading solution containing 1.5% cellulose, 0.5% macerozyme, 0.4% mannitol, 20 mM KCl, 20 mM MES, 10 mM $CaCl_2$) and 0.1% BSA, placed in vacuum for 10 min and then shaken for 5 h at 50 rpm. The protoplasts were then filtered through a 100 μm mesh, diluted with 1 volume of W5 (150 mM NaCl, 125 mM $CaCl_2$), 5 mM KCl, and 2 mM MES) and pelleted by centrifugation (Room temperature, 2 min at 300 g). The protoplasts were re-suspended in W5 solution and incubated for 30 min on ice, before being centrifuged again and re-suspended in 100 μl of MMg solution containing, 0.4 M mannitol and 15 mM MgCl2.

Protoplast Transformation

Red fluorescent protein (RFP), a visual marker, in plasmid DNA (5-20 μg) was added to protoplasts and an equal volume of 40% PEG solution (in 0.2 M mannitol and 0.1 M $CaCl_2$)). The mixture was incubated for 15-30 min. Two volumes of W5 were added to each sample, centrifuged for 2 min, re-suspended in 1 ml of W5, and then incubated at room temperature for 16-24 hr.

Results

Figure 14:
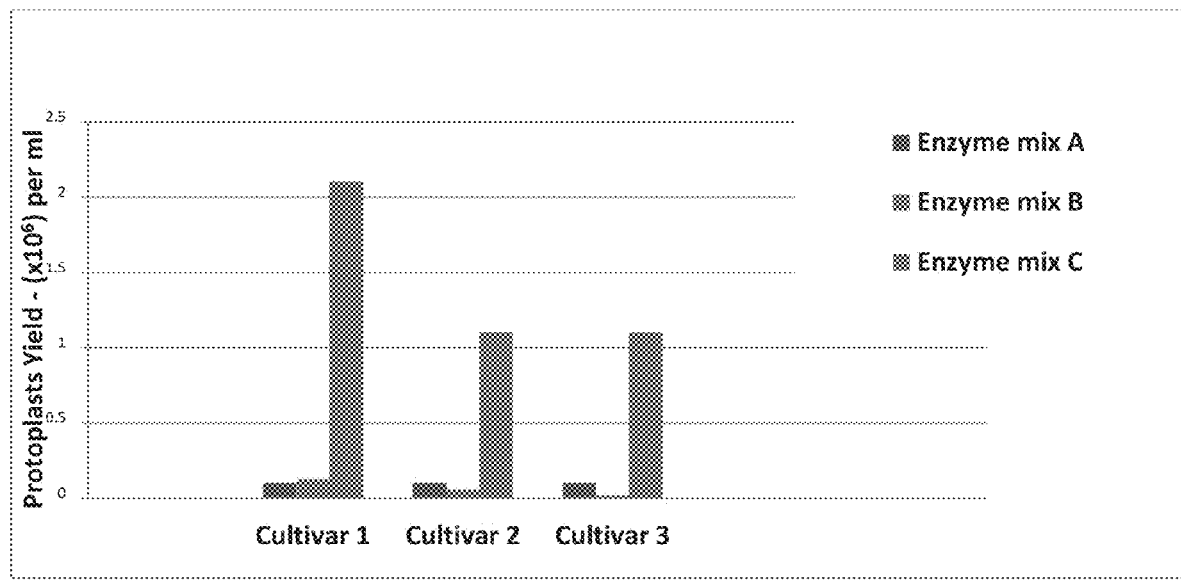
FIG. 14 is a graph showing mesophyll protoplasts yield (×10$^6$) in three different cultivars of *Cannabis sativa* under a variety of enzymatic treatments.
Figures 15A, 15B:
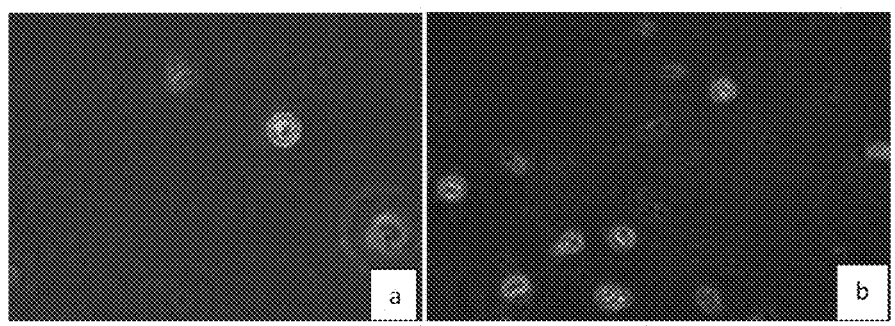
FIGS. 15A-15B show *cannabis* protoplasts isolated after enzymatic treatment (complex of enzymes C).

Three different combinations of enzymes (Table 8) were tested for the ability to isolate protoplasts from three cultivars of *Cannabis sativa* (cultivar 1, 2, 3 are 201, 202, 203). Leaf explants were enzymatically treated either for 4 hours or for 17 hours. Only one of the enzyme's combination—enzyme mix C, was efficient (FIG. 14). Protoplasts were isolated from all three tested cultivars. The cultivars were differing in the yield of the protoplasts (FIG. 14). Maximum protoplasts were harvested from *cannabis* cultivar 1 (Protoplast concentration was $2.2 \times 10^6$/ml). The protocol for protoplasts isolation was optimized regarding the medium composition—concentrations of Mannitol, $CaCl_2$) and PVP pretreatment. The isolated protoplasts (FIGS. 15A-15B) were filtered through a 100 μm mesh, diluted with 1 volume of W5 (150 mM NaCl, 125 mM $CaCl_2$), 5 mM KCl, and 2 mM MES) and pelleted by centrifugation. Purified protoplasts were cultivated under dark condition in droplets double layer (liquid/solid) culture.

TABLE 8

| Combination of enzymes used in hemp protoplasts | |
| --- | --- |
| A | Cellulisine - 4% |
| | Driselase - 0.3% |
| B | Cellulose Onozuka R-10 - 2% |
| | Hemicellulose - 1% |
| | Driselase - 0.3% |
| C | Cellulose Onozuka R-10 - 1.5% |
| | Hemicellulose - 1% |
| | Macerozyme R-10 - 0.4% |

Protoplast Transformation

As mentioned above, an efficient *cannabis* protoplast isolation protocol was developed using different plant tissues. FIG. 16 shows protoplast transformation using the RFP gene (Chung, Sang-Min, Ellen L. Frankman, and Tzvi Tzfira. "A versatile vector system for multiple gene expression in plants." *Trends in plant science* 10.8 (2005): 357-361).).

This protoplast isolation protocol allowed protoplast isolation from 10 different *cannabis* strains that were clonally propagated in culture.

Example 6

*Cannabis* Pollen Transformation

Most of the current transformation methods require plant regeneration from tissue culture, involving long and laborious processes. In order to overcome the constraints of in-vitro tissue culture regeneration, pollen-mediated transformation methods are considered to be promising alternatives. Pollen release active DNA to the ovary during pollination and fertilization. Transgenic seeds can be directly generated through pollination with exogenous DNA-transformed pollen. In pollen magnetofection technology, positively charged, polyethyleneimine-coated $Fe_3O_4$ MNPs (Magnetic Nano Particles) are used as DNA carriers for binding and condensing with electric negative DNA to form MNP-DNA complexes. Here is shown for the first time positive *Cannabis* pollen transformation using the GUS reporter gene, by employing the magnetofection technology.

Material and Methods

Plasmid

For *Cannabis* pollen transformation, the binary vector CsUBQ::GUS was used. The plasmid carries the GUS reporter gene under the *Cannabis Sativa* UBQ 10 promoter.

Pollen

Pollen collected from four different samples in two replicates was used:
1. Fresh, 'malenized' from genotype 213;
2. One-month-old, 'malenized' from genotype 212;
3. Two-month-old, male from genotype 108;
4. Two-month-old, 'malenized' from genotype 216;

Samples were tested for viability prior to transformation.

Transformation 1 ug of plasmid was left to bind with MNP's (MAGBIO, USA) for 30 min at room temperature, prior to adding the transformation media: 10 g-40 g Sucrose, $H_3BO_3$—10.3 mg, $KNO_3$—2.3 mg, $Ca(NO_3)_2$—10.3 mg, $MnSO_4$—10.3 mg, $MgSO_4$ 7H2O—10.3 mg, $GA_3$—3 mg, $H_2O$ up to 100 ml.

Pollen (1-10 million grains) added to the Media containing bound MNP's—plasmid and left on a magnet (Chemicell) for 30 min at room temp and dried in 30° C. for 30 min.

Results

*Cannabis* pollen characteristics and imaging. *Cannabis* is wind pollinated and therefore, its pollen grain diameter is about 25 um and there are about half million grains per 1 mg of pollen (data not shown). *Cannabis* pollen was examined under light microscope in the presence of Safranine O (FIG. 17A) and it clearly shows apertures where the pollen wall is absent or reduced Pollen viability was confirmed by incubating pollen grains on germination media and after 18 h pollen tubes were observed (FIG. 17B).

Exogenous Gene Expression in *Cannabis* Pollen

In order to test whether exogenous genes can be expressed in pollen, a reporter gene in CsUBQ::GUS plasmid was transformed into *cannabis* pollen using the MNPs. If the GUS gene is successfully transformed, the GUS protein (β-Glucuronidase) will be expressed, which can then be stained blue by X-gluc solution. Optical microscopy showed that pollen grains were stained blue by X-gluc, suggesting that MNP-DNA complexes did not inhibit transformation function and that the GUS gene was indeed successfully transformed and expressed (FIG. 17C).

Example 7

Identification and Isolation of the CsBBM and CsSERK1 Genes

In order to identify the homologous genes of the BBM and SERK1 genes in *Cannabis*, blast analysis was performed using the *Arabidopsis* BBM and SERK1 genes (SEQ ID NOs: 3 and 7) as a bait. The sequences of the genes that show the highest homology to these genes are shown in FIG. 18. To isolate the CsBBM and CsSERK1 genes, total RNA was extracted from *Cannabis* calli, followed by cDNA synthesis. Then, candidate genes were isolated from cDNA generated out of RNA from regenerating *Cannabis* callus using the primers 5'ATGAGTATTATTACTAATGA-TAGTAATCTCAG3' (SEQ ID NO: 16) and TTATTC-CATGCCGAATATTGGTGTT3' (SEQ ID NO: 17) for CsBBM, and 5'ATGGAAGGTGATGCCTTGCATAGTC3' (SEQ ID NO: 18) and 5'TTACCTCGGACCAGA-TAACTCGACC3' (SEQ ID NO: 19) for CsSERK1.

These cDNA were amplified using specific primers for the CsBBM and CsSERK1 genes and cloned into pCAMBIA binary vectors under the control of a constitutive 35S promoter and fused to an expression cassette of the CAS9 gene, under the control of the CsUBIQUITIN10 promoter (SEQ ID NO: 11, FIG. 19).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. A method of in-vitro propagating *cannabis* plant, the method comprising:
   (a) culturing a *cannabis* explant comprising a meristem on a culture medium; and subsequently
   (b) culturing said *cannabis* explant in a liquid medium, wherein at least a portion of a time period in said liquid medium is with a cell wall disruption agent is selected from the group consisting of pectinase, cutinase and a combination thereof; and subsequently
   (c) culturing said *cannabis* explant under conditions which consist of a solid medium without said cell wall disrupting agent; wherein steps (a)-(c) are performed in a consecutive manner and repeated at least once until emergence of leaves suitable for regeneration.

2. The method of claim 1, further comprising sterilizing said *cannabis* explant prior to step (a).

3. The method of claim 1, wherein said step (b) is performed while shaking.

4. The method of claim 1, wherein step (a) is performed for 7-30 days.

5. The method of claim 1, wherein said meristem is an apical meristem or an axillary meristem.

6. The method of claim 1, wherein said explant comprising said meristem is of a stem.

7. The method of claim 1, wherein said *cannabis* explant is from a seedling.

8. The method of claim 1, wherein said *cannabis* explant is from a mature plant.

9. The method of claim 1, further comprising removing leaves and necrotic regions from said *cannabis* explant between steps (a) to (c).

10. The method of claim 1, wherein said cell wall disrupting agent is provided at a sub-lethal concentration.

11. The method of claim 1, wherein said emergence of leaves suitable for regeneration is manifested by rooting and acclimatization.

* * * * *

SEQUENCE LISTING

```
Sequence total quantity: 19
SEQ ID NO: 1          moltype = DNA  length = 2292
FEATURE               Location/Qualifiers
source                1..2292
                      mol_type = genomic DNA
```

```
                        organism = Cannabis sativa
SEQUENCE: 1
gtttgggttt ggggttgggg taggaattttt ttgtgatgtt gtgtttgggt gtggcatacc   60
atttggatct aaggttttttg gttacttaga ctaaaatagc aagggaggaa atatggaaag  120
gaagaagctt tggtggtctt cattttgcct ttggttgatt ttggtagttc atccttttatg  180
ggtgattatg gtatctgcta atatggaagg tgatgccttg catagtctga ggtccaattt  240
acaggatccc aacaatgttc tgcagagttg ggatcccacc cttgtaaacc cgtgtacatg  300
gtttcatgtc acttgcaaca atgataatag tgtgataagg gttgatcttg gaaatgcagc  360
tttgtctggt caacttgttc cacagcttgg ccttctcaag aatttacaat atttggaact  420
ttacagtaat aacattagtg gaacaattcc tagtgatttg gggaatttga ccagcttggt  480
tagcttggat ctgtatttga atagtttttac tggtcctatc ccggacacct tgggcaagtt  540
gtcaaaatta agatttcttc ggcttaacaa caatagtctg acgggtccaa ttcctatgtc  600
gttgaccaac atcacctcac tgcaagtgct ggatctgtca ataacaaat taaccggaga  660
ggttccagac aatggctcgt tttctttatt cactcccatc agttttgcta ataacttaaa  720
tctatgtggc ccggttactg gacgaccctg cccaggatcc cccccatttt cacctcctcc  780
tccttttgtc ccaccacccc caatttcagt cccaggtgga aatagtgcga ctggggctat  840
tgctggtgga gttgctgctg tgctgctttt attatttgct gctcctgcta ttgcatttgc  900
ttggtggcgt cgaaggaagc cacaagaatt tttctttgat gtaccgctg aggaggatcc  960
tgaagttcat cttgggcagc ttaaaaggtt ttcgttgcga gaattacaag tggcaactga 1020
tagttttagc aacaaaaaca ttctgggacg gggtggattt ggtaaggtct acaaaggtcg 1080
ccttgcagat ggttctttgg ttgctgtaaa gagactgaaa aagagcgta cacctggtgg 1140
cgagttgcag tttcaaacag aagtagagat gatcagtatg gctgtcatc ggaatcttct 1200
tcgattacgt gggttctgta tgacaccaac tgaacgatta cttgtttatc cttatatggc 1260
taatgggagt gttgcctcat gcttaagaga acggccgcca caccaactgc ctcttgattg 1320
gcctactagg aaacgaatag cattgggttc tgcaaggggt cttcgttatt tgcatgatca 1380
ttgcgatcca aaaattattc atcgtgatgt gaaagctgat aatatttttgt tggatgagga 1440
gtttgaagca gttgttggag atttcggttt ggctaaactt atggactaca aggcactca 1500
tgttactaca gctgtacgag gcacaatcgg gcatattgct ccagagtacc tctctaccgg 1560
gaagtcttct gagaaaaccg atgtgtttgg ctatggaatc atgcttttgg aattaattac 1620
tggacagaga gcttttgatc ttgctcggct tgcaaatgat gatgatgtca tgttgctcga 1680
ctgggtgaaa ggactactga aagagaagaa gttggaaatg ctggtggacc ccgatcttca 1740
aaagaactac atagaatccg aagtagagca gcttattcag gttgcactgc tctgcacaca 1800
aggttctccc atggaccgac caaagatgtc agaggtggtg agaatgctcg aaggcgatgg 1860
cttggccgag agatgggatg aatggcaaaa agtggaagta ctacgacaag aagtcgaact 1920
agcccctcat ccaaactcag actgatagt agactcaacc gaaaacttgc atgcggtcga 1980
gttatctggt ccgaggtaac cctggcacaa tagaaagtgg aagaaaaagg gaatttactt 2040
acaacttaat tttttttaat taattataat agctttttt tcttcttctt aatgaccata 2100
atctgattaa tgtctctttg taagtccatt ctgcattgta ttcgttacat ttgtgcatat 2160
gagagtcgca ttggtaaggt gcaaatttgt attgtctgct gcagtgtgac aaaagccata 2220
gatgtttta taatatga agctgtggca gttttatct tttgttcact gcagcagaca 2280
atacaaattt gc                                                    2292

SEQ ID NO: 2              moltype = DNA  length = 1661
FEATURE                   Location/Qualifiers
source                    1..1661
                          mol_type = genomic DNA
                          organism = Cannabis sativa
SEQUENCE: 2
aataataata ataataatat tatgagtatt attactaatg atagtaatct cagttgccag   60
ctggaagcgc cgccgtctgc ggtggctccg gtgtcgtcta agaagaccgt tgacactttt  120
ggtcaacgta cctctatata ccgtggtgtt actcgacata gatggactgg tagatatgaa  180
gctcatttgt gggacaacag ttgccgaaga gaaggccaga gtagaaaagg gcgacaagtt  240
tatttgggtg gatatgataa agaagaaaag gcagcaagag cttatgattt ggctgccctt  300
aagtactggg gtcctaccac cactacaaat tttgcagtgt ctaattacga aaaagaatta  360
gaagatatga cgaacatgac taggcaagaa ttcgttgctt cacttcgaag gaaaagtagt  420
ggattttcta gaggagcttc aatatacaga ggcgtcacaa ggcaccacca acatggtcga  480
tggcaggcaa gaattggaag agtagcagga aacaaagatc tctaccttgg caccttttagc  540
acacaagaag aagcagccga ggcatacgac atcgcggcga taaaattccg aggcctaaac  600
gccgtaacaa acttcgacat gagccgttac gacgttaaaa gcatagccaa ctctaatctc  660
cccgttggag aatgtcaaa caacaccaaa cttccaaaa cctcaccga acgggcgatt  720
gacaacctat catcgcccgc ttcatcatcc ctcgtcgcct tctcctcctc ggccaccacc  780
aacaaccaaca acacaacacc caacaacaa caacaacaac aaatgtcctc caatctaagc  840
tttactcttc ccatcaaaca agacctaaca acaacgacaa catcgtcaac ggattattgg  900
tcaaacattt tcggtttcca aaaccctaac cctagtagta ctactcctcc  960
ttattgttgg gccataatag tcacaacctc tcggccacat caactaatgc aacaacaact 1020
acaacaacaa caagtaatgg agggtattat ggtaatttca tcgagtcaat ttctaataat 1080
aataataata atactaactt gggttatgga tcaggattaa gtagctggat tagtaatagt 1140
aatcataata ttaacggagg gagtagtaat agtagtagta ttcataatca tcttcatcat 1200
catcatcatc atgaagttgt tcatgcgaaa caacctagtc tttttcaaac accaatattc 1260
ggcatggaat aataatgatg atgattttc tcgcacactt gttggaaaac tactggcacg 1320
tgggaatctg tggtgtttga atttgcatgg aaaagggagc tagggttgtt gttgttgtta 1380
ttgtaataat aataataata tggtggaaac tgacaatatt catcataata ttattttca 1440
tgagagatga gaatgtagta gtgaaatagc tagtactaac tgaagttggg ttcttttagg 1500
gaccatgttt ttacttttt attatttt tgcttttc ttttcctttt agtttcatta 1560
ctagatctac tgacattatt attattctag gtgttaagga aaggaatcct ttttgtaatc 1620
cttagttttt ttcatatata ttatataaat gcaccttctt c                    1661

SEQ ID NO: 3              moltype = AA  length = 522
FEATURE                   Location/Qualifiers
```

```
                                                -continued source                  1..522
                        mol_type = protein
                        organism = Arabidopsis thaliana
SEQUENCE: 3
MNQTQRWGSL CFLSIDWDIN GGACNNINNN EQNGPKLENF LGRTTTIYNT NETVVDGNGD    60
CGGGDGGGGG SLGLSMIKTW LSNHSVANAN HQDNGNGARG LSLSMNSSTS DSNNYNNNDD   120
VVQEKTIVDV VETTPKKTIE SFGQRTSIYR GVTRHRWTGR YEAHLWDNSC KREGQTRKGR   180
QVYLGGYDKE EKAARAYDLA ALKYWGTTTT TNFPLSEYEK EVEEMKHMTR QEYVASLRRK   240
SSGFSRGASI YRGVTRHHQH GRWQARIGRV AGNKDLYLGT FGTQEEAAEA YDIAAIKFRG   300
LSAVTNFDMN RYNVKAILES PSLPIGSSAK RLKDVNNPVP AMMISNNVSE SANNVSGWQN   360
TAFQHHQGMD LSLLQQQQER YVGYYNGGNL STESTRVCFK QEEEQQHFLR NSPSHMTNVD   420
HHSSTSDDSV TVCGNVVSYG GYQGFAIPVG TSVNYDPFTA AEIAYNARNH YYYAQHQQQQ   480
QIQQSPGGDF PVAISNNHSS NMYFHGEGGG EGAPTFSVWN DT                     522

SEQ ID NO: 4            moltype = AA   length = 579
FEATURE                 Location/Qualifiers
source                  1..579
                        mol_type = protein
                        organism = Brassica napus
SEQUENCE: 4
MNNNWLGFSL SPYEQNHHRK DVYSSTTTTV VDVAGEYCYD PTAASDESSA IQTSFPSPFG    60
VVVDAFTRDN NSHSRDWDIN GCACNNIHND EQDGPKLENF LGRTTTIYNT NENVGDGSGS   120
GCYGGGDGGG GSLGLSMIKT WLRNQPVDNV DNQENGNAAK GLSLSMNSST SCDNNNDSNN   180
NVVAQGKTID DSVEATPKKT IESFGQRTSI YRGVTRHRWT GRYEAHLWDN SCKREGQTRK   240
GRQVYLGGYD KEEKAARAYD LAALKYWGTT TTTNFPMSEY EKEVEEMKHM TRQEYVASLR   300
RKSSGFSRGA SIYRGVTRHH QHGRWQARIG RVAGNKDLYL GTFGTQEEAA EAYDIAAIKF   360
RGLTAVTNFD MNRYNVKAIL ESPSLPIGSA AKRLKEANRP VPSMMMISNN VSESENSASG   420
WQNAAVQHHQ GVDLSLLHQH QERYNGYYYN GGNLSSESAR ACFKQEDDQH HPFLSNTQSLM   480
TNIDHQSSVS DDSVTVCGNV VGYGGYQGFA APVNCDAYAA SEFDYNARNH YYFAQQQQTQ   540
QSPGGDFPAA MTNNVGSNMY YHGEGGGEVA PTFTVWNDN                         579

SEQ ID NO: 5            moltype = AA   length = 706
FEATURE                 Location/Qualifiers
source                  1..706
                        mol_type = protein
                        organism = Zea mays
SEQUENCE: 5
MATVNNWLAF SLSPQELPPS QTTDSTLISA ATADHVSGDV CFNIPQDWSM RGSELSALVA    60
EPKLEDFLGG ISFSEQHHKS NCNLIPSTSS TVCYASSAAS TGYHHQLYQP TSSALHFADS   120
VMVASSAGVH DGGSMLSAAA ANGVAGAASA NGGGIGLSMI KNWLRSQPAP MQPRAAAAEG   180
AQGLSLSMNM AGTTQGAAGM PLLAGERARA PESVSTSAQG GAVVVTAPKE DSGGSGVAGA   240
LVAVSTDTGG SGGASADNTA RKTVDTFGQR TSIYRGVTRH RWTGRYEAHL WDNSCRREGQ   300
TRKGRQGGYD KEEKAARAYD LAALKYWGAT TTTNFPVSNY EKELEDMKHM TRQEFVASLR   360
RKSSGFSRGA SIYRGVTRHH QHGRWQARIG RVAGNKDLYL GTFSTQEEAA EAYDIAAIKF   420
RGLNAVTNFD MSRYDVKSIL DSSALPIGSA AKRLKEAEAA ASAQHHHAGV VSYDVGRIAS   480
QLGDGGALAA AYGAHYGAA WPTIAFQPGA ATTGLYHPYA QQPMRGGGWC KQEQDHAVIA    540
AAHSLQDLHH LNLGAAGAHD FFSAGQQAAA AAAMHGLASI DSASLEHSTG SNSVVYNGGV   600
GDSNGASAVG SGGGYMMPMS AAGATTTSAM VSHEQMHARA YDEAKQAAQM GYESYLVNAE   660
NNGGGRMSAW GTVVSAAAAA AASSNDNIAA DVGHGGAQLF SVWNDT                 706

SEQ ID NO: 6            moltype = AA   length = 416
FEATURE                 Location/Qualifiers
source                  1..416
                        mol_type = protein
                        organism = Cannabis sativa
SEQUENCE: 6
MSIITNDSNL SCQLEAPPSA VAPVSSKKTV DTFGQRTSIY RGVTRHRWTG RYEAHLWDNS    60
CRREGQSRKG RQVYLGGYDK EEKAARAYDL AALKYWGPTT TTNFAVSNYE KELEDMTNMT   120
RQEFVASLRR KSSGFSRGAS IYRGVTRHHQ HGRWQARIGR VAGNKDLYLG TFSTQEEAEA   180
AYDIAAIKFR GLNAVTNFDM SRYDVKSIAN SNLPVGGMSN NTKLSKTSPE RAIDNLSSPA   240
SSSLVAFSSS ATTNNNNTTP QQQQQQQMSS NLSFTLPIKQ DLTTTTTSST DYWSNIFGFQ   300
NPNPSSTTST TPSLLLGHNS HNLSATSTNA TTTTTTTSNG GYYGNFIESI SNNNNNNTNL   360
GYGSGLSSWI SNSNHNINGG SSNSSNVHNH LHHHHHHEVV HAKQPSLFQT PIFGME       416

SEQ ID NO: 7            moltype = AA   length = 625
FEATURE                 Location/Qualifiers
source                  1..625
                        mol_type = protein
                        organism = Arabidopsis thaliana
SEQUENCE: 7
MESSYVVFIL LSLILLPNHS LWLASANLEG DALHTLRVTL VDPNNVLQSW DPTLVNPCTW    60
FHVTCNNENS VIRVDLGNAE LSGHLVPELG VLKNLQYLEL YSNNITGPIP SNLGNLTNLV   120
SLDLYLNSFS GPIPESLGKL SKLRFLRLNN NSLTGSIPMS LTNITTLQVL DLSNNRLSGS   180
VPDNGSFSLF TPISFANNLD LCGPVTSHPC PGSPPFSPPP PFIQPPPVST PSGYGITGAI   240
AGGVAAGAAL LFAAPAIAFA WWRRRKPLDI FFDVPAEEDP EVHLGQLKRF SLRELQVASD   300
GFSNKNILGR GGFGKVYKGR LADGTLVAVK RLKEERTPGG ELQFQTEVEM ISMAVHRNLL   360
RLRGFCMTPT ERLLVYPYMA NGSVASCLRE RPPSQPPLDW PTRKRIALGS ARGLSYLHDH   420
CDPKIIHRDV KAANILLDEE FEAVVGDFGL AKLMDYKDTH VTTAVRGTIG HIAPEYLSTG   480
KSSEKTDVFG YGIMLLELIT GQRAFDLARL ANDDDVMLLD WVKGLLKEKK LEMLVDPDLQ   540
```

```
TNYEERELEQ VIQVALLCTQ GSPMERPKMS EVVRMLEGDG LAEKWDEWQK VEILREEIDL  600
SPNPNSDWIL DSTYNLHAVE LSGPR                                       625

SEQ ID NO: 8            moltype = AA  length = 621
FEATURE                 Location/Qualifiers
source                  1..621
                        mol_type = protein
                        organism = Brassica napus
SEQUENCE: 8
METIHVAFIL LSLILLPNHA SANLEGDALH TLRVTLVDPN NVLQSWDPTL VNPCTWFHVT  60
CNNENSVIRV DLGNAELSGH LVPELGVLKN LQYLELYSNN ITGPIPSNLG NLTNLVSLDL  120
YLNSFTGPIP ESLGKLSKLR FLRLNNNTLT GSIPMSLTNI TTLQVLDLSN NQLSGSVPDN  180
GSFSLFTPIS FANNLDLCGP VTSHPCPGSP PFSPPPPFIP PPPVSTPSGY GITGAIAGGV  240
AAGAALLFAA PAIAFAWWRR RKPHDIFFDV PAEEDPEVHL GQLKRFSLRE LQVASDGFSN  300
KNILGRGGFG KVYKGRLADG TLVAVKRLKE ERTPGGELQF QTEVEMISMA VHRNLLRLRG  360
FCMTPTERLL VYPYMANGSV ASCLRERPPS QPPLDWPTRK RIALGSARGL SYLHDHCDPK  420
IIHRDVKAAN ILLDEDFEAV VGDFGLAKLM DYKDTHVTTA VRGTIGHIAP EYLSTGKSSE  480
KTDVFGYGIM LLELITGQRA FDLARLANDD DVMLLDWVKG LLKEKKLEML VDPDLQTNYE  540
ERELEQVIQV ALLCTQGSPM ERPKMSEVVR MLEGDGLAER WDEWQKVEIL REDVDLSPNL  600
HSDWIVDSTY NLHAVELSGP R                                           621

SEQ ID NO: 9            moltype = AA  length = 629
FEATURE                 Location/Qualifiers
source                  1..629
                        mol_type = protein
                        organism = Solanum lycopersicum
SEQUENCE: 9
MVKVMEKDTV VVSLVVWLIL VVYHLKLIYA NMEGDAHLSL RVNLQDPNNV LQSWDPTLVN  60
PCTWFHVTCN NDNSVIRVDL GNAALSGLLV PQLGLLKNLQ YLELYSNNIS GLIPSDLGNL  120
TNLVSLDLYL NNFVGPIPDS LGKLSKLRFL RLNNNSLTGN IPMSLTNISS LQVLDLSNNR  180
LSGAVPDNGS FSLFTPISFA NNLDLCGPVT GRPCPGSPPF SPPPPFVPPP PISAPGGNGA  240
TGAIAGGVAA GAALLFAAPA IAFAWWRRRK PQEYLFDVPA EEDPEVHLGQ LKRFSLRELQ  300
VATDSFSNKN ILGRGGFGKV YKGRLADGSL VAVKRLKEER TPGGELQFQT EVEMISMAVH  360
RNLLRLRGFC MTPTERLLVY PYMANGSVAS CLRERPPSEP PLDWPTRKRI ALGSARGLSY  420
LHDHCDPKII HRDVKAANIL LDEEFEAVVG DFGLAKLMDY KDTHVTTAVR GTIGHIAPEY  480
LSTGKSSEKT DVFGYGIMLL ELITGQRAFD LARLANDDDV MLLDWVKGLL KEKKLEMLVD  540
PDLQNKYVEA EVEQLIQVAL LCTQSNPMDR PKMSEVVRML EGDGLAERWD EWQKVEVLRQ  600
EVELAPHPGS DWLVDSTENL HAVELSGPR                                   629

SEQ ID NO: 10           moltype = AA  length = 598
FEATURE                 Location/Qualifiers
source                  1..598
                        mol_type = protein
                        organism = Cannabis sativa
SEQUENCE: 10
MEGDALHSLR SNLQDPNNVL QSWDPTLVNP CTWFHVTCNN DNSVIRVDLG NAALSGQLVP  60
QLGLLKNLQY LELYSNNISG TIPSDLGNLT SLVSLDLYLN SFTGPIPDTL GKLSKLRFLR  120
LNNNSLTGPI PMSLTNITSL QVLDLSNNKL TGEVPDNGSF SLFTPISFAN NLNLCGPVTG  180
RPCPGSPPFS PPPPFVPPPP ISVPGGNSAT GAIAGGVAAG AALLFAAPAI AFAWWRRRKP  240
QEFFFDVPAE EDPEVHLGQL KRFSLRELQV ATDSFSNKNI LGRGGFGKVY KGRLADGSLV  300
AVKRLKEERT PGGELQFQTE VEMISMAVHR NLLRLRGFCM TPTERLLVYP YMANGSVASC  360
LRERPPHQLP LDWPTRKRIA LGSARGLSYL HDHCDPKIIH RDVKAANILL DEEFEAVVGD  420
FGLAKLMDYK DTHVTTAVRG TIGHIAPEYL STGKSSEKTD VFGYGIMLLE LITGQRAFDL  480
ARLANDDDVM LLDWVKGLLK EKKLEMLVDP DLQKNYIESE VEQLIQVALL CTQGSPMDRP  540
KMSEVVRMLE GDGLAERWDE WQKVEVLRQE VELAPHPNSD WIVDSTENLH AVELSGPR    598

SEQ ID NO: 11           moltype = DNA  length = 750
FEATURE                 Location/Qualifiers
misc_feature            1..750
                        note = CsUBIQUITIN10 promoter nucleic acid sequence
source                  1..750
                        mol_type = other DNA
                        organism = synthetic construct
SEQUENCE: 11
ccgtgaaaac ttaacacagt acacaatatt tttgagcccc atagtaaaaa aataaaaaag  60
ttaaaaattt gagtatgtgg cgtaaaaatt ccatatatat ggaatatgga agatatatag  120
aagggataat tacaccacat cgtgaaattt cttagttttt tactttcata ctgtggggcg  180
gaatttttt caaaaatact gtgtgagttt tatactggtt aagttttcac tgttgttcta  240
cggttgtttt tagttgttcc actgttattt ttagttgttc tgttttgtat tctattttgt  300
attctattgt tgttttataa aaatatagta ttttttaaaa aatttccggg tgacagtatt  360
tttataaatt ttcttatata aaactaaacc taataacgag gcccagccca gtaacacttc  420
taaatctcaa aatgggtcaa aaatgtttta actagaagcc caagcccatt aaacaggcaa  480
tgaatgacgt cattaccgta ggaattggtg gtctggaaa ggccaactcg acaaaactaa  540
caaactttgc gtgta agcggagcgt aagacacgta atccttttata cgtggcctaa  600
tataattggt aacccctagtc aagtgggttt ggtttggcct gaccaagtcg gtttaggatt  660
tatccatttc cttcttttttt aaaaaaagaa atatcagaga aagtcggtca agttgattta  720
taaattgcct cttaccccttc atctttcatc                                  750

SEQ ID NO: 12           moltype = DNA  length = 22
```

```
FEATURE                 Location/Qualifiers
misc_feature            1..22
                        note = Single strand DNA oligonucleotide
source                  1..22
                        mol_type = other DNA
                        organism = synthetic construct
SEQUENCE: 12
gccgcttggg tggagaggct at                                                  22

SEQ ID NO: 13           moltype = DNA   length = 21
FEATURE                 Location/Qualifiers
misc_feature            1..21
                        note = Single strand DNA oligonucleotide
source                  1..21
                        mol_type = other DNA
                        organism = synthetic construct
SEQUENCE: 13
gaggaagcgg tcagcccatt c                                                   21

SEQ ID NO: 14           moltype = DNA   length = 22
FEATURE                 Location/Qualifiers
misc_feature            1..22
                        note = Single strand DNA oligonucleotide
source                  1..22
                        mol_type = other DNA
                        organism = synthetic construct
SEQUENCE: 14
cgagcgattt ggtcatgtga ag                                                  22

SEQ ID NO: 15           moltype = DNA   length = 25
FEATURE                 Location/Qualifiers
misc_feature            1..25
                        note = Single strand DNA oligonucleotide
source                  1..25
                        mol_type = other DNA
                        organism = synthetic construct
SEQUENCE: 15
cattgtttgc ctccctgctg cggtt                                               25

SEQ ID NO: 16           moltype = DNA   length = 32
FEATURE                 Location/Qualifiers
misc_feature            1..32
                        note = Single strand DNA oligonucleotide
source                  1..32
                        mol_type = other DNA
                        organism = synthetic construct
SEQUENCE: 16
atgagtatta ttactaatga tagtaatctc ag                                       32

SEQ ID NO: 17           moltype = DNA   length = 25
FEATURE                 Location/Qualifiers
misc_feature            1..25
                        note = Single strand DNA oligonucleotide
source                  1..25
                        mol_type = other DNA
                        organism = synthetic construct
SEQUENCE: 17
ttattccatg ccgaatattg gtgtt                                               25

SEQ ID NO: 18           moltype = DNA   length = 24
FEATURE                 Location/Qualifiers
misc_feature            1..24
                        note = Single strand DNA oligonucleotide
source                  1..24
                        mol_type = other DNA
                        organism = synthetic construct
SEQUENCE: 18
tggaaggtga tgccttgcat agtc                                                24

SEQ ID NO: 19           moltype = DNA   length = 25
FEATURE                 Location/Qualifiers
misc_feature            1..25
                        note = Single strand DNA oligonucleotide
source                  1..25
                        mol_type = other DNA
                        organism = synthetic construct
SEQUENCE: 19
ttacctcgga ccagataact cgacc                                               25
```